(12) United States Patent
Kim et al.

(10) Patent No.: US 11,607,238 B2
(45) Date of Patent: Mar. 21, 2023

(54) SURGICAL APPARATUS

(71) Applicant: BOARD OF REGENTS OF THE UNIVERSITY OF TEXAS SYSTEM, Austin, TX (US)

(72) Inventors: Daniel H. Kim, Houston, TX (US); Dong Suk Shin, Houston, TX (US); Taeho Jang, Houston, TX (US); Yong Man Park, Houston, TX (US)

(73) Assignee: BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 17/855,744

(22) Filed: Jun. 30, 2022

(65) Prior Publication Data
US 2022/0354524 A1  Nov. 10, 2022

Related U.S. Application Data

(62) Division of application No. 15/562,594, filed as application No. PCT/US2017/016485 on Feb. 3, 2017, now Pat. No. 11,504,144.
(Continued)

(51) Int. Cl.
*A61B 17/29* (2006.01)
*A61B 34/37* (2016.01)
(Continued)

(52) U.S. Cl.
CPC ........ *A61B 17/2909* (2013.01); *A61B 1/3132* (2013.01); *A61B 17/29* (2013.01); *A61B 34/37* (2016.02); *A61B 34/74* (2016.02); *A61B 2017/0046* (2013.01); *A61B 2017/00309* (2013.01); *A61B 2017/00314* (2013.01);
(Continued)

(58) Field of Classification Search
CPC ........ A61B 34/30; A61B 34/70; A61B 34/71; A61B 2034/301–306; A61B 2034/715; A61B 1/0051–0057; A61B 2017/00292; A61B 2017/003; A61B 2017/00314;
(Continued)

(56) References Cited

U.S. PATENT DOCUMENTS

| 5,174,168 A | 12/1992 | Takagi et al. |
| 5,329,923 A | 7/1994 | Lundquist |

(Continued)

FOREIGN PATENT DOCUMENTS

| AU | 2001089246 A1 | 2/2002 |
| CN | 1728972 A | 2/2006 |

(Continued)

OTHER PUBLICATIONS

Australian Application No. 2021204249, Notice of Acceptance dated May 12, 2022, 4 pages.
(Continued)

*Primary Examiner* — Todd J Scherbel
(74) *Attorney, Agent, or Firm* — Patterson + Sheridan, LLP

(57) ABSTRACT

The disclosure provides a surgical apparatus comprising: a steerable member that is bendable and comprises a plurality of bending segments with channels therein; and a plurality of bending actuation wires that are arranged to pass through the steerable member and cause the steerable member to bend, the steerable member comprising at least one outwardly opening lumen through which the bending actuation wires pass.

10 Claims, 42 Drawing Sheets

Related U.S. Application Data

(60) Provisional application No. 62/424,273, filed on Nov. 18, 2016, provisional application No. 62/292,057, filed on Feb. 7, 2016.

(51) Int. Cl.
*A61B 34/00* (2016.01)
*A61B 1/313* (2006.01)
*A61B 17/00* (2006.01)
*A61B 90/00* (2016.01)
*A61B 34/30* (2016.01)

(52) U.S. Cl.
CPC ............ *A61B 2017/00323* (2013.01); *A61B 2017/291* (2013.01); *A61B 2017/2906* (2013.01); *A61B 2034/301* (2016.02); *A61B 2034/306* (2016.02); *A61B 2034/715* (2016.02); *A61B 2090/064* (2016.02)

(58) Field of Classification Search
CPC ........... A61B 2017/00318; A61B 2017/00323; A61B 2017/00327; A61B 2017/00336
See application file for complete search history.

(56) References Cited

U.S. PATENT DOCUMENTS

| | | |
|---|---|---|
| 5,337,732 A | 8/1994 | Grundfest et al. |
| 5,534,762 A | 7/1996 | Kim |
| 5,624,380 A | 4/1997 | Takayama et al. |
| 6,162,171 A | 12/2000 | Ng et al. |
| 6,244,644 B1 | 6/2001 | Lovchik et al. |
| 6,398,726 B1 | 6/2002 | Ramans et al. |
| 6,417,638 B1 | 7/2002 | Guy et al. |
| 6,468,203 B2 | 10/2002 | Belson |
| 6,554,844 B2 | 4/2003 | Lee et al. |
| 6,587,750 B2 | 7/2003 | Gerbi et al. |
| 6,610,007 B2 | 8/2003 | Belson et al. |
| 6,679,836 B2 | 1/2004 | Couvillon, Jr. |
| 6,684,129 B2 | 1/2004 | Salisbury, Jr. et al. |
| 6,699,235 B2 | 3/2004 | Wallace et al. |
| 6,817,974 B2 | 11/2004 | Cooper et al. |
| 6,835,173 B2 | 12/2004 | Couvillon, Jr. |
| 6,858,005 B2 | 2/2005 | Ohline et al. |
| 6,869,396 B2 | 3/2005 | Belson |
| 6,879,315 B2 | 4/2005 | Guy et al. |
| 6,879,880 B2 | 4/2005 | Nowlin et al. |
| 6,890,297 B2 | 5/2005 | Belson |
| 6,949,106 B2 | 9/2005 | Brock et al. |
| 6,969,395 B2 | 11/2005 | Eskur |
| 6,997,870 B2 | 2/2006 | Couvillon, Jr. |
| 7,044,907 B2 | 5/2006 | Belson |
| 7,063,671 B2 | 6/2006 | Couvillon, Jr. |
| 7,087,013 B2 | 8/2006 | Belson et al. |
| 7,097,615 B2 | 8/2006 | Banik et al. |
| 7,101,363 B2 | 9/2006 | Nishizawa et al. |
| 7,169,141 B2 | 1/2007 | Brock et al. |
| 7,199,052 B2 | 4/2007 | Cohen |
| 7,261,686 B2 | 8/2007 | Couvillon, Jr. |
| 7,320,700 B2 | 1/2008 | Cooper et al. |
| 7,411,576 B2 | 8/2008 | Massie et al. |
| 7,503,474 B2 | 3/2009 | Hillstead et al. |
| 7,543,518 B2 | 6/2009 | Buckingham et al. |
| 7,574,250 B2 | 8/2009 | Niemeyer |
| 7,608,083 B2 | 10/2009 | Lee et al. |
| 7,615,066 B2 | 11/2009 | Danitz et al. |
| 7,631,834 B1 | 12/2009 | Johnson et al. |
| 7,666,135 B2 | 2/2010 | Couvillon, Jr. |
| 7,678,117 B2 | 3/2010 | Hinman et al. |
| 7,736,356 B2 | 6/2010 | Cooper et al. |
| 7,744,608 B2 | 6/2010 | Lee et al. |
| 7,744,622 B2 | 6/2010 | Brock et al. |
| RE41,475 E | 8/2010 | Grabover et al. |
| 7,766,896 B2 | 8/2010 | Kornkven Volk et al. |
| 7,819,884 B2 | 10/2010 | Lee et al. |
| 7,854,738 B2 | 12/2010 | Lee et al. |
| 7,862,580 B2 | 1/2011 | Cooper et al. |
| 7,879,004 B2 | 2/2011 | Seibel et al. |
| 7,909,844 B2 | 3/2011 | Alkhatib et al. |
| 7,955,321 B2 | 6/2011 | Kishi et al. |
| 8,020,468 B2 | 9/2011 | Yang |
| 8,021,377 B2 | 9/2011 | Eskuri |
| 8,062,212 B2 | 11/2011 | Belson |
| 8,069,747 B2 | 12/2011 | Buckingham et al. |
| 8,083,669 B2 | 12/2011 | Murakami et al. |
| 8,092,371 B2 | 1/2012 | Miyamoto et al. |
| 8,114,097 B2 | 2/2012 | Brock et al. |
| 8,123,740 B2 | 2/2012 | Madhani et al. |
| 8,133,199 B2 | 3/2012 | Weber et al. |
| 8,142,421 B2 | 3/2012 | Cooper et al. |
| 8,182,418 B2 | 5/2012 | Durant et al. |
| 8,187,169 B2 | 5/2012 | Sugiyama et al. |
| 8,192,422 B2 | 6/2012 | Zubiate et al. |
| 8,206,429 B2 | 6/2012 | Gregorich et al. |
| 8,224,485 B2 | 7/2012 | Unsworth |
| 8,226,546 B2 | 7/2012 | Belson |
| 8,306,656 B1 | 11/2012 | Schaible et al. |
| 8,317,777 B2 | 11/2012 | Zubiate et al. |
| 8,323,297 B2 | 12/2012 | Hinman et al. |
| 8,328,714 B2 | 12/2012 | Couvillon, Jr. |
| 8,337,521 B2 | 12/2012 | Cooper et al. |
| 8,347,754 B1 | 1/2013 | Veltri et al. |
| 8,348,834 B2 | 1/2013 | Bakos |
| 8,365,633 B2 | 2/2013 | Simaan et al. |
| 8,366,604 B2 | 2/2013 | Konstorum |
| 8,414,598 B2 | 4/2013 | Brock et al. |
| 8,414,632 B2 | 4/2013 | Kornkven Volk et al. |
| 8,439,828 B2 | 5/2013 | Dejima et al. |
| 8,444,547 B2 | 5/2013 | Miyamoto et al. |
| 8,483,880 B2 | 7/2013 | de la Rosa Tames et al. |
| 8,486,010 B2 | 7/2013 | Nomura |
| 8,517,921 B2 | 8/2013 | Tremaglio et al. |
| 8,517,924 B2 | 8/2013 | Banik et al. |
| 8,517,926 B2 | 8/2013 | Uchimura |
| 8,523,899 B2 | 9/2013 | Suzuki |
| 8,578,810 B2 | 11/2013 | Donhowe |
| 8,608,647 B2 | 12/2013 | Durant et al. |
| 8,617,054 B2 | 12/2013 | Miyamoto et al. |
| 8,641,602 B2 | 2/2014 | Belson |
| 8,644,988 B2 | 2/2014 | Prisco et al. |
| 8,663,097 B2 | 3/2014 | Arai |
| 8,672,837 B2 | 3/2014 | Roelle et al. |
| 8,679,004 B2 | 3/2014 | Konstorum |
| 8,708,892 B2 | 4/2014 | Sugiyama et al. |
| 8,715,270 B2 | 5/2014 | Weitzner et al. |
| 8,721,530 B2 | 5/2014 | Ohline et al. |
| 8,758,232 B2 | 6/2014 | Graham et al. |
| 8,768,509 B2 | 7/2014 | Unsworth |
| 8,771,260 B2 | 7/2014 | Conlon et al. |
| 8,777,843 B2 | 7/2014 | Banju et al. |
| 8,790,243 B2 | 7/2014 | Cooper et al. |
| 8,827,894 B2 | 9/2014 | Belson |
| 8,827,948 B2 | 9/2014 | Romo et al. |
| 8,834,354 B2 | 9/2014 | Belson |
| 8,834,390 B2 | 9/2014 | Couvillon, Jr. |
| 8,845,524 B2 | 9/2014 | Belson et al. |
| 8,845,622 B2 | 9/2014 | Paik et al. |
| 8,888,764 B2 | 11/2014 | Devengenzo et al. |
| 8,919,348 B2 | 12/2014 | Williams et al. |
| 8,920,970 B2 | 12/2014 | Sunkara et al. |
| 8,927,048 B2 | 1/2015 | Leeflang et al. |
| 8,986,196 B2 | 3/2015 | Larkin et al. |
| 9,055,961 B2 | 6/2015 | Manzo et al. |
| 9,060,678 B2 | 6/2015 | Larkin et al. |
| 9,060,796 B2 | 6/2015 | Seo |
| 9,147,825 B2 | 9/2015 | Kim et al. |
| 9,149,274 B2 | 10/2015 | Spivey et al. |
| 9,173,548 B2 | 11/2015 | Omori |
| 9,173,713 B2 | 11/2015 | Hart et al. |
| 9,192,447 B2 | 11/2015 | Choi et al. |
| 9,193,451 B2 | 11/2015 | Salyer |
| 9,205,560 B1 | 12/2015 | Edsinger et al. |
| 9,259,274 B2 | 2/2016 | Prisco |
| 9,289,266 B2 | 3/2016 | Weitzner et al. |

(56) References Cited

U.S. PATENT DOCUMENTS

| | | |
|---|---|---|
| 9,314,309 B2 | 4/2016 | Seo |
| 9,345,462 B2 | 5/2016 | Weitzner et al. |
| 9,358,031 B2 | 6/2016 | Manzo |
| 9,370,640 B2 | 6/2016 | Zhang et al. |
| 9,393,000 B2 | 7/2016 | Donhowe |
| 9,498,601 B2 | 11/2016 | Tanner et al. |
| 9,561,083 B2 | 2/2017 | Yu et al. |
| 9,724,162 B2 | 8/2017 | Crainich et al. |
| 2002/0120252 A1 | 8/2002 | Brock et al. |
| 2002/0133173 A1 | 9/2002 | Brock et al. |
| 2003/0006669 A1 | 1/2003 | Pei et al. |
| 2005/0096502 A1 | 5/2005 | Khalili |
| 2005/0103706 A1 | 5/2005 | Bennett et al. |
| 2005/0131279 A1 | 6/2005 | Boulais et al. |
| 2005/0216033 A1 | 9/2005 | Lee et al. |
| 2006/0058582 A1 | 3/2006 | Maahs et al. |
| 2006/0111618 A1 | 5/2006 | Couvillon |
| 2006/0266642 A1 | 11/2006 | Akle et al. |
| 2007/0027519 A1 | 2/2007 | Ortiz et al. |
| 2007/0112311 A1 | 5/2007 | Harding et al. |
| 2007/0123750 A1 | 5/2007 | Baumgartner et al. |
| 2007/0249909 A1 | 10/2007 | Volk et al. |
| 2007/0250036 A1 | 10/2007 | Volk et al. |
| 2007/0299422 A1 | 12/2007 | Inganas et al. |
| 2007/0299427 A1 | 12/2007 | Yeung et al. |
| 2008/0051829 A1 | 2/2008 | Eidenschink et al. |
| 2008/0086081 A1 | 4/2008 | Eidenschink et al. |
| 2008/0177282 A1 | 7/2008 | Lee et al. |
| 2008/0188868 A1 | 8/2008 | Weitzner et al. |
| 2008/0188869 A1 | 8/2008 | Weitzner et al. |
| 2008/0188871 A1 | 8/2008 | Smith et al. |
| 2008/0221391 A1 | 9/2008 | Weitzner et al. |
| 2008/0243175 A1 | 10/2008 | Moore et al. |
| 2009/0024086 A1 | 1/2009 | Zhang et al. |
| 2009/0082723 A1 | 3/2009 | Krogh et al. |
| 2009/0105645 A1 | 4/2009 | Kidd et al. |
| 2009/0149702 A1 | 6/2009 | Onoda et al. |
| 2009/0157048 A1 | 6/2009 | Sutermeister et al. |
| 2009/0171160 A1 | 7/2009 | Ito et al. |
| 2009/0171161 A1 | 7/2009 | Ewers et al. |
| 2009/0259141 A1 | 10/2009 | Ewers et al. |
| 2009/0326319 A1 | 12/2009 | Takahashi et al. |
| 2010/0010309 A1 | 1/2010 | Kitagawa |
| 2010/0101346 A1 | 4/2010 | Johnson et al. |
| 2010/0113875 A1 | 5/2010 | Yi et al. |
| 2010/0300230 A1 | 12/2010 | Helmer |
| 2011/0040408 A1 | 2/2011 | De La Rosa Tames et al. |
| 2011/0092963 A1 | 4/2011 | Castro |
| 2011/0100146 A1 | 5/2011 | Feng |
| 2011/0251599 A1 | 10/2011 | Shellenberger et al. |
| 2011/0295063 A1 | 12/2011 | Umemoto et al. |
| 2012/0004502 A1 | 1/2012 | Weitzner et al. |
| 2012/0071863 A1 | 3/2012 | Lee et al. |
| 2012/0078053 A1 | 3/2012 | Phee et al. |
| 2012/0143174 A1 | 6/2012 | Choi et al. |
| 2012/0179097 A1 | 7/2012 | Cully et al. |
| 2012/0220831 A1 | 8/2012 | Cooper et al. |
| 2012/0238952 A1 | 9/2012 | Mitchell et al. |
| 2012/0239032 A1 | 9/2012 | Zhang et al. |
| 2013/0035537 A1 | 2/2013 | Wallace et al. |
| 2013/0072913 A1 | 3/2013 | Yi et al. |
| 2013/0123692 A1 | 5/2013 | Zhang et al. |
| 2013/0199327 A1 | 8/2013 | Park et al. |
| 2013/0213170 A1 | 8/2013 | Kim et al. |
| 2013/0218005 A1 | 8/2013 | Desai et al. |
| 2013/0253424 A1 | 9/2013 | Kim et al. |
| 2013/0255410 A1 | 10/2013 | Lee et al. |
| 2013/0263424 A1 | 10/2013 | Giocastro |
| 2013/0281924 A1 | 10/2013 | Shellenberger |
| 2014/0005683 A1 | 1/2014 | Stand et al. |
| 2014/0012286 A1 | 1/2014 | Lee et al. |
| 2014/0046305 A1 | 2/2014 | Castro et al. |
| 2014/0107570 A1 | 4/2014 | Mitchell et al. |
| 2014/0142591 A1 | 5/2014 | Alvarez et al. |
| 2014/0142592 A1 | 5/2014 | Moon et al. |
| 2014/0163318 A1 | 6/2014 | Swanstrom |
| 2014/0163327 A1 | 6/2014 | Swanstrom |
| 2014/0180089 A1 | 6/2014 | Alpert et al. |
| 2014/0228631 A1 | 8/2014 | Kwak et al. |
| 2014/0243592 A1 | 8/2014 | Kato et al. |
| 2014/0257329 A1 | 9/2014 | Jang et al. |
| 2014/0257330 A1 | 9/2014 | Choi et al. |
| 2014/0276594 A1 | 9/2014 | Tanner et al. |
| 2014/0276940 A1 | 9/2014 | Seo |
| 2014/0288413 A1 | 9/2014 | Hwang et al. |
| 2014/0303643 A1 | 10/2014 | Ha et al. |
| 2014/0324070 A1 | 10/2014 | Min et al. |
| 2014/0336669 A1 | 11/2014 | Park |
| 2014/0379000 A1 | 12/2014 | Romo et al. |
| 2015/0018841 A1 | 1/2015 | Seo |
| 2015/0045812 A1 | 2/2015 | Seo |
| 2015/0066051 A1 | 3/2015 | Kwon et al. |
| 2015/0088060 A1 | 3/2015 | Wang et al. |
| 2015/0101442 A1 | 4/2015 | Romo |
| 2015/0105629 A1 | 4/2015 | Williams et al. |
| 2015/0119637 A1 | 4/2015 | Alvarez et al. |
| 2015/0119638 A1 | 4/2015 | Yu et al. |
| 2015/0119903 A1 | 4/2015 | Hinman et al. |
| 2015/0133858 A1 | 5/2015 | Julian et al. |
| 2015/0164594 A1 | 6/2015 | Romo et al. |
| 2015/0164595 A1 | 6/2015 | Bogusky et al. |
| 2015/0164596 A1 | 6/2015 | Romo et al. |
| 2015/0165163 A1 | 6/2015 | Alvarez et al. |
| 2015/0230869 A1 | 8/2015 | Shim et al. |
| 2015/0297865 A1 | 10/2015 | Hinman et al. |
| 2015/0335480 A1 | 11/2015 | Alvarez et al. |
| 2016/0001038 A1 | 1/2016 | Romo et al. |
| 2016/0151122 A1 | 6/2016 | Alvarez et al. |
| 2016/0151908 A1 | 6/2016 | Woodley et al. |
| 2016/0184032 A1 | 6/2016 | Romo et al. |
| 2016/0270865 A1 | 9/2016 | Landey et al. |
| 2016/0270866 A1 | 9/2016 | Yu et al. |
| 2016/0287279 A1 | 10/2016 | Bovay et al. |
| 2016/0287840 A1 | 10/2016 | Jiang |
| 2016/0296294 A1 | 10/2016 | Moll et al. |
| 2016/0331477 A1 | 11/2016 | Yu et al. |
| 2016/0331613 A1 | 11/2016 | Lee et al. |
| 2016/0374541 A1 | 12/2016 | Agrawal et al. |
| 2016/0374766 A1 | 12/2016 | Schuh |

FOREIGN PATENT DOCUMENTS

| | | |
|---|---|---|
| EP | 1876504 A1 | 1/2008 |
| EP | 2737922 A1 | 6/2014 |
| JP | 61-188701 | 11/1986 |
| JP | H1119032 A | 1/1999 |
| JP | 2000279376 A | 10/2000 |
| JP | 2004350495 A | 12/2004 |
| JP | 2005216743 A | 8/2005 |
| JP | 2006521882 A | 9/2006 |
| JP | 2007029274 A | 2/2007 |
| JP | 2007502198 A | 2/2007 |
| JP | 2007175517 A | 7/2007 |
| JP | 2009136566 A | 6/2009 |
| JP | 2010017483 A | 1/2010 |
| JP | 2012512670 A | 6/2012 |
| JP | 2013208506 A | 10/2013 |
| JP | 2013540004 A | 10/2013 |
| JP | 2014500070 A | 1/2014 |
| JP | 2015163413 A | 9/2015 |
| WO | 03001986 A2 | 1/2003 |
| WO | 2003105671 A2 | 12/2003 |
| WO | 2004/052171 A2 | 6/2004 |
| WO | 2006084744 A2 | 8/2006 |
| WO | 2010039387 A1 | 4/2010 |
| WO | 2011060317 A2 | 5/2011 |
| WO | 2011108161 A1 | 9/2011 |
| WO | 2012070838 A2 | 5/2012 |
| WO | 2012167043 A2 | 12/2012 |
| WO | 2012168936 A1 | 12/2012 |
| WO | 2013162206 A1 | 10/2013 |
| WO | 2014126653 A1 | 8/2014 |
| WO | 2014189876 A1 | 11/2014 |

(56) References Cited

FOREIGN PATENT DOCUMENTS

| WO | 2015057990 A1 | 4/2015 |
|----|---------------|--------|
| WO | 2015127250 A1 | 8/2015 |
| WO | 2015142290 A1 | 9/2015 |

OTHER PUBLICATIONS

Australian Application No. 2021204249, Examination Report No. 1 dated Jan. 18, 2022, 5 pages.
Australian Application No. 2021204243, Examination Report No. 1 dated Jan. 18, 2022, 4 pages.
Canadian Application No. 3,004,197, Office Action dated May 13, 2021, 3 pages.
Canadian Application No. 3,004,197, Office Action dated May 25, 2022, 6 pages.
Canadian Application No. 3,152,866, Office Action dated Jun. 8, 2022, 7 pages.
Japanese Application No. 2019-192101, Office Action dated Jun. 14, 2022, 5 pages.
Japanese Application No. 2020-139162, Office Action dated Apr. 26, 2022, 6 pages.
Mexican Patent Application No. MX/a/2018/006000, Office Action dated May 10, 2022, 4 pages.
Brazilian patent application BR 12 2022 007758-7, Office Action, dated Jun. 14, 2022, 5 pages.
Brazilian patent application BR 12 2022 007759-5, Office Action, dated Jun. 14, 2022, 5 pages.
Brazilian patent application BR 12 2022 007760-9, Office Action, dated Jun. 14, 2022, 5 pages.
Brazilian patent application BR 12 2022 007761-7, Office Action, dated Jun. 14, 2022, 5 pages.
European Search Report, Application No. 17748266.8, dated Jan. 2, 2019, 9 pages.
Supplemental Partial European Search Report, EP17748276, dated Oct. 15, 2018, 18 pages.
Japanese Patent Application No. 2018-541212, Office Action dated Jul. 17, 2019, 10 pages.
European Application No. 17748266.8, Communication pursuant to Article 94(3) EPC dated Oct. 30, 2019, 5 pages.
Australian Applicatiion No. 2017214552, Examination Report No. 1, dated Mar. 12, 2020, 5 pages.
Japanese Patent Application No. 2018-541212, Notice of Reasons for Rejection dated Mar. 31, 2020, 8 pages.
European Application No. 17748266.8, Communication pursuant to Article 94(3) EPC dated Jun. 16, 2020, 4 pages.
Chinese Application No. 201780007593.6, Frist Notification of Office Action dated Jun. 22, 2020, 17 pages.
Australian Application No. 2020227057, Examination Report No. 1 dated Sep. 23, 2020, 6 pages.
Australian Application No. 2020227056, Examination Report No. 1 dated Sep. 29, 2020, 5 pages.
Japanese Patent Application No. 2019-192101, Office Action dated Dec. 22, 2020 w/English translation, 11 pages.
Canadian Patent Application No. 3,004,197, Office Action dated Dec. 9, 2021, 6 pages.
Japanese Patent Application No. 2019-192101, Office Action dated Nov. 2, 2021 w/English translation, 11 pages.
Japanese Patent Application No. 2020-139164, Office Action dated Jun. 22, 2021 w/English translation, 12 pages.
Japanese Patent Application No. 2020-139163, Office Action dated Jun. 29, 2021 w/English translation, 9 pages.
Japanese Patent Application No. 2020-139162, Office Action dated Jul. 6, 2021 w/English translation, 12 pages.
Korean Patent Application No. 10-2018-7019036, Office Action dated Jul. 27, 2021 w/Eng Translation, 13 pages.

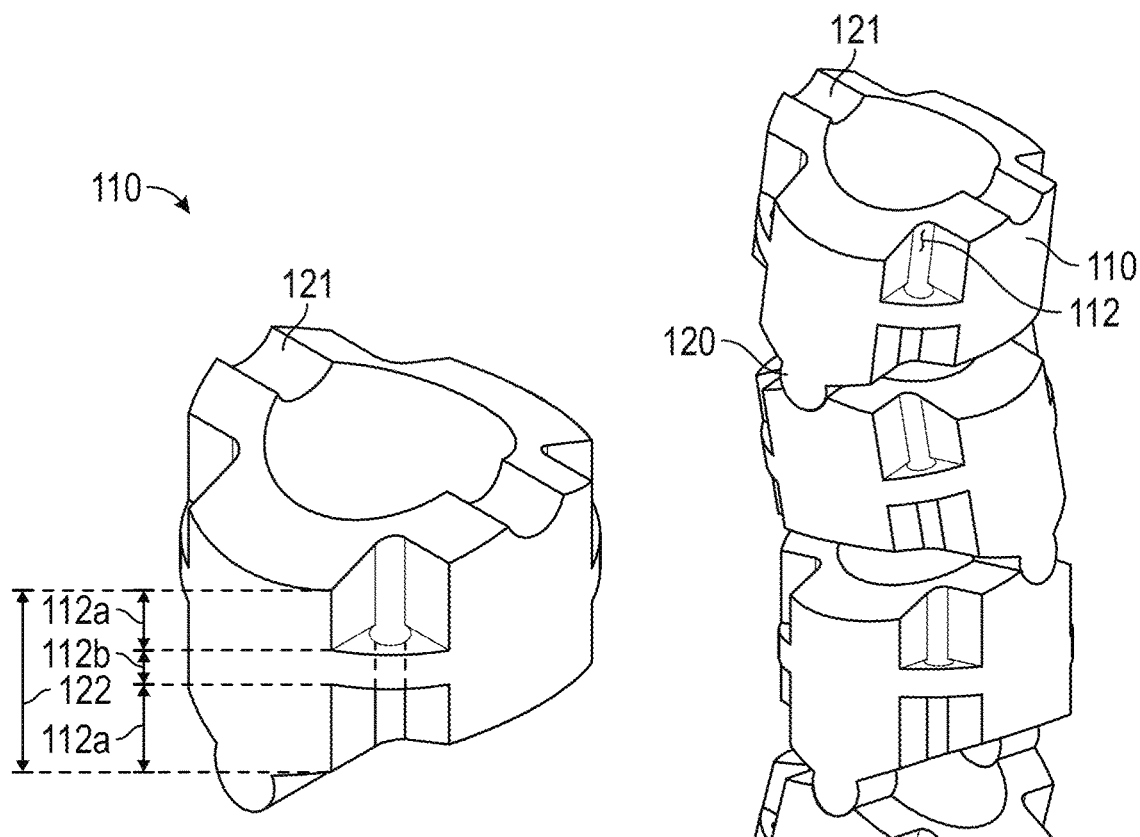
FIG. 8A
FIG. 8B
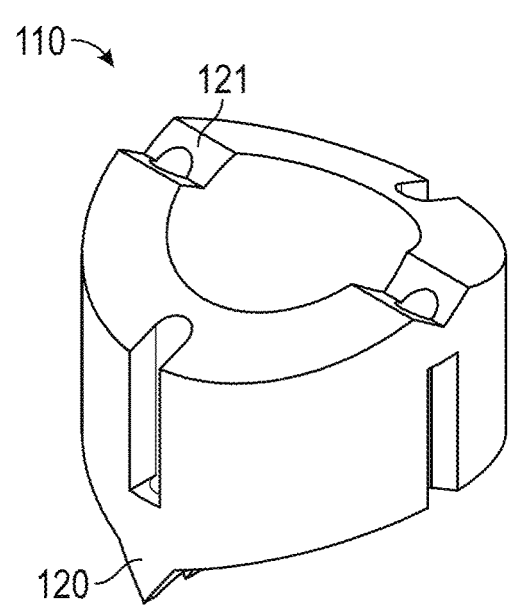
FIG. 9A
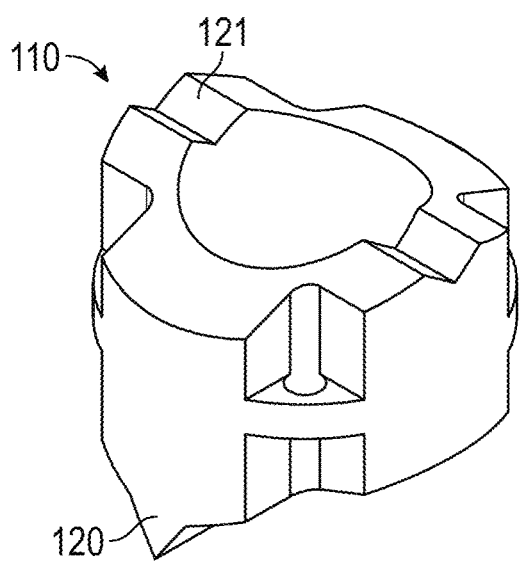
FIG. 9B

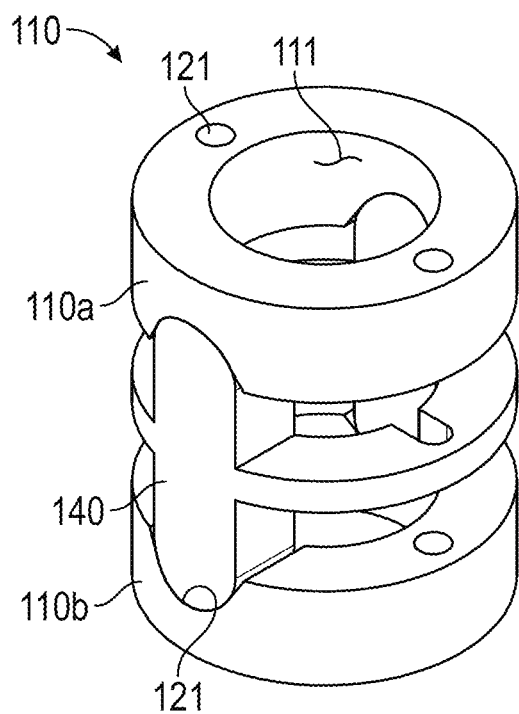 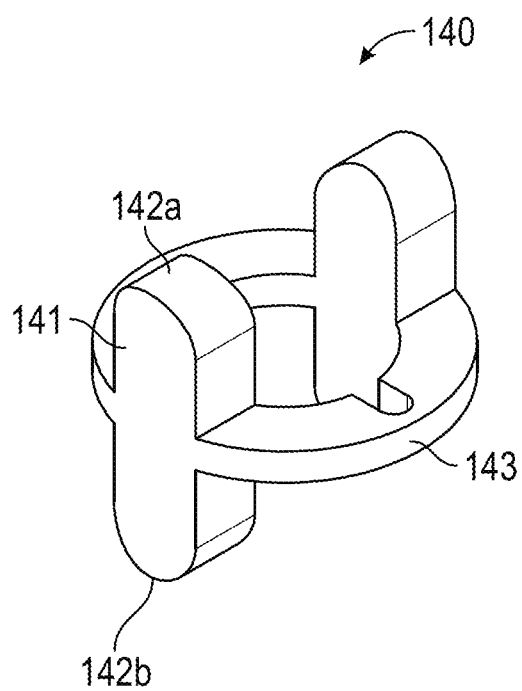
FIG. 16A  FIG. 16B
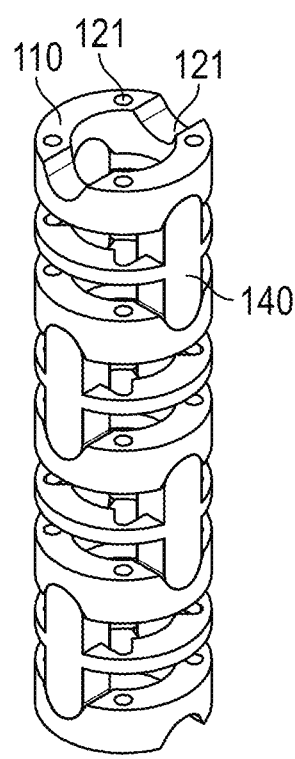 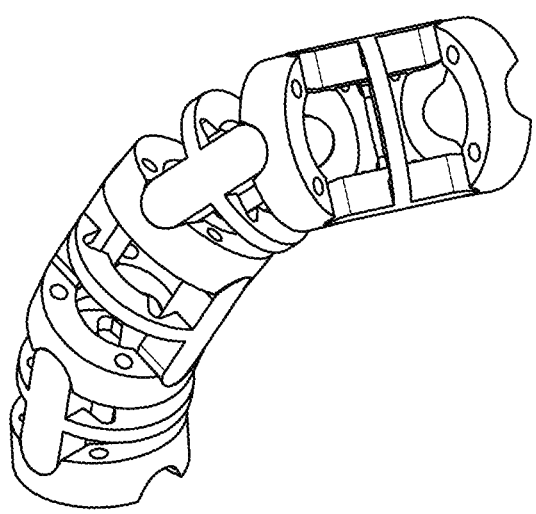
FIG. 17A  FIG. 17B

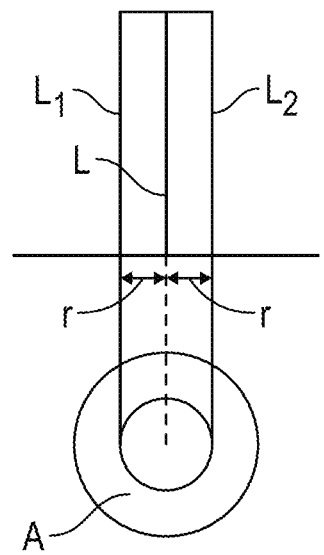
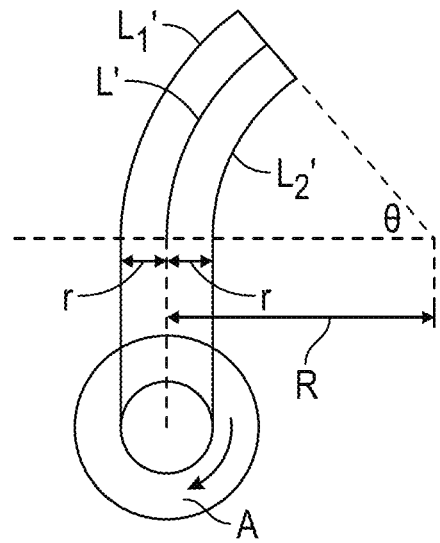
FIG. 33A　　　　　FIG. 33B
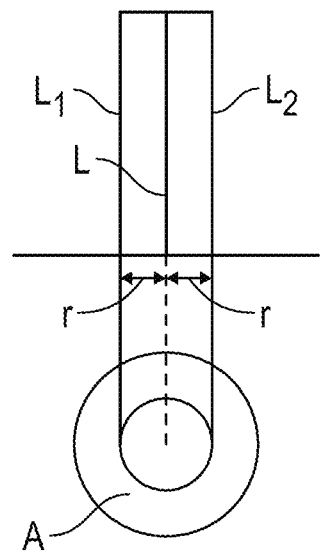
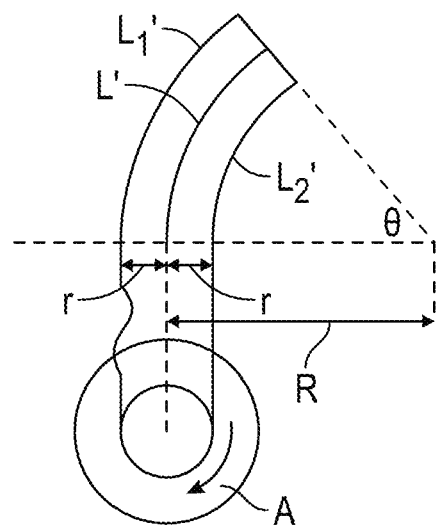
FIG. 34A　　　　　FIG. 34B

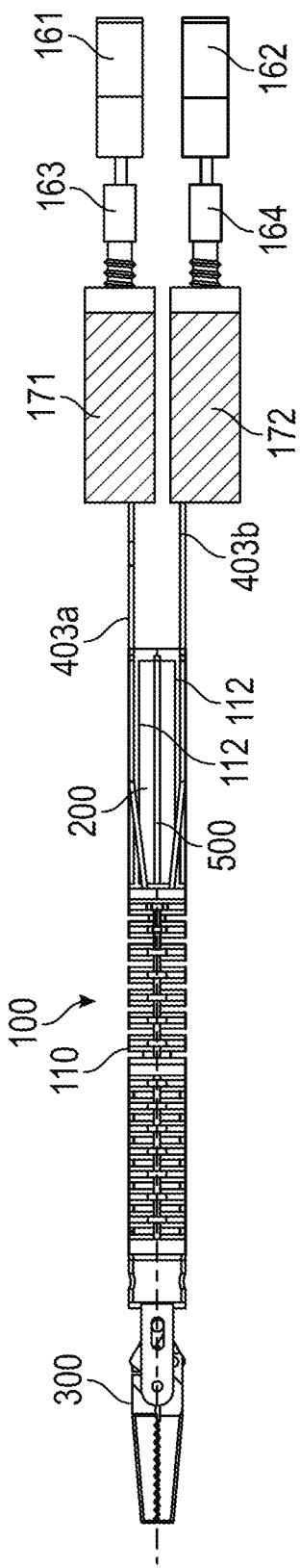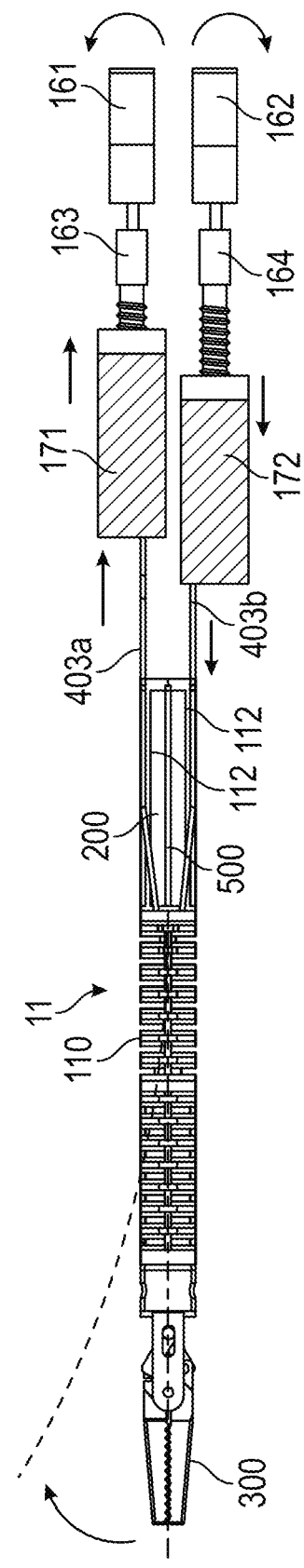
FIG. 41
FIG. 42

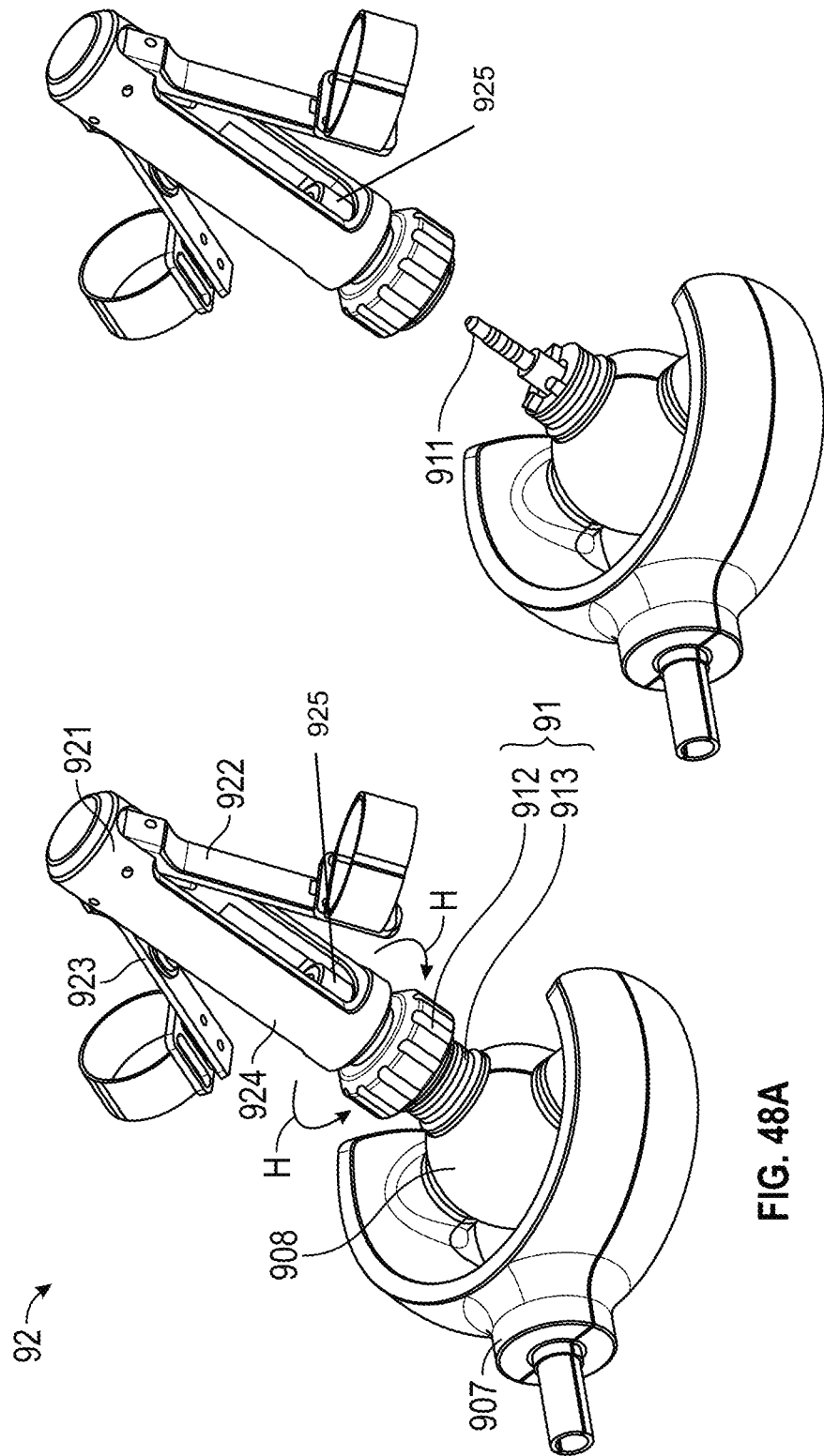

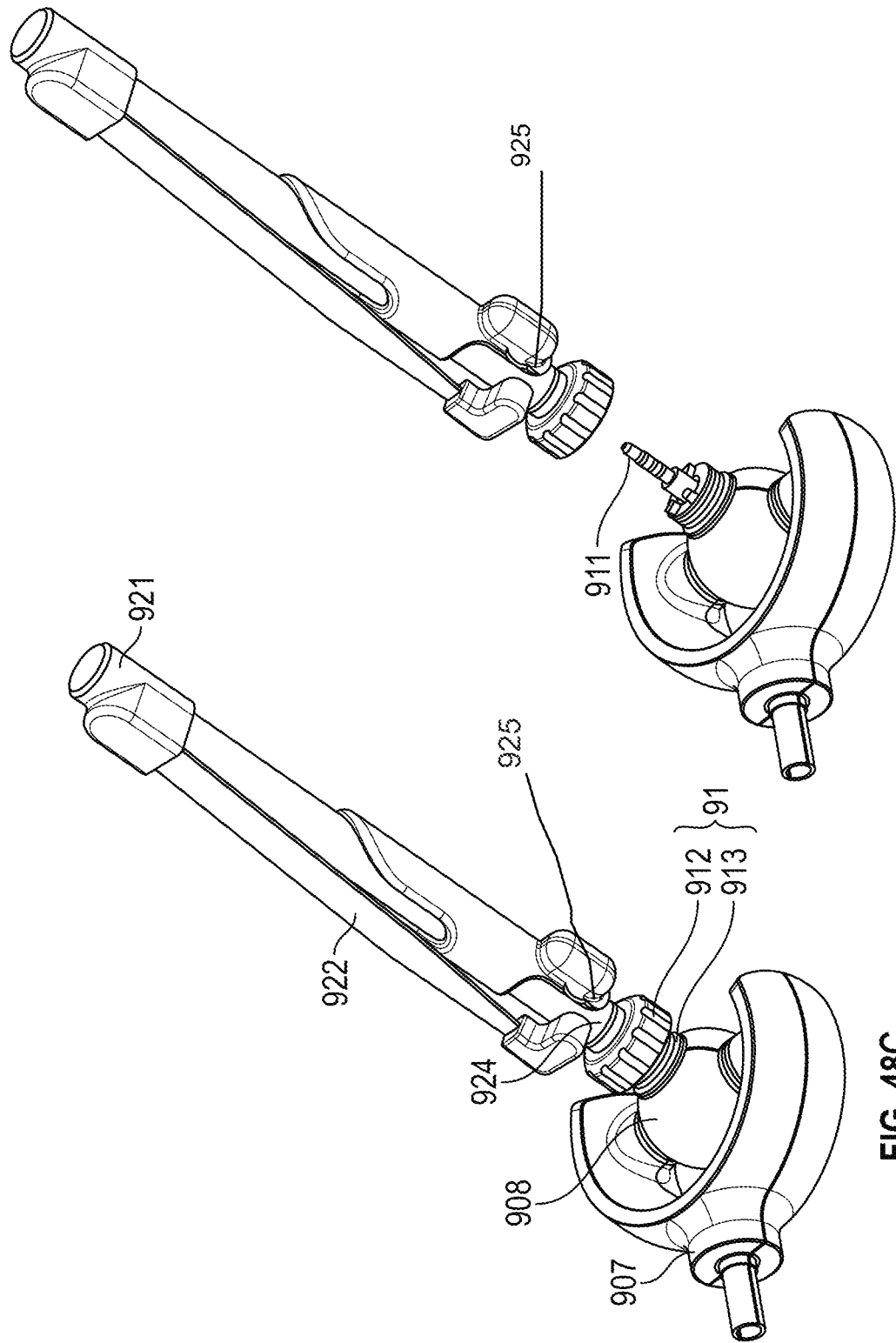

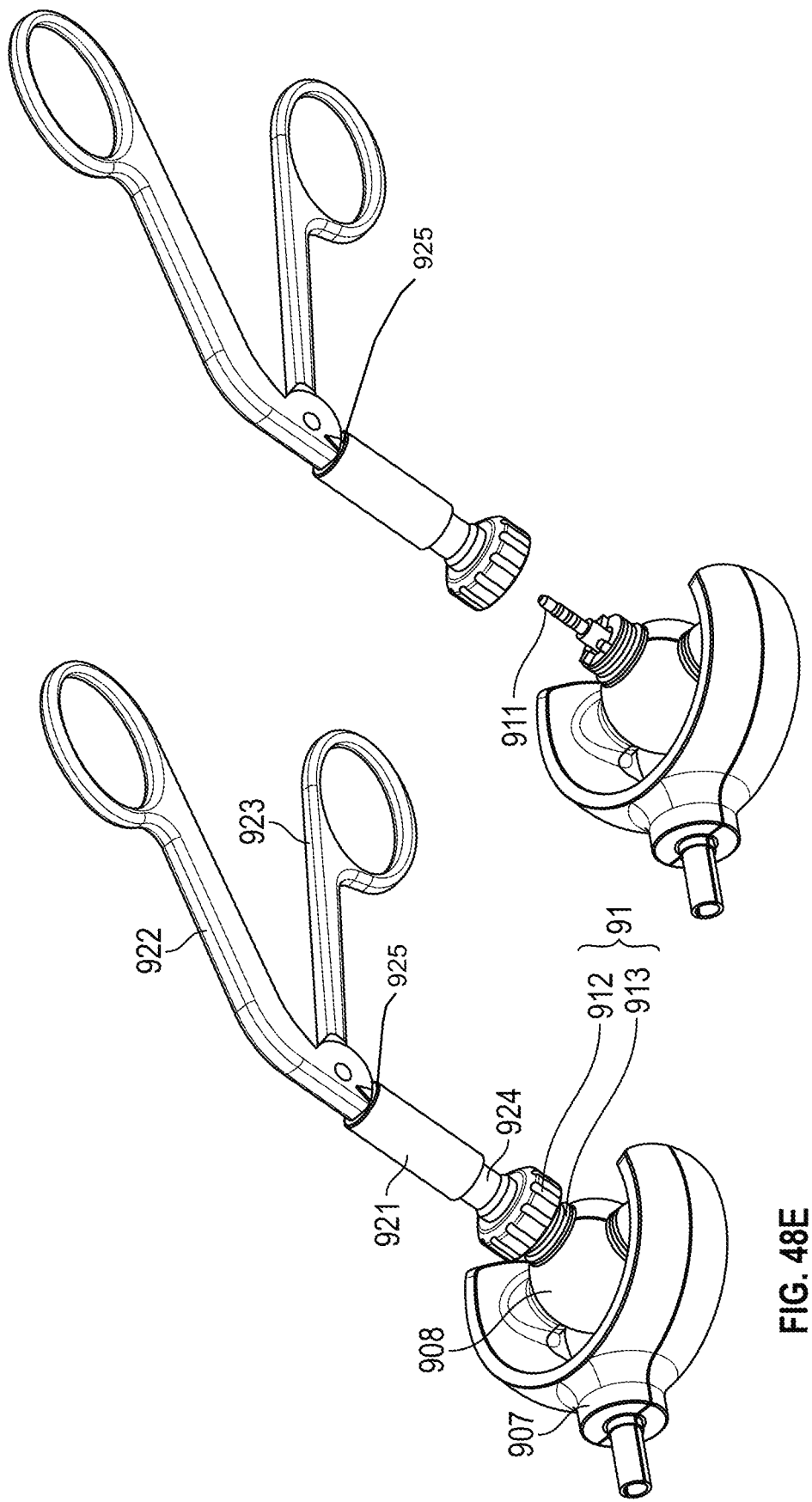

SURGICAL APPARATUS

CROSS-REFERENCE TO RELATED APPLICATIONS

This Application is a divisional of application Ser. No. 15/562,594, filed Feb. 3, 2017, which claims priority to 371 U.S. National Stage of International Application No. PCT/US2017/016485, filed Feb. 3, 2017, and claims the benefit of priority from U.S. Provisional Application No. 62/292,057, filed Feb. 7, 2016, entitled "SURGICAL APPARATUS," and U.S. Provisional Application No. 62/424,273, filed Nov. 18, 2016, entitled "SURGICAL APPARATUS," which are fully incorporated by reference herein in their entirety.

BACKGROUND

Field

The present invention relates to a surgical apparatus, and more particularly, to a surgical apparatus which is capable of performing a bending mechanism by including a bendable element at the distal end.

Description of the Related Art

Surgical apparatuses used in surgery have different structures depending on the location of a surgical site and how the surgical site will be treated. In recent years, various types of surgical equipment using a robot are being developed to perform surgery on areas where surgical sites are difficult to access by existing surgical apparatuses or to perform a minimal invasive surgery. These surgical apparatuses are configured to move in various directions in the human body by including a bendable element, which are disclosed in many documents including U.S. Pat. No. 6,858,005.

Surgical apparatuses bendable at the distal end bend by the movement of wires inside them. However, these surgical apparatuses are hard to finely manipulate, revealing some problems like creating backlash when they are bent with the wires or restricting the movement of other wires. Also, these surgical apparatuses have many components embedded in them which are connected to one another in a complicated way, so it is difficult to miniaturize them.

SUMMARY

Embodiments of the present invention may provide a surgical apparatus comprising: a steerable member that is bendable and comprises a plurality of bending segments with channels therein; and a plurality of bending actuation wires that are arranged to pass through the steerable member and cause the steerable member to bend, the steerable member comprising at least one lumen through which the bending actuation wires pass, and the lumen being partially open outward.

Other embodiments of the surgical apparatus may further comprise an end effector provided at the distal end of the steerable member; and an effector actuation wire connected to the end effector to actuate the end effector, at least part of the end effector being detachably provided at the distal end of the effector actuation wire.

A wire termination member for fixing the distal ends of the bending actuation wires may be provided at the distal end of the steerable member, and the bending actuation wires may be fixed by screwing the wire termination member.

The surgical apparatus may further comprise: a flexible member comprising a flexible material that is provided at the proximal end of the steerable member and; and at least one sleeve forming a path of travel of a wire passing through the steerable member or the flexible member, both ends of which are fixed to the inside of the steerable member of flexible member.

Screw members may be provided on the bending actuation wires, respectively, and the steerable member bends as the screw members move mechanically in sync with each other.

BRIEF DESCRIPTION OF THE DRAWINGS

Hereinafter, a surgical apparatus according to exemplary embodiments of the present invention will be described concretely with reference to the drawings. A description of the positional relationship between the components will now be made basically with reference to the drawings. In the drawings, structures of the embodiments may be simplified or exaggerated for clarity. Accordingly, the present invention is not limited to these exemplary embodiments, but instead various kinds of devices may be added, changed, or omitted.

The exemplary embodiments will be described with respect to a surgical apparatus that has a plurality of passages inside an insertion part, with various kinds of surgical instruments located in each passage. However, it is to be noted that the present invention is not limited to this exemplary embodiment and is applicable to a variety of surgical apparatuses, including catheters, endoscopes, and surgical robots, that are bendable at the distal end.

FIG. 8A is an isometric view of a bending segment according to another embodiment of the present invention. FIG. 8B is an isometric view of a plurality of the bending segments of FIG. 8A.

FIG. 9A is an isometric view of a bending segment having a recess part accommodating the connecting part according to an embodiment of the present invention. FIG. 9B is an isometric view of a bending segment having a recess part with a v-shaped notch-like groove according to another embodiment of the present invention.

FIGS. 13A to 13F are views illustrating various exemplary embodiments of a steerable member having different arrangements of the bending actuation wires and lateral supporting members, wherein FIG. 13A is an isometric view of a steerable member according to a first exemplary embodiment; FIG. 13B is an isometric view of a steerable member according to a second exemplary embodiment; FIG. 13C is an isometric view of a steerable member according to a third exemplary embodiment; FIG. 13D is an isometric view of a steerable member according to a fourth exemplary embodiment; FIG. 13E is an isometric view of a steerable member according to a fifth exemplary embodiment; and FIG. 13F is an enlarged view of the lateral supporting members and the bending actuation wires of the third exemplary embodiment of FIG. 13D.

FIG. 14A is a schematic sectional view of a steerable member with a lateral supporting member in a neutral state without any manipulation. FIG. 14B is a schematic sectional view of a steerable member with a pre-shaped lateral supporting member in a state that a first tensile force F is applied to. FIG. 14C is a schematic sectional view of a steerable member with a pre-shaped lateral supporting member in a state that a second tensile force F' is applied thereto.

FIG. 16A is an isometric view illustrating a connecting segment and bending segments connected by the connecting segment. FIG. 16B is an isometric view of the connecting segment of FIG. 16A.

FIG. 17A is an isometric view of the steerable member comprising a plurality of connecting segments in a neutral state. FIG. 17B is an isometric view of the steerable member comprising a plurality of connecting segments in a bent state.

FIGS. 22A to C are isometric views illustrating a method of fixing bending actuation wires by a wire termination member, wherein FIG. 22A illustrates the wire termination member being threaded to the distal end of the steerable member; FIG. 22B illustrates bending actuation wires being fixed when the wire termination member is threaded; and FIG. 22C illustrates the steerable member after the bending actuation wires is fixed.

FIG. 33A is a schematic view showing the length of the bending actuation wire before bending in an ideal continuous flexible arm. FIG. 33B is a schematic view showing the length of the bending actuation wire after bending in an ideal continuous flexible arm.

FIG. 34A is a schematic view showing the length of the bending actuation wire before bending in the actual condition. FIG. 34B is a schematic view showing the length of the bending actuation wire after bending in the actual condition.

FIGS. 37A and B illustrate pivotal motion of one of the exemplary tension-regulating member of FIG. 36, wherein FIG. 37A is a front view of the tension-regulating member bending to the left side.

FIGS. 38A and B are schematic views illustrating a slack in a wire being improved according to the exemplary tension-regulating member structure in FIG. 36, wherein FIG. 38A shows the length of the bending actuation wire before bending.

FIG. 41 is a schematic view illustrating a surgical instrument according to an exemplary embodiment of the present invention.

FIG. 42 is a schematic view illustrating a surgical instrument in a bending motion according to an exemplary embodiment of the present invention.

FIGS. 48A-E are views illustrating three types of the interchangeable grips according to an exemplary embodiment of the present invention wherein FIG. 48A is an isometric view of a grip-type interchangeable grip connected to an inner gimbal structure, FIG. 48B is an isometric view of the interchangeable grip of FIG. 48A detached from the inner gimbal structure, FIG. 48C is an isometric view of a tweezers-type interchangeable grip connected to an inner gimbal structure, FIG. 48D is an isometric view of the interchangeable grip of FIG. 48C detached from the inner gimbal structure, FIG. 48E is an isometric view of a laparoscopic-hand-instrument type interchangeable grip connected to an inner gimbal structure, and FIG. 48F is an isometric view of the interchangeable grip of FIG. 48E detached from the inner gimbal structure.

DETAILED DESCRIPTION

Figure 1:
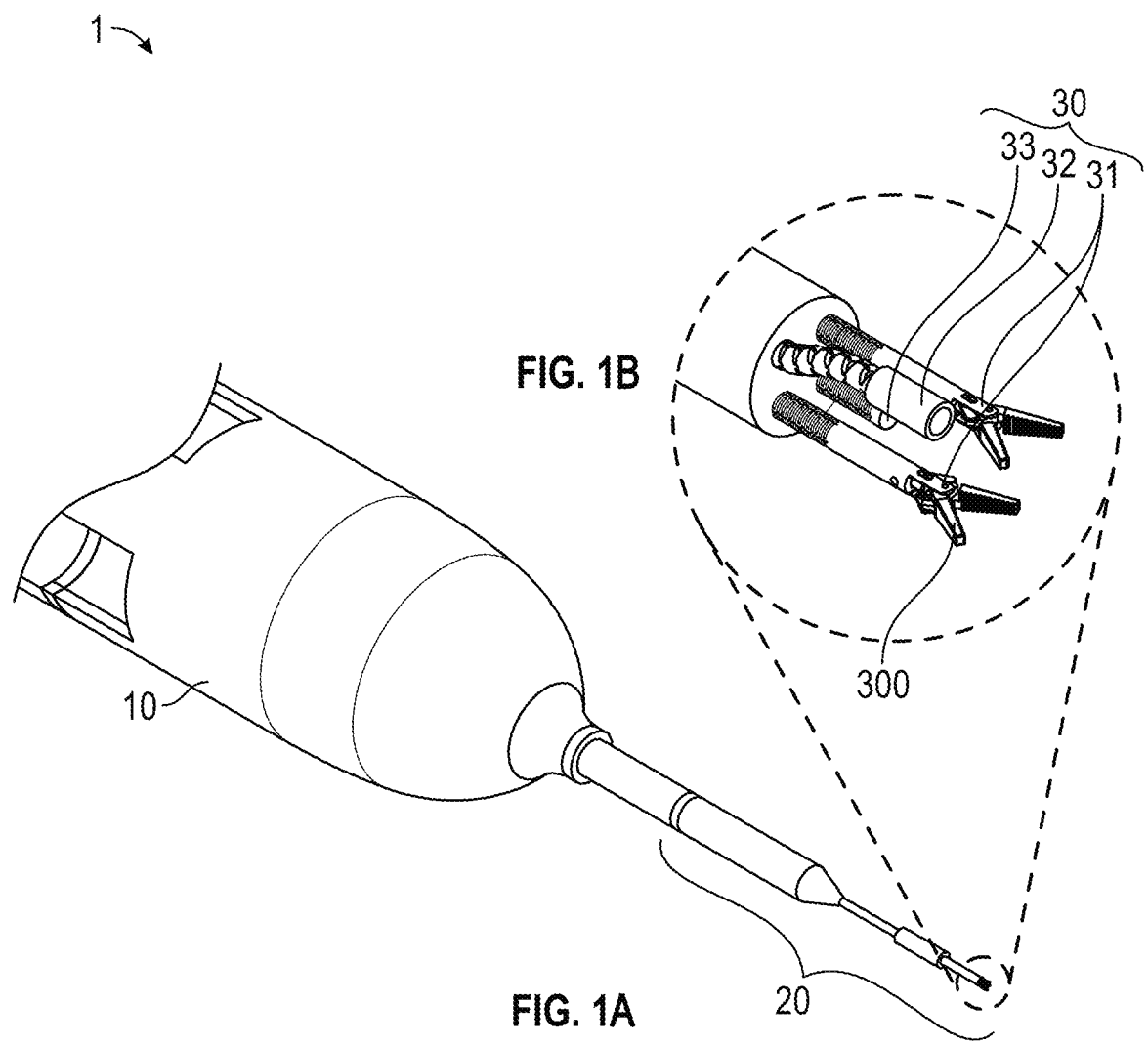
FIG. 1A is an isometric view of a distal end of the surgical apparatus including a manipulating part and an insertion part.
FIG. 1B is an enlarged isometric view of the insertion part in FIG. 1A.

The invention and the various features and advantageous details thereof are explained more fully with reference to the non-limiting embodiments that are illustrated in the accompanying drawings and detailed in the following description. Descriptions of well-known materials, manufacturing techniques, parts, and equipment are omitted so as not to unnecessarily obscure the invention in detail. It should be understood, however, that the detailed description and the specific examples, while indicating preferred embodiments of the invention, are given by way of illustration only and not by way of limitation. Various substitutions, modifications, additions and/or rearrangements within the spirit and/or scope of the underlying inventive concept will become apparent to those skilled in the art from this disclosure.

Hereinafter, a surgical apparatus according to an exemplary embodiment of the present invention will be described concretely with reference to the drawings. A description of the positional relationship between the components will now be made basically with reference to the drawings. In the drawings, structures in the embodiment may be simplified or exaggerated for clarity. Accordingly, the present invention is not limited to this exemplary embodiment, but instead various kinds of devices may be added, changed, or omitted.

This exemplary embodiment will be described with respect to a surgical apparatus that has a plurality of passages inside an insertion part, with various kinds of surgical instruments located in each passage. However, it is to be noted that the present invention is not limited to this exemplary embodiment and is applicable to a variety of surgical apparatuses, including catheters, endoscopes, and surgical robots, that are bendable at the distal end.

FIG. 1 is a view illustrating a surgical apparatus according to an exemplary embodiment of the present invention. As illustrated in FIG. 1, a surgical apparatus 1 comprises an insertion part 20 provided at the distal end of the surgical apparatus and a manipulating part 10 located at the proximal end of the insertion part 20.

The insertion part 20 forms a part that is inserted into a surgical site during surgery. The insertion part 20 consists of a flexible tube, in which at least one surgical instrument 30 for use in a surgical operation is located. The surgical instrument 30 may be selectively located in at least one hollow passage that is formed inside the insertion part 20. Alternatively, the surgical instrument 30 may be embedded in the insertion part 20. The surgical instrument 30, sticking out of the distal end of the insertion part 20, may be used in surgery or capture images of the surgical site.

The surgical apparatus of FIG. 1 comprises an insertion part 20 with four passages, each passage including four surgical instruments 30. In FIG. 1, two out of the four surgical instruments include forceps 31 as end effectors 300 at the distal end. Such surgical instruments may perform various surgical operations by manipulating the forceps. Besides, other various types of surgical elements including blades, suturing units, needles, etc. can be used. One of the remaining two surgical instruments is an imaging unit 32. The imaging unit 32 may capture images of the distal end by including an optical device such as an optical fiber. The other surgical instrument may be a lumen unit 33 with a working channel in it through which various instruments can be inserted.

These surgical instruments 30, sticking out of the distal end of the insertion part 20, are configured such that their protruding end can bend. Accordingly, the bending of the surgical instruments 30 allows for performing a surgical operation in different directions or taking images from different directions. The surgical instruments 30 may bend by the movement of a plurality of wires inside them, which will be described in detail below.

The manipulating part 10 is provided at the proximal end of the insertion part 20, and configured to manipulate the insertion part 20 and/or the surgical instruments 30. The distal end of the manipulating part 10 is connected to the proximal end of the insertion part 20, and may be detachably connected thereto in this exemplary embodiment. At least one driving part is provided in the manipulating part 10. The driving part 40 is mechanically connected to the insertion part 20 and/or various types of wire members of the surgical instruments 30, and the driving part 40 enables various motions of the insertion part 20 and/or surgical instruments 30, including bending movement of the surgical instruments 30.

Hereinafter, a detailed configuration of the above-described surgical apparatus will be explained in more detail with reference to the drawings.

Figure 2:
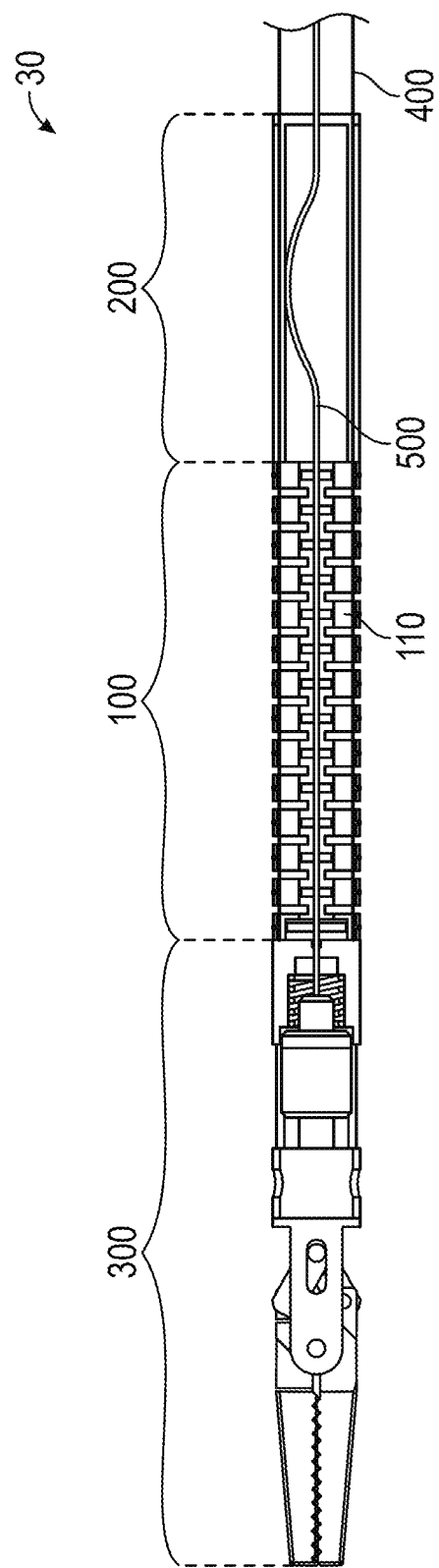
FIG. 2 is a cross-sectional view of one of the surgical instruments of FIG. 1A.

FIG. 2 is a cross-sectional view of one of the surgical instruments of FIG. 1. As illustrated in FIG. 2, the surgical instrument 30 comprises a steerable member 100 at the distal end that is bendable. The steerable member 100 has a plurality of bending segments 110 with hollow channels (not shown) that are connected together. A flexible member 200 comprising a flexible material is provided at the proximal end of the steerable member 100. The flexible member 200 may consist of a hollow tube where various types of wire members connected from the distal end of the surgical instrument 30 are located. Optionally, an end effector 300 is provided at the distal end of the steerable member 100, and the end effector 300 may be selectively actuated by an effector actuation wire 500.

Each bending segment 110 of the steerable member 100 is connected to adjacent bending segments in a way that allows hinge movement, and bent by means of bending actuation wires 400. The bending actuation wires 400 are located in such a way as to pass through the steerable member 100 and the flexible member 200, and the distal ends of the bending actuation wires 400 are connected to the steerable member 100 and their proximal ends are mechanically connected to the manipulating part 10. Each bending segment 110 comprises a plurality of lumens 112 that are formed lengthwise, and the bending actuation wires 400 are located within the lumens 112 (FIG. 5A). Accordingly, when the bending actuation wires 400 are moved by the manipulating part 10, the plurality of bending segments 110 move hingedly, thus causing the steerable member 100 to bend.

Figure 3B:
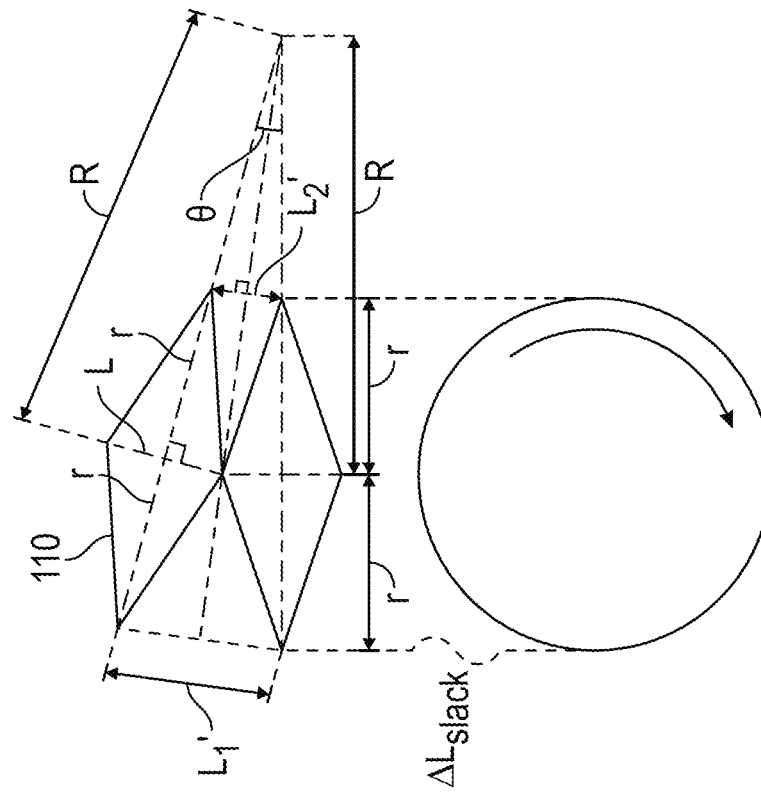
FIG. 3B is a schematic plan view of the adjacent bending segments in a bent state.
Figure 3A:
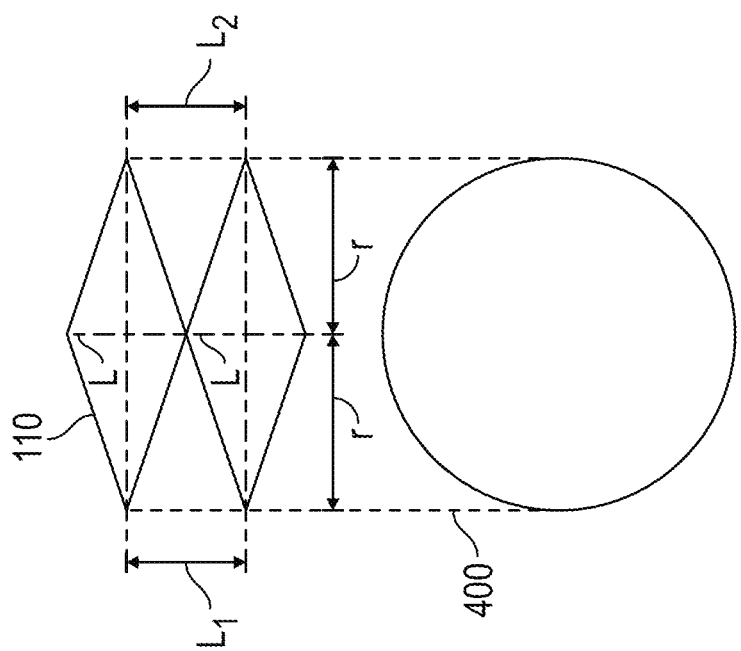
FIG. 3A is a schematic plan view of two adjacent bending segments of the steerable member in a neutral state.

FIGS. 3A and 3B are views schematically illustrating a slack in a wire due to bending of the steerable member. Let the bending segments 110 have a length of L and a width of 2r. Adjacent bending segments 110 are hinged at the middle on their facing sides (which is at a distance of r from the outer perimeter). Let the bending actuation wires 400 be located on two opposite sides of the width of each bending segment and pass through the middle of the length of each bending segment (which is at a distance of L from each hinged portion).

FIG. 3A illustrates the steerable member in a neutral state before bending, and FIG. 3B illustrates the steerable member when being bent to a radius of curvature R. In FIG. 3B, the angle of bend between two bending segments 110 is denoted by θ. The following equation is to compare the sum of the lengths of two wire portions between the two bending segments before bending and the sum of the lengths of the two wire portions after bending. If the lengths of the two wire portions before bending are denoted by $L_1$ and $L_2$, respectively, and the lengths of the two wire portions after bending are denoted by $L_1'$ and $L_2'$, respectively, the difference $\Delta L$ between the two lengths is as follows:

$$L_1 = L_2 = L = 2R\tan\left(\frac{\theta}{2}\right)$$

$$L_1' + L_2' = 2(R+r)\sin\left(\frac{\theta}{2}\right) + 2(R-r)\sin\left(\frac{\theta}{2}\right) = 4R\sin\left(\frac{\theta}{2}\right)$$

$$\Delta L = L_1 + L_2 - L_1' - L_2' = 4R\left(\tan\left(\frac{\theta}{2}\right) - \sin\left(\frac{\theta}{2}\right)\right)$$

As seen from above, the sum of the lengths of the two wire portions between the two bending segments after bending is smaller than that before bending. Accordingly, when the wires on both sides are manipulated in conjunction with each other, a slack of $\Delta L$ is produced between each bending segment. This is because, when bending occurs, the amount of change ($L_1'-L_1$) in the length of the wire on the other side of the center of curvature is smaller than the amount of change ($L_2-L_2'$) in the length of the wire near the center of curvature. Accordingly, backlash is created due to bending, thus making fine adjustment difficult.

Figure 4:
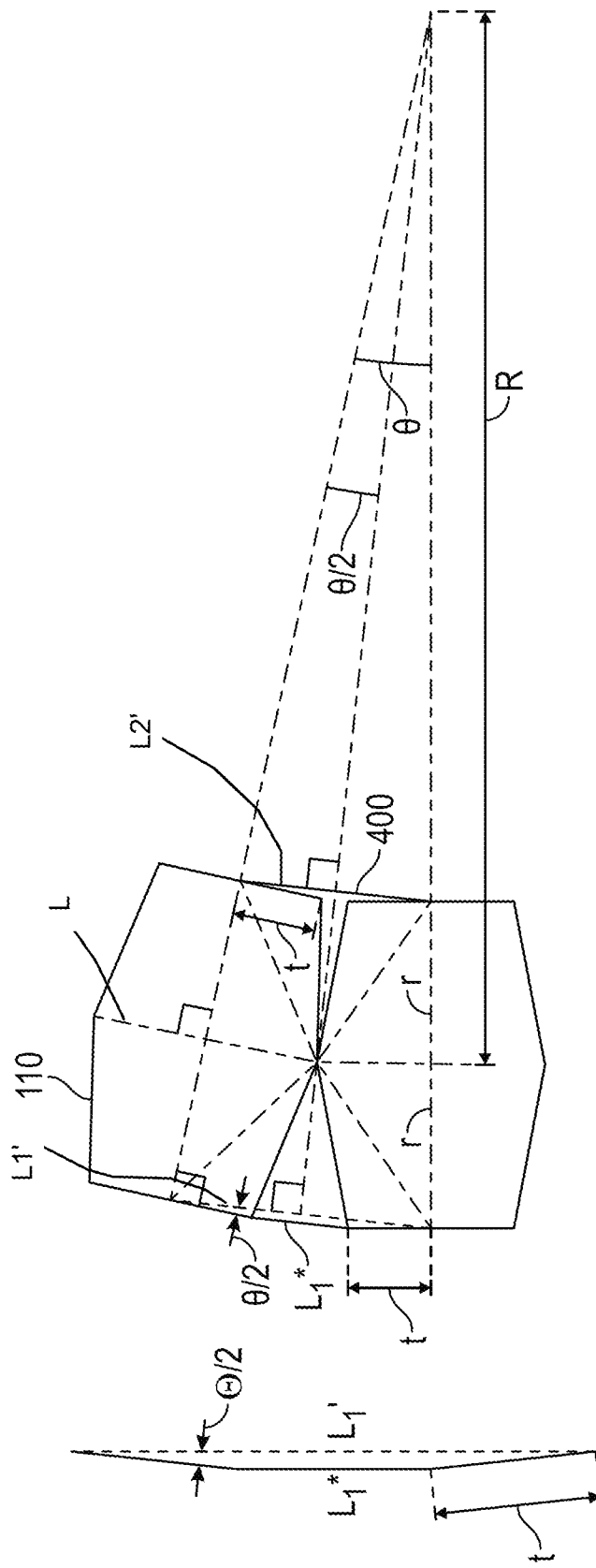
FIG. 4 is a schematic plan view illustrating a slack in a wire according to an improved bending segment structure.

In contrast, in this exemplary embodiment, the bending segments may be configured in various shapes to minimize the slack caused by bending. FIG. 4 is a view schematically illustrating a slack in a wire according to an improved bending segment structure. As illustrated in FIG. 4, the improved bending segments 110 are configured in such a way that part of the lumens 112 where the bending actuation wires are located is open (see FIG. 5). Herein, t denotes the length of an open lumen portion. While the wire near the center of curvature has the shorter path due to the open lumen portion, the wire on the other side of the center of curvature has the path to which an extra length is added at the corresponding open lumen portion. In this case, the path $L_2^*$ of the wire near the center of curvature is equal in length to the previous path ($L_2'$ of FIG. 3), and the path $L_1^*$ of the wire on the other side of the center of curvature is longer than the previous path ($L_1'$ of FIG. 3). This increase in path length is because a sidewall of the open lumen portion (near the center of the bending segments) on the other side of the center of curvature forms a stumbling portion 114 and the bending actuation wire 400 passing through the path stumbles against the stumbling portion 114 (see FIG. 5). Accordingly, when bending occurs using the improved bending segments, $\Delta L$ is as follows:

$$L_1 = L_2 = L = 2R\tan\left(\frac{\theta}{2}\right)$$

$$L_1^* = L_1' - 2t\cos\left(\frac{\theta}{2}\right) + 2t = L_1' + 2t\left(1 - \cos\left(\frac{\theta}{2}\right)\right)$$

$$L_1^* + L_2^* = 2(R+r)\sin\left(\frac{\theta}{2}\right) + 2(R-r)\sin\left(\frac{\theta}{2}\right) + 2t\left(1 - \cos\left(\frac{\theta}{2}\right)\right) = 4R\sin\left(\frac{\theta}{2}\right) + 2t\left(1 - \cos\left(\frac{\theta}{2}\right)\right)$$

$$\Delta L = L_1 + L_2 - L_1^* - L_2^* = 4R\left(\tan\left(\frac{\theta}{2}\right) - \sin\left(\frac{\theta}{2}\right)\right) - 2t\left(1 - \cos\left(\frac{\theta}{2}\right)\right)$$

As stated above, with the improved bending segments 110 configured to reduce the length ΔL of the slack, the movement of the surgical apparatus 1 can be finely controlled. Generally, the length t of the open lumen portions may be 10% or more of the length L of the bending segments. Although the amount of reduction in the length ΔL of the slack differs depending on the dimension, angle of bend, etc. of the bending segments, the length ΔL of the slack may be reduced by approximately 30% or more.

The improved bending segments may be designed in various ways. Hereinafter, various exemplary embodiments of the bending segments will be described in detail with reference to FIGS. 5 to 11.

Figure 5B:
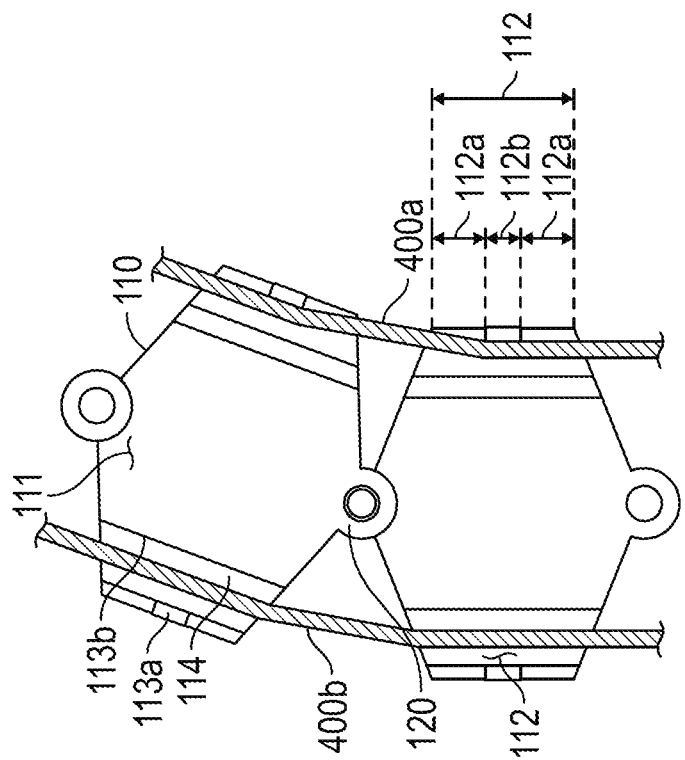
FIG. 5B is a longitudinal section view of the bending segments of FIG. 5A.
Figure 5A:
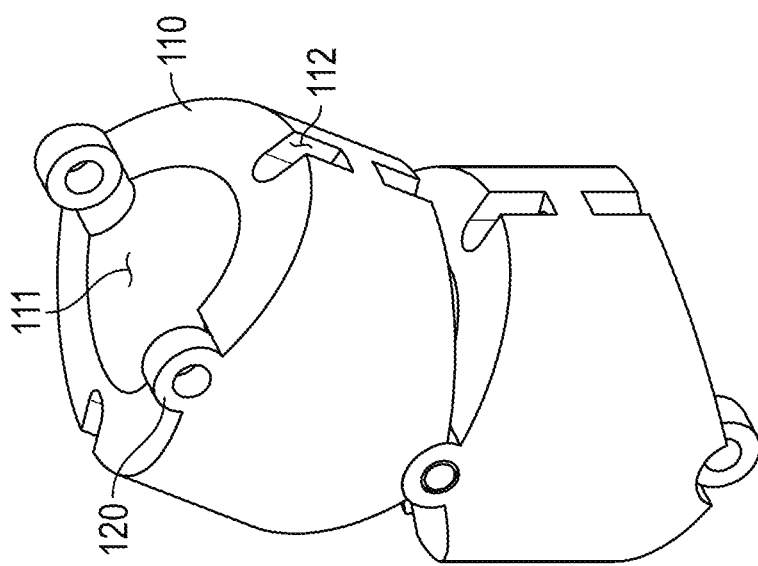
FIG. 5A is a partial isometric view of the bending segments.

FIGS. 5A and 5B are views illustrating a structure of bending segments with 1 degree of freedom. The bending segments 110 shown in FIGS. 5A and 5B have a body with hollow channels 111 formed within them. One pair of connecting parts 120 is provided on one end of the length of the body and other one pair of connecting parts 120 is provided on the opposite end. Each pair of connecting parts 120 is located facing each other on two opposite sides of the width of the body, with a hollow channel 111 midway between them.

Each bending segment 110 is hinged to adjacent bending segments, and connected to them by the connecting parts coupled to those of the adjacent ones. In FIG. 5A, the connecting parts 120 are connected by pinning them together. As hinge shafts of the connecting parts 120 all have the same orientation, the steerable member of FIG. 5B has 1 degree of freedom at which it bends to the left or right (as shown in the drawing).

Each bending segment 110 includes a pair of lumens 112 in which the bending actuation wires are located. The pair of lumens 112 may be formed by penetrating through the wall surface of a hollow body, and they are arranged symmetrically about the center of a cross-section of the bending segment 110, spaced a predetermined distance from each other.

As shown in FIGS. 5A and 5B, the lumens of the bending segments 110 are partially open. Specifically, each lumen comprises a closed lumen portion 112b and an open lumen portion 112a. In the closed lumen portion 112b, the inner and outer sides are enclosed by wall surfaces as shown in FIG. 5, so that the bending actuation wire moves only within the lumen due to the sidewall structure. In contrast, in the open lumen portion 112a, at least part of its sidewalls has an open structure. Accordingly, the bending actuation wire located in the open lumen portion 112a is movable outside the lumen through the open portion.

In this exemplary embodiment, the open lumen portion 112a has a structure in which a sidewall 113a on the outer side of the bending segment (which is on the opposite side of the center of a cross-section of the bending segment) is open. Accordingly, when bending occurs, the wire 400a near the center of curvature moves to an open portion (outward direction) of the open lumen portion, which enables the bending segments to be connected on a shorter length, as compared with the closed lumen portion. On the contrary, a sidewall 113b of the open lumen portion (near the center of the cross-section of the bending segment), if located on the other side of the center of curvature, forms a stumbling portion 114 against which a wire stumbles. Accordingly, when bending occurs, the wire 400b on the other side of the center of curvature is brought into more contact with the bending segment as it stumbles against the stumbling portion 114, thereby reducing the length of the slack.

In FIG. 5B, each lumen 112 of the bending segments 110 is configured in such a way that a closed lumen portion 112b is formed at the middle of the lumen length and an open lumen portion 112a is located on either side of the closed lumen portion 112b. This is merely an example, and one side of the lumen 112 along the length may form an open lumen portion and the other side may form a closed lumen portion. Alternatively, the open lumen portions of a pair of adjacent bending segments may be arranged symmetrically with respect to the hinge shafts. In this way, the lumens where the bending actuation wires are located may be variously altered in such a way that a wall surface (inner wall surface) 113b near the center of a cross-section of the bending segments is longer than a wall surface (outer wall surface) 113a on the other side of the center of the cross-section thereof.

Although FIG. 5B illustrates that the open lumen portion 112a is longer than the closed lumen portion 112b, the present invention is not limited thereto and may have various configurations depending on the structure of the bending segments and the angle of bend. It should be noted that the length of the open lumen portion occupying 20% or more of the entire lumen length may be advantageous to reducing the length of the slack.

Figure 6B:
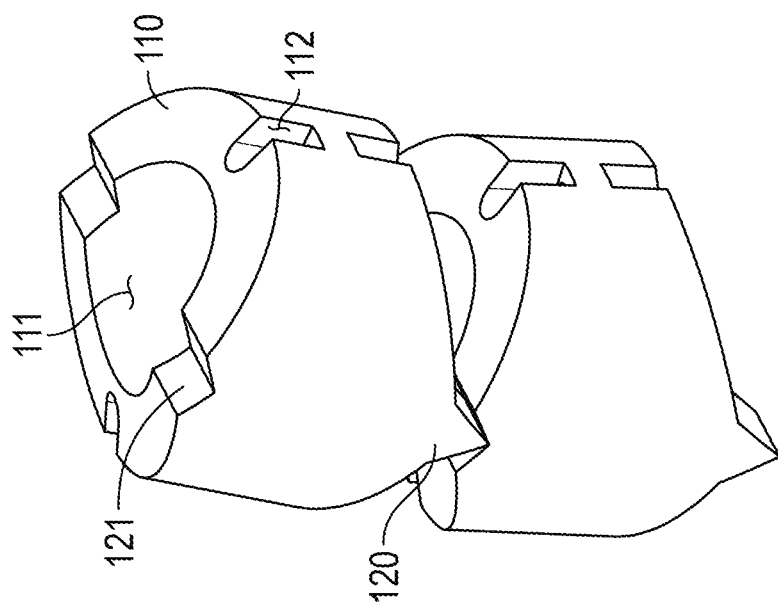
FIG. 6B is a partial isometric view of the bending segments having a protrusion with a linear edge at the end according to another embodiment of the present invention.
Figure 6A:
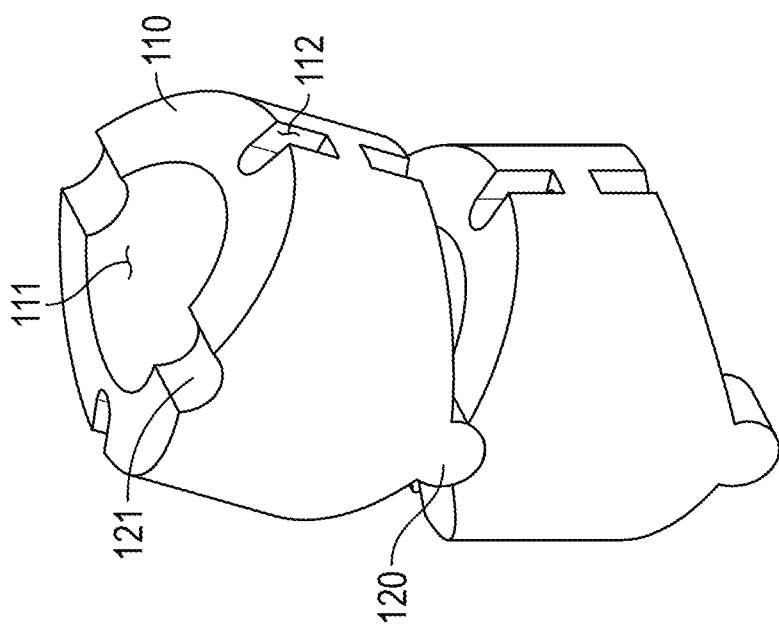
FIG. 6A is a partial isometric view of the bending segments having a protrusion with a round surface according to an embodiment of the present invention.

The connecting parts of the bending segments can be formed in various ways, other than pinning the connecting parts together as shown in FIGS. 5A and 5B. FIGS. 6A and 6B illustrate an example of a different type of connecting parts.

The bending segments of FIGS. 6A and 6B each include a pair of connecting part 120 on one side and a pair of recess parts 121 on the other side. The connecting parts 110 of a bending segment 110 are accommodated in the recess parts 121 of an adjacent bending segment and hinged to them. The connecting parts 120 of FIG. 6A each consist of a protrusion with a round surface, and the recess parts 121 each are configured to accommodate the protrusion. Accordingly, each connecting part 120 moves hingedly as it rotates within the corresponding recess part 121. The connecting parts 120 of FIG. 6B each consist of a protrusion with a linear edge at the end, and the recess parts 121 each have a v-shaped notch-like groove. Accordingly, the connecting parts 120 can move hingedly as the area of contact with the recess parts 121 rotates about the axis of rotation, while they are in linear contact with the recess parts 121.

Figure 7A:
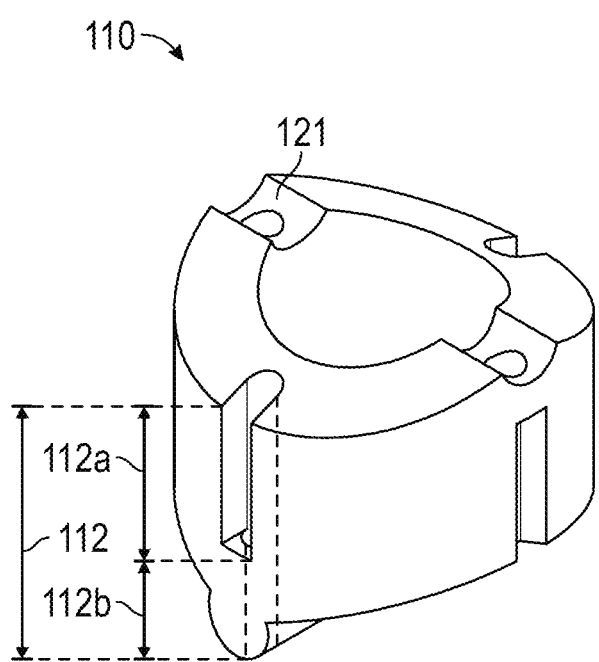
FIG. 7A is an isometric view of a bending segment of a plurality of bending segments according to one embodiment of the present invention.
Figure 7B:
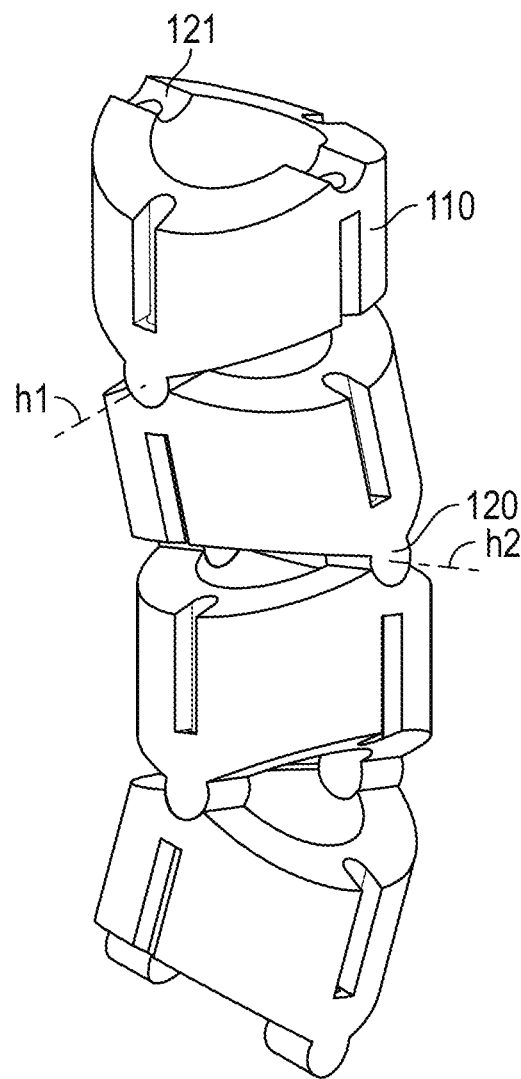
FIG. 7B is an isometric view of a plurality of bending segments of FIG. 7A.

FIGS. 7A and 7b are views illustrating a structure of bending segments with 2 degrees of freedom. The bending segments of FIG. 7B each are connected to adjacent bending segments in a way that allows hinge movement, and configured in such a way that a hinge shaft h1 connected to a bending segment on one side and a hinge shaft h2 connected to a bending segment on the other side have different orientations. Accordingly, the bending segments 100 of FIGS. 7A and 7B constitute a steerable member that is movable at 2 or more degrees of freedom, unlike in FIGS. 5 and 6.

Specifically, each bending segment 110 of FIGS. 7A and 7B includes a pair of connecting parts 120 on one side of the length and a pair of recess parts 121 on the other side. The pair of connecting parts 120 face each other with respect to the center of the bending segment 110, and the pair of recess parts 120 also do likewise. As is the case in FIG. 6A, the connecting parts 120 each consist of a protrusion with a round surface, and the recess parts 121 are configured to be rotatable and accommodate the connecting parts.

As illustrated in FIG. 7B, in each bending segment 110, a shaft that joins the pair of connecting parts 120 and a shaft that runs between the pair of recess parts 121 are orthogonal to each other. That is, the pair of connecting parts and the pair of recess parts are positioned at different locations with respect to a cross-section of the bending segment 110 (more specifically, the pair of connecting parts and the pair of recess parts intersect at 90 degrees around the body).

Hence, the bending segment 110 moves hingedly with respect to an adjacent segment on one side on a first shaft h1 and with respect to an adjacent segment on the other side on a second shaft h2. That is, the connecting parts of the bending segments are configured in such a way that the first hinge shaft and the second hinge shaft are arranged in an alternating fashion. Accordingly, the bending segments of FIG. 7 may move at 2 degrees of freedom.

Each bending segment comprises four lumens that are formed along the length. As illustrated in FIG. 7B, each lumen 112 is arranged to penetrate a connecting part 120 or a recess part 121. Accordingly, the four lumens are positioned at locations where the connecting parts and the recess parts are formed, spaced at 90-degree intervals around the body.

Four bending actuation wires 400 are located in the four lumens 112, respectively. Among them, one pair of wires induces bending of one shaft of the steerable member, and the other pair of wires induces bending of the other shaft.

Each lumen is partially open, as is with the aforementioned example. As illustrated in FIG. 7A, a portion of each lumen 112 along the length where a connecting part 120 or recess part 121 is formed forms a closed lumen portion 112b, and the other portion where the connecting part 120 or recess part 121 is not formed forms an open lumen portion 112a. Needlessly to say, the closed lumen portion may be centered on each lumen, and the open lumen portion may be positioned on either side of the closed lumen portion. Nevertheless, the configuration shown in FIG. 7 offers the advantage of further reducing the length of the slack.

Besides, although FIG. 7B illustrates that the lumen 112 penetrates the connecting part 120 or recess part 121, the lumen 112 may be diverted from the connecting part 120 and the recess part 121. Specifically, the connecting parts 120 and the recess parts 121 may be spaced at 90-degree intervals around the lateral side of the body (e.g., along the circumference) of the bending segment 110. Each lumen 112 may be located between the connecting part 120 and the recess part 121, especially at a point where it is at 45 degrees to the connecting part 120 and the recess part 121.

In this case, as illustrated in FIGS. 8A and 8B, each lumen 112 may be configured in such a way that a closed lumen portion 112b is formed at the middle of the length of the lumen and an open lumen portion 112a is formed on either side of the closed lumen portion 112b.

FIGS. 7 and 8 have been explained with respect to a connecting part 120 consisting of a protrusion with a round surface and a recess part 121 accommodating the connecting part 120. However, this is merely an example, and as shown in FIG. 6B, the connecting part may consist of a protrusion with a linear edge and the recess part may have a v-shaped notch-like groove (see FIGS. 9A and 9B). Otherwise, as shown in FIGS. 5A and 5B, two connecting parts may be pinned together in a way that allows hinge movement, rather than each comprising the connecting part and the recess part.

The exemplary embodiments shown in FIGS. 7 to 9 involve a connecting structure for rotation with respect to one shaft, in which a pair of connecting parts is provided at one bending segment and a pair of recess parts is provided at another bending segment. Besides, one connecting part and one recess part may be located on one end of one bending segment to face each other with a hollow body between them, and the connecting part and recess part of an adjacent bending segment may be located the other way round, taking into account the layout of the connecting part and recess part of the bending segment connected to the adjacent bending segment.

Figure 10:
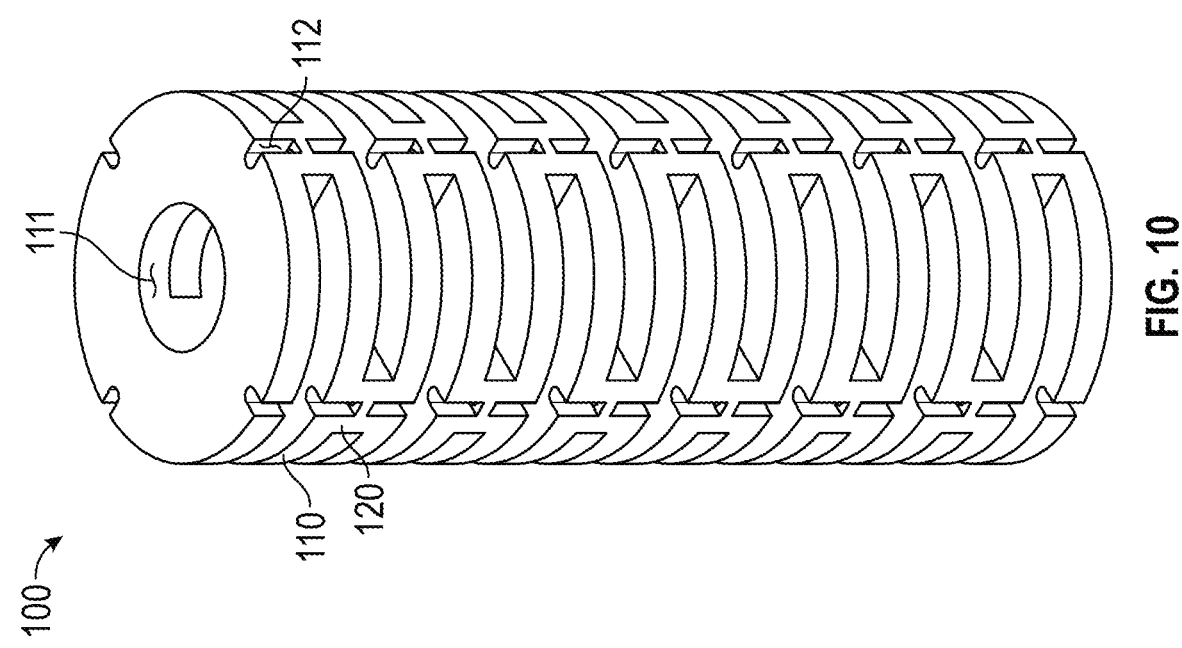
FIG. 10 is an isometric view of a steerable member using a flexible hinge structure.

FIG. 10 is a view illustrating a steerable member using a flexible hinge structure. As illustrated in FIG. 10, the bending segments 110 are in the shape of a disc-like plate, and connected by flexible connecting parts 120 situated between the bending segments 110. While the steerable member of FIGS. 5 to 9 can be bent using a mechanical hinge structure of the connecting parts, the steerable member of FIG. 10 can be bent using the elasticity of the material of the connecting parts.

More specifically, the steerable member of FIG. 10 consists of a plurality of bending segments 110 formed integrally with one another and a plurality of connecting parts 120. For example, it may be manufactured by a molding method using plastic resin with flexibility. As illustrated in FIG. 10, each bending segment 110 and each connecting part 120 have a hollow channel 111 inside them. The connecting parts 120 are provided between each bending segment 110, and have a wall structure that extends in an outer radial direction from two opposite sides of the hollow channel. A connecting part 120 (wall structure) is arranged in a direction perpendicular to the direction in which an adjacent connecting part is arranged. Accordingly, the steerable member of FIG. 10 may bend at 2 degrees of freedom.

Four lumens 112 where bending actuation wires 400 are located are arranged at 90-degree intervals. Each lumen 112 is formed at a point where it penetrates the outer edge of a connecting part 120. In this instance, as in the foregoing exemplary embodiment, each lumen 112 is a partially open lumen portion 112. As illustrated in FIG. 5B, the closed lumen portion 112b of each lumen is formed at a point where it penetrates the connecting part and the open lumen portion 112a thereof is formed on either side of the closed lumen portion 112b where the bending segment is penetrated. Accordingly, the steerable member 100 of this exemplary embodiment may bend on the connecting parts 120 as the bending actuation wires 400 move.

Figure 11:
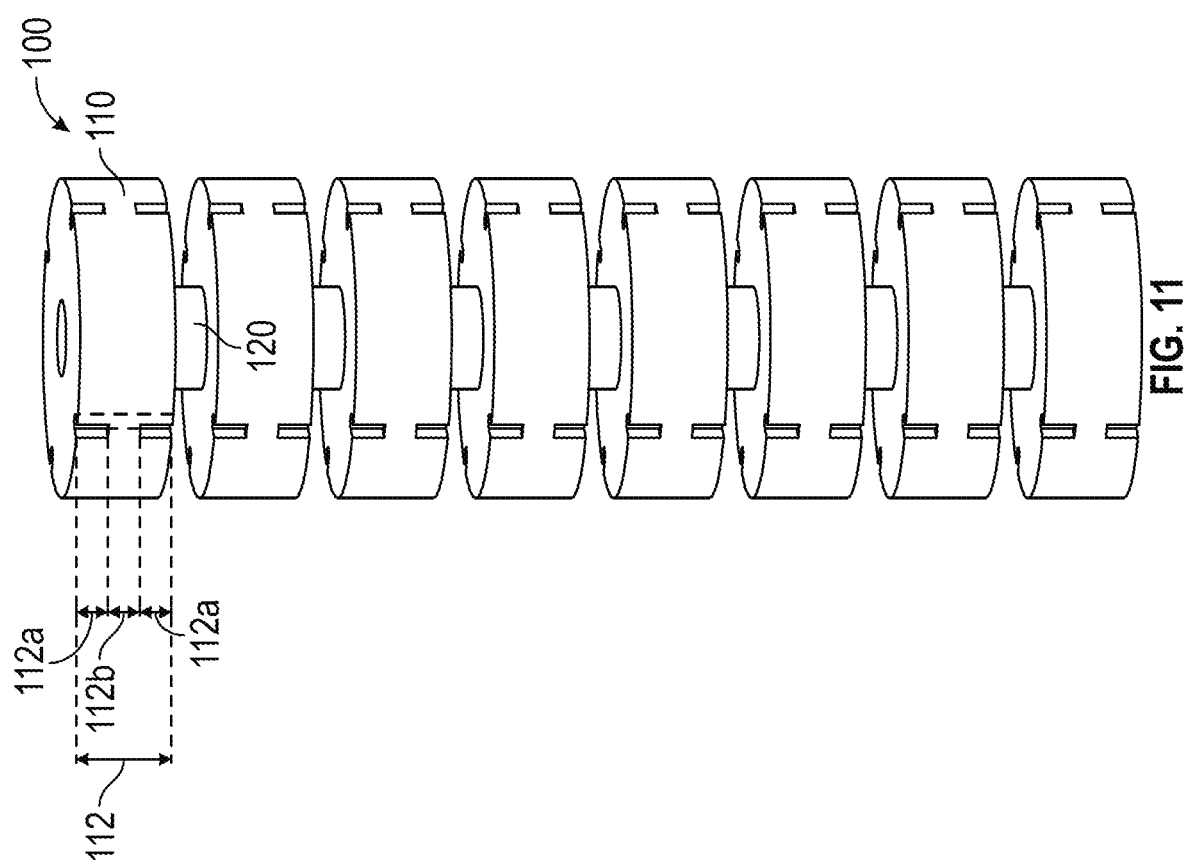
FIG. 11 is an isometric view of a steerable member using a flexible backbone structure.

FIG. 11 is a view illustrating a steerable member using a flexible backbone structure. The steerable member 100 of FIG. 11 comprises bending segments 110 each consisting of a disc-like plate and connecting parts 120 using a backbone structure for connecting the centers of the bending segments. The connecting parts 120 may consist of individual members provided between each bending segment, or may consist of a single member that penetrates through a plurality of bending segments. In this case, the connecting parts 120 may comprise a flexible material, and may bend when the bending actuation wires 400 move.

The steerable member of FIG. 10 also includes four lumens 112, and each lumen is partially open. Specifically, the lumen 112 may include a closed lumen portion 112b formed at the middle part of the length of the lumen and an open lumen portion 112a formed on either side of the closed lumen portion 112b.

In the exemplary embodiments set forth above, bending segments capable of minimizing slack are used to prevent backlash caused by bending. The steerable member may be configured in other various ways in order to prevent backlash.

FIGS. 12 to 14 are views illustrating a steerable member with a lateral supporting member 130. The lateral supporting member 130 comprises an elastic material or super-elastic material, and exerts a restoration force for returning to the original shape when its shape is deformed. That is, this steerable member may include at least one lateral supporting member within it, and may be configured to restore the elasticity of the lateral supporting member to the initial position when it is bent.

Figure 12A:
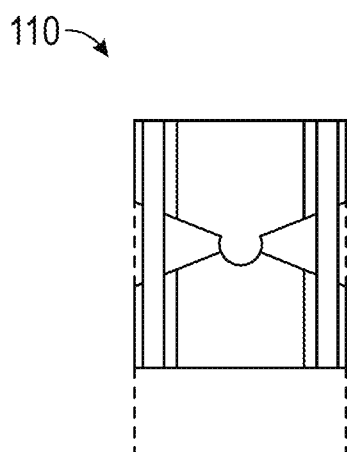
FIG. 12A is a schematic sectional view of a bending segment in a neutral state.
Figure 12B:
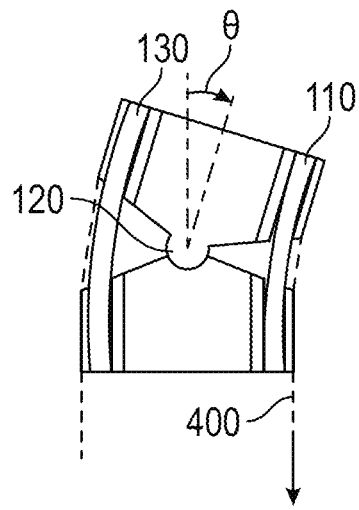
FIG. 12B is a schematic sectional view of the bending segment of FIG. 12A in a bent state.
Figure 12C:
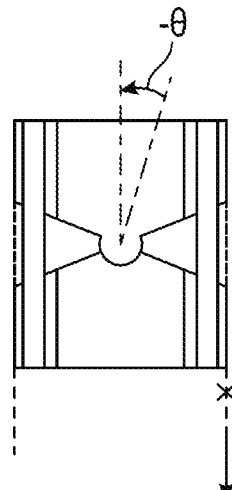
FIG. 12C is a schematic sectional view of the bending segment of FIG. 12B returning to a neutral state.

FIGS. 12A to 12C are views illustrating bending properties provided by a lateral supporting member. As illustrated in FIG. 12, if at least one bending actuation wire 400 is pulled by manipulating the manipulating part, the steerable member 100 bends in the corresponding direction. In this case, the steerable member 100 comprises at least one lateral supporting member 130, and the bending actuation wire 400 is manipulated to cause bending by overcoming the elasticity of the lateral supporting member 130 (FIG. 12B). Afterwards, when the corresponding bending actuation wire is released from being pulled (FIG. 12C), the steerable member 100 returns to neutral by the elasticity of the lateral supporting member 130.

Conventionally, while the bending actuation wire on one side is manipulated to bend in one direction, the bending actuation wire on the other side is manipulated to return to neutral. Accordingly, a slack occurs due to the bending, causing backlash. However, with the use of the lateral supporting member as shown in FIGS. 12A to 12C, the backlash caused by the slack in the bending actuation wire may not be a problem during the bending.

FIGS. 13A to 13E are views illustrating various exemplary embodiments of a steerable member using lateral supporting members. As illustrated in FIGS. 13A to 13E, the steerable member 100 may comprise a plurality of bending actuation wires 400 and a plurality of lateral supporting members 130. The lateral supporting members 130 may be configured in various types of structures, such as a wire structure or a hollow tube structure, that can function as lateral springs. The bending segments 110 of the steerable member 100 are configured to bend at 2 degrees of freedom, and may comprise a plurality of lumens 112 for allowing the bending actuation wires 400 and the lateral supporting members 130 to pass through them along the wall surface of the body.

Figure 13A:
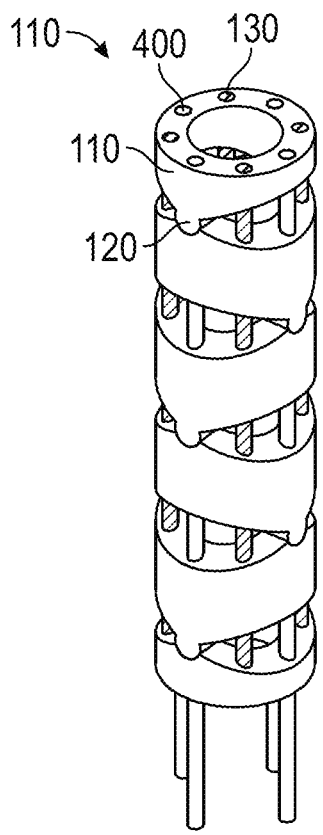
Figure 13B:
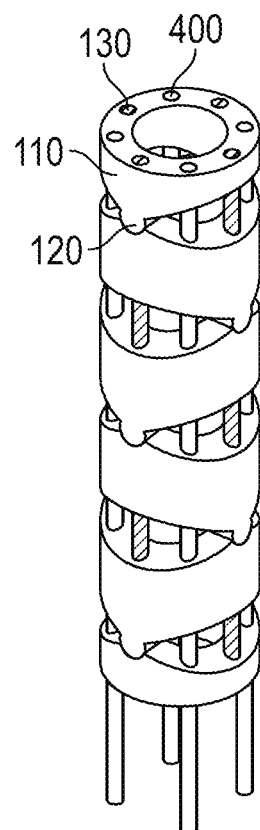
Figure 13C:
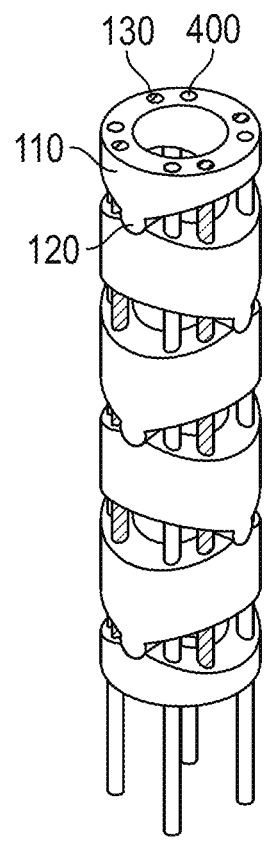

In FIGS. 13A to 13C, a plurality of bending actuation wires 400 and a plurality of lateral supporting members 130 are placed separately. In FIGS. 13A and 13B, four bending actuation wires 400 are arranged at 90-degree intervals around the body of the bending segments 110, and four lateral supporting members 130 are arranged at 45-degree intervals between each bending actuation wire 400. In this case, as shown in FIG. 13A, the four bending actuation wires 400 may be arranged to pass through the connecting parts 120 of the bending segments, and as shown in FIG. 13B, the four lateral supporting members 130 may be arranged to pass through the connecting parts 120 of the bending segments 110. Alternatively, as shown in FIG. 13C, a bending actuation wire 400 and a lateral supporting member 130 may be arranged as a pair between each connecting part location along the circumference, so as not to pass through the connecting parts of the bending segments 110.

Figure 13D:
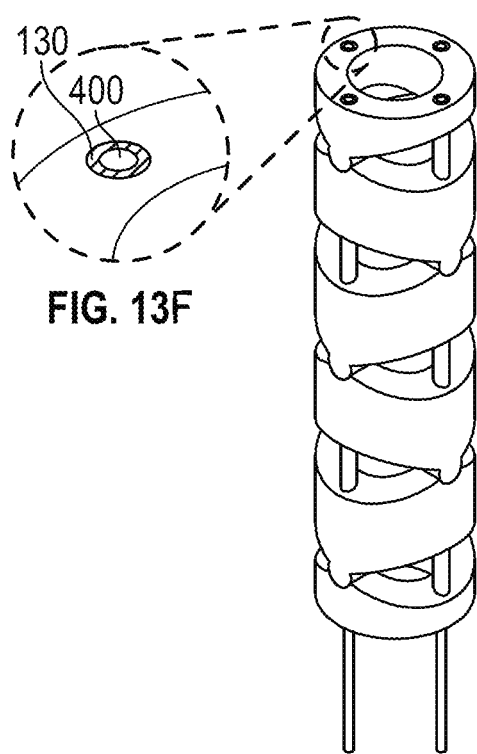
Figure 13E:
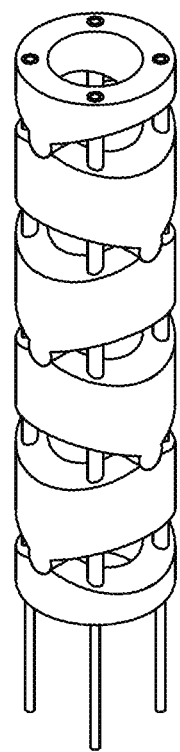

In FIGS. 13D and 13E, the lateral supporting members 130 have a hollow tube structure, and the bending actuation wires 400 are located inside the lateral supporting members 130, respectively. The lateral supporting members 130 and the bending actuation wires 400 may be arranged at 90-degree intervals around the body of the bending segments 110. In FIG. 13D, the lateral supporting members 130 and the bending actuation wires 400 are arranged to pass through the connecting parts of the bending segments. In FIG. 13E, the lateral supporting members 130 and the bending actuation wires 400 are located between each connecting part location so as not to pass through the connecting parts.

Figures 14A, 14B, 14C:
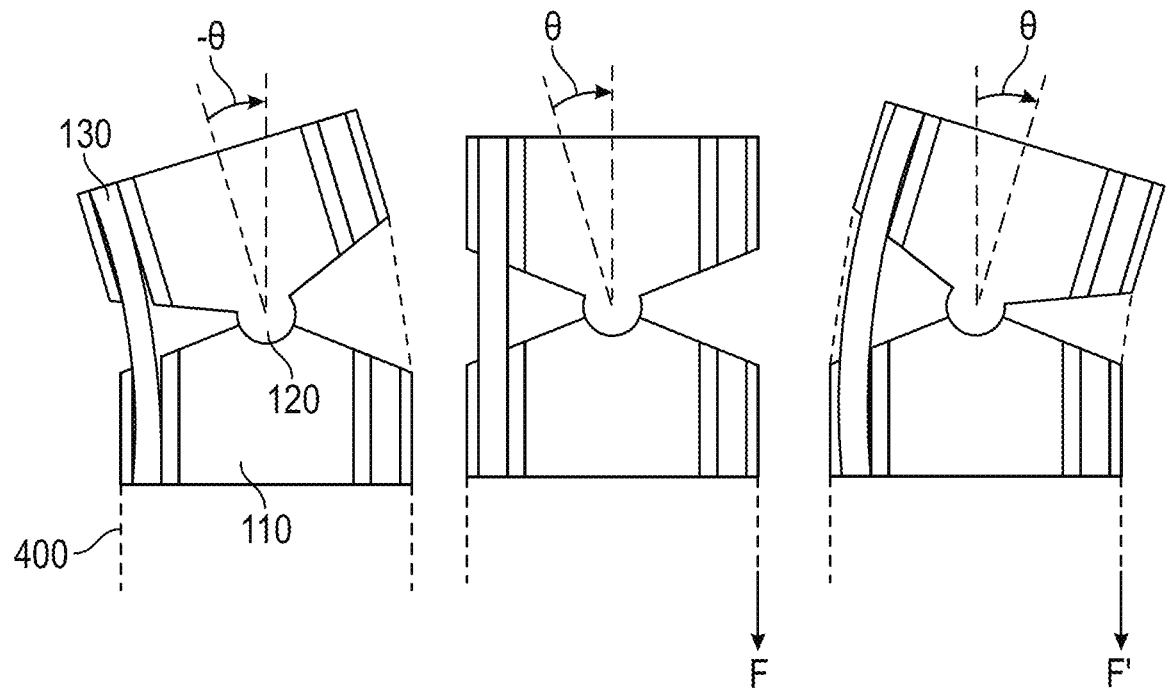

FIGS. 14A to 14C are views illustrating bending properties provided by a pre-shaped lateral supporting member. The lateral supporting members of FIGS. 12 and 13 have a shape corresponding to the neutral position of the steerable member. Accordingly, the steerable member is configured to be bent with the bending actuation wires and to return to neutral by the lateral supporting members. In contrast, the lateral supporting member 130 of FIG. 14 is configured to have a bent shape in one direction so that the elasticity of the lateral supporting member 130 contributes to bending of the steerable member to one side.

In an example, the lateral supporting member 130 of FIGS. 14A to 14C is pre-shaped to bend to the left. The steerable member with the lateral supporting member 130 in it remains bent to the left without any manipulation using the bending actuation wire (FIG. 14A). Also, if the bending actuation wire 400 moves by a first tensile force F, the steerable member can be placed in the neutral position (FIG. 14B). The first tensile force is large enough to be in equilibrium with a moment created by the elasticity of the lateral supporting member 130. If the bending actuation wire 400 moves by a second tensile force F', which is larger than the first tensile force, the steerable member can bend to the right (FIG. 14C). In this case, if the tensile force exerted on the bending actuation wire 400 is released by the first tensile force, the steerable member can move to neutral (FIG. 14B), or if the tensile force exerted on the bending actuation wires is completely released, the steerable member can bend to the left (FIG. 14A).

In this instance, the steerable member moves to the neutral position or the initial position by the elasticity of the lateral supporting member, thereby enabling bending control without backlash. Although FIG. 14 depicts a bending mechanism that has 1 degree of freedom using a pre-shaped lateral supporting member and bending actuation wires, a variety of bending mechanisms using a pre-shaped lateral supporting member may be used.

In addition, a bending mechanism using connecting segments that causes no backlash, as well as the above-mentioned method using a lateral supporting member, may be used, as shown in FIGS. 15 to 17.

Figures 15A, 15B:
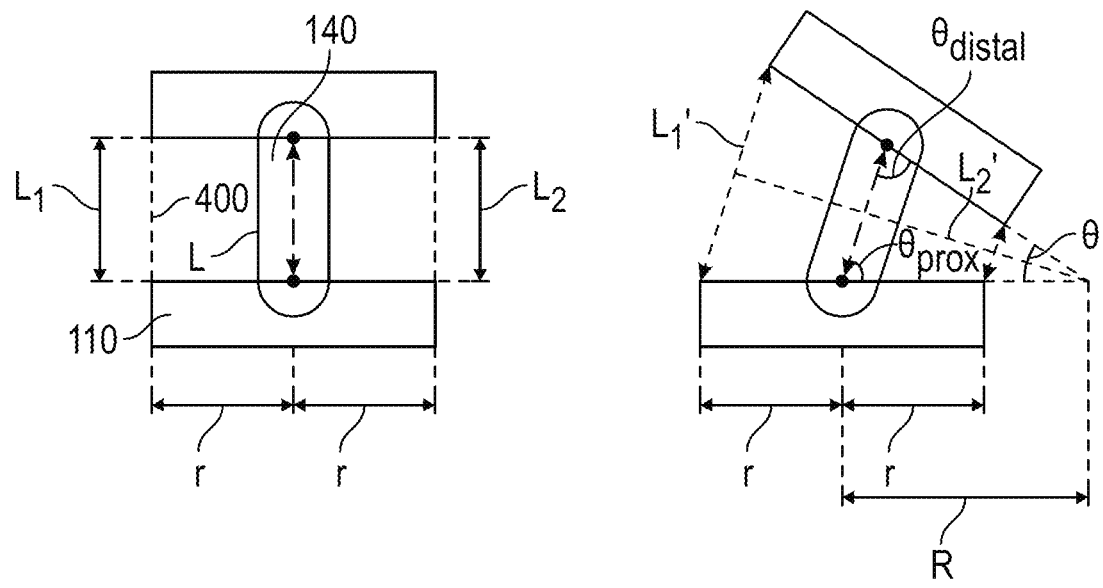
FIG. 15A is a schematic view of the adjacent bending segment before bending.
FIG. 15B is a schematic view of the adjacent bending segment when being bent to a radius of curvature R.

FIGS. 15A and 15B are views illustrating a wire path difference caused by bending of bending segments connected by connecting segments. In the foregoing exemplary embodiment (e.g., in FIGS. 3 to 9), each bending segment 110 may be coupled directly to adjacent bending segments by the connecting parts 120 provided in the body, and rotate relative to one hinge shaft shared between each pair of adjacent bending segments. In contrast, as shown in FIG. 15, a connecting segment 140 is provided between each pair of adjacent bending segments 110, and two adjacent bending segments are connected to two ends of the connecting segment 140, respectively. The connecting segment 140 has a double hinge joint structure that enables two points on the connecting segment 140 to be hinged to two different members. Accordingly, a pair of adjacent bending segments 110 is coupled to two ends of the connecting segments, respectively, so as to rotate relative to different hinge shafts, without sharing a hinge shaft.

Let the distance between the wires on either side of a bending segment 110 be 2r and let the distance between two hinge shafts of the connecting segment be L. The bending segment 110 may be hinged to the connecting segment 140, at a point midway between a pair of wires (i.e., at a distance of r from each wire).

FIG. 15A illustrates the adjacent bending segment before bending, and FIG. 15B illustrates the adjacent bending segment when bent to a radius of curvature R. In B of FIG. 15, the angle of bend between two bending segments 110 is denoted by θ. Also, it can be assumed that the angles θprox and θdistal of bend between the bending segments and the connecting segment created by bending are equal. In this case, the following equation is to compare the sum of the lengths of two wire portions between the two bending segments before bending and the sum of the lengths of the two wire portions after bending. The lengths of the two wire portions before bending are denoted by $L_1$ and $L_2$, respectively, and the lengths of the two wire portions after bending are denoted by $L_1'$ and $L_2'$, respectively.

$$L_1 = L_2 = L$$
$$L_1' = 2(R+r)\sin\left(\frac{\theta}{2}\right)$$
$$L = 2R\sin\left(\frac{\theta}{2}\right)$$
$$L_2' = 2(R-r)\sin\left(\frac{\theta}{2}\right)$$
$$L_1 + L_2 = 2L = 4R\sin\left(\frac{\theta}{2}\right)$$
$$L_1' + L_2' = 2(R+r)\sin\left(\frac{\theta}{2}\right) + 2(R-r)\sin\left(\frac{\theta}{2}\right) = 4R\sin\left(\frac{\theta}{2}\right) L_1 + L_2 = L_1' + L_2'$$

That is, if the steerable member 100 connected by the connecting segment 140 is bent, the sum ($L_1$-$L_2$) of the lengths of the two wire portions before bending and the sum ($L_1'$-$L_2'$) of the lengths of the two wire portions after bending are substantially equal. Accordingly, any slack caused by bending can be prevented.

Needless to say, FIGS. 15A and B assumes that the angles θprox and θdistal of bend between the bending segments 140 and the connecting segment 110 are equal because bending occurs at each bending segment due to the same wire. However, when actual bending occurs, the angles of bend between the connecting segment 140 and the bending segments 110 are within a substantially similar range although they are slightly different. Thus, the length of slack can be minimized as compared to the structure in which two bending segments are coupled together on a single hinge shaft.

FIGS. 16A and B are perspective views illustrating a connecting segment and bending segments connected by the connecting segment. FIGS. 17A and B are perspective views illustrating a steerable member comprising connecting segments.

As illustrated in FIG. 16A, a connecting segment 140 is hinged to a first bending segment 110a and a second bending segment 110b at different points. The connecting segment 140 comprises two bodies 141 facing each other. Each body 141 includes a first hinge part 142a on one end of its length and a second hinge part 142b on the other end (see FIG. 16B). The first and second bending segments 110a and 110b are coupled to the first and second hinge parts 142a and 142b, respectively, so that they move hingedly on different hinge shafts.

In FIG. 16, the first hinge part 142a and the second hinge part 142b each consist of a protrusion with a round surface, and are accommodated in recess parts 121b formed in the bending segments 110 and move hingedly. However, this is merely an example, and at least one of the first and second hinge parts may be a recess part for accommodating the protrusion or may be connected by other hinge structures such as pinning.

The connecting segment 140 further comprises a guide member 143 with a hollow space inside it that joins together the two bodies 141 facing each other. Due to this, the connecting segment 130 may form a module. The hollow space of the guide member 143 allows various kinds of wire members such as the bending actuation wires or the effector actuation wire to pass through, and prevents internal components from falling out during bending. A cross-section of the guide member 143 may be similar to a cross-section of the bending segments. In this case, portions through which the bending actuation wires pass may be open so as not to restrict the movement of the bending actuation wires.

The steerable member of FIGS. 17A and 17B comprises a plurality of connecting segments 140, and adjacent connecting segments 140 are configured to have hinge shafts orthogonal to each other. Each bending segment 110 has four lumens 112 so that four bending actuation wires 400 are respectively located in them. Therefore, the steerable member 100 can bend at 2 degrees of freedom (see FIG. 17B). In this case, the bending actuation wires 400 may be located between each hinge shaft location around the body of the bending segments 110 so as not to pass through the hinge shafts of the connecting segments 140.

Figure 18B:
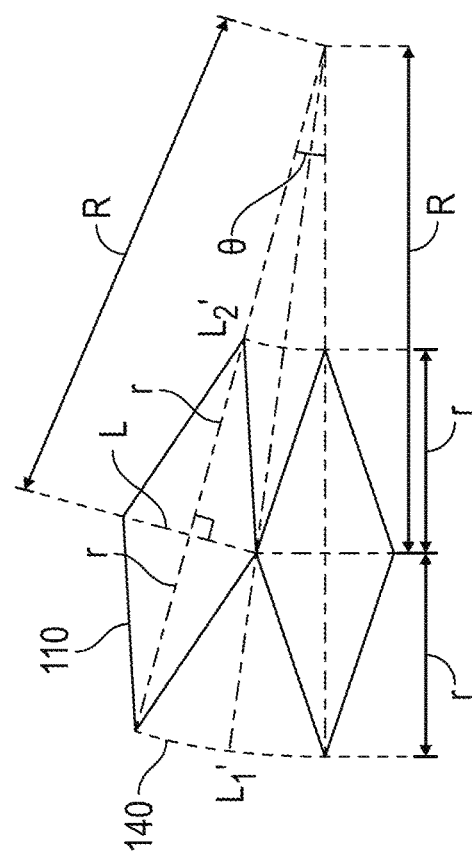
FIG. 18B is a schematic plan view of the adjacent bending segments of FIG. 18A in a bent state.
Figure 18A:
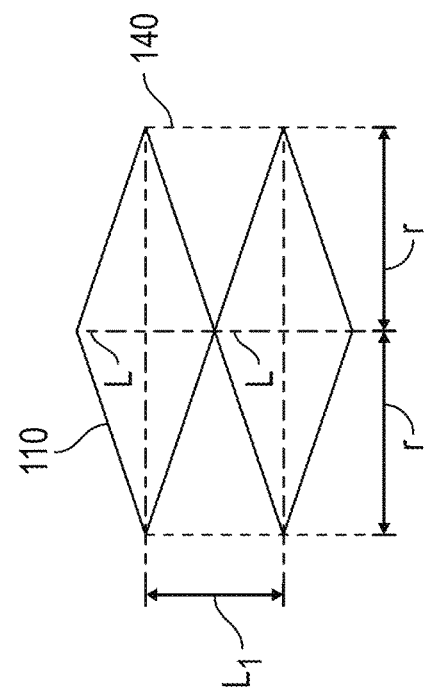
FIG. 18A is a schematic plan view of two adjacent bending segments of a steerable member having a path adjusting member in a neutral state.

In another exemplary embodiment, FIGS. 18A and 18B are views schematically illustrating a slack in a wire that forms a curved path due to bending of the steerable member. While FIGS. 3A and 3B depict a wire that forms a bent straight-line path when bending occurs, FIGS. 18A and 18B depict a wire that forms a curved path when bending occurs. If the lengths of two wire portions before bending are denoted by $L_1$ and $L_2$, respectively, and the lengths of the two wire portions after bending are denoted by $L_1'$ and $L_2'$, respectively, the relationship between the lengths of the two wire portions is as follows:

$$L_1 + L_2 = 4R\tan\left(\frac{\theta}{2}\right)$$
$$L_1' + L_2' = (R+r)\theta + (R-r)\theta = 2R\theta$$
$$\Delta L_{slack} = (L_1 + L_2) - (L_1' + L_2') = 4R\left(\tan\left(\frac{\theta}{2}\right) - \frac{\theta}{2}\right) > 0$$
$$[\Delta L_{slack} < \Delta L_{Fig3} = 4R(\tan(\theta/2) - \sin(\theta/2))]$$

As compared with the wire of FIG. 3 that forms a bent straight-line path when bending occurs, the wire of FIG. 18B that forms a curved path can have an approximately 30% reduction in the length of the slack. Using this principle, the bending actuation wires are configured to form a curved path when bending occurs by including a path adjusting member, thereby minimizing the slack.

Figure 19A:
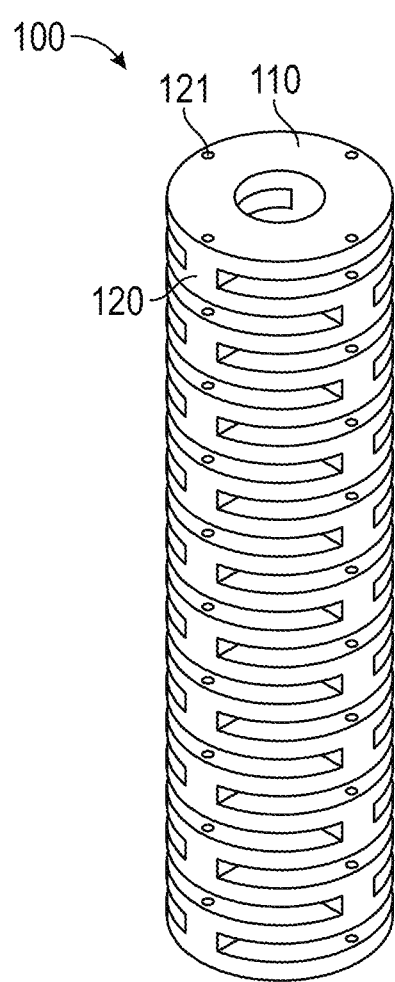
FIG. 19A is an isometric view of the steerable member comprising plate-like bending segments and wall-like connecting parts.
Figure 19B:
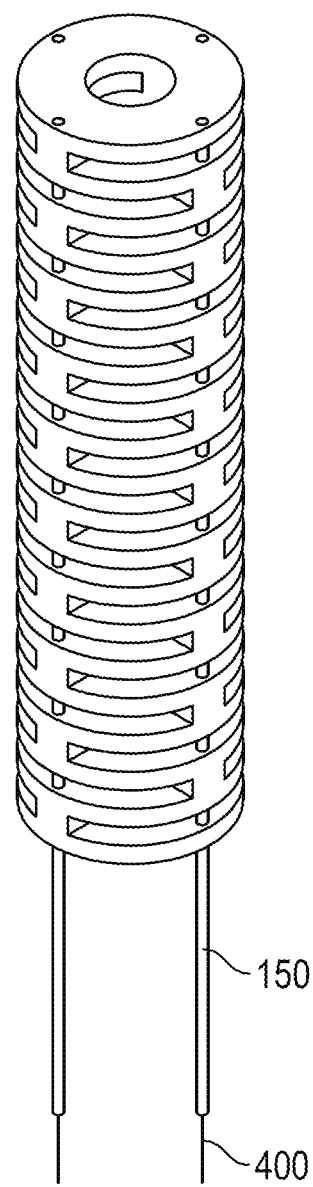
FIG. 19B is an isometric view of the steerable member of FIG. 19A with the bending actuation wires located inside the path adjusting member in each lumen.

FIGS. 19A and 19B are views illustrating a steerable member using a path adjusting member. As illustrated in FIG. 19A, the steerable member 100 comprises plate-like bending segments 110 and wall-like connecting parts 120 located between the bending segments. Also, four lumens 112 are formed to penetrate the outer edges of the bending segments 100 and connecting parts 120 (refer to the description of FIG. 10).

As illustrated in FIG. 19B, bending actuation wires 400 are located inside the path adjusting member 150 in each lumen, rather than being located directly in each lumen. The path adjusting member 150 comprises an elastic material such as metal, and bends when the steerable member 100 is bent, thereby forming a curved wire path (in this case, the elasticity of the path adjusting member does not need to be high enough to produce a restoration force as shown in FIGS. 13D and 13E, and an elastic force sufficient to form a curved path will do). Accordingly, the bending actuation wires 400 according to this exemplary embodiment bend not along a bent straight-line path but along a curved path, thereby minimizing the length of the slack.

While this exemplary embodiment has been described with respect to an example in which the path adjusting member is used for the steerable member using a flexible hinge structure, modifications may be made, like placing wires in the steerable member shown in FIGS. 11 to 17 with the use of the path adjusting member.

Figure 20B:
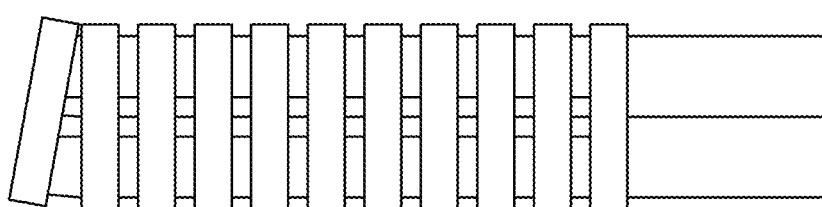
FIG. 20B is a cross-sectional view of the steerable member of FIG. 20A where the bending is concentrated at the distal end of the steerable member.
Figure 20A:
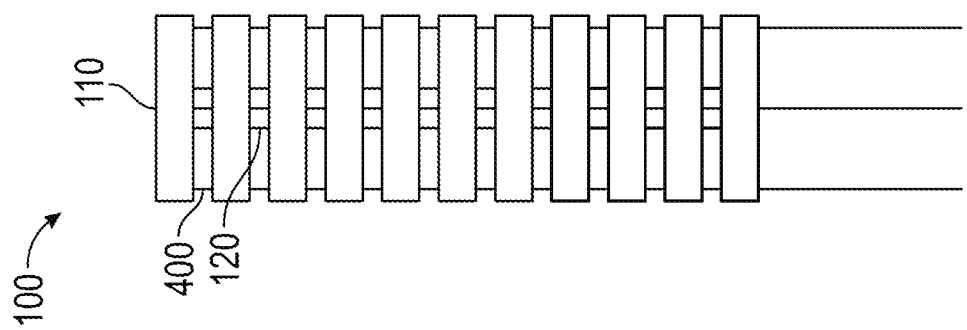
FIG. 20A is a cross-sectional view of the steerable member in a neutral state.

FIGS. 20A and 20B are views illustrating bending of the steerable member. As illustrated in FIG. 20A, at the initial stage of the bending, the bending is not uniform across the entire steerable member 100, but it is concentrated at the distal end of the steerable member where the bending actuation wire 300 ends (see FIG. 20B). Thus, a force is transmitted directly to the distal end of the steerable member when the wire moves, causing the steerable member to bend less at the proximal end.

Figure 21C:
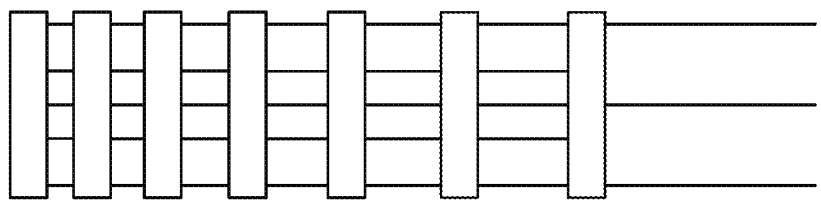
FIG. 21C is a cross-sectional view of the steerable member comprising a geometrically enhanced structure according to yet another exemplary embodiment of the present invention.
Figure 21B:
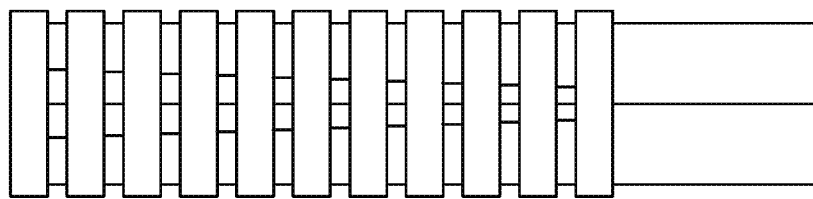
FIG. 21B is a cross-sectional view of the steerable member comprising a geometrically enhanced structure according to another exemplary embodiment of the present invention.
Figure 21A:
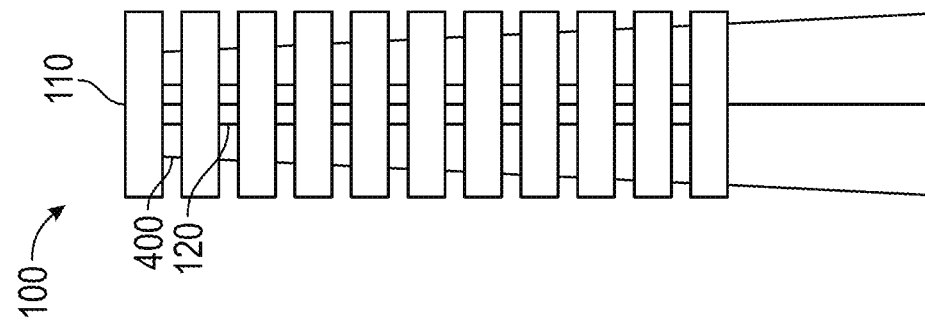
FIG. 21A is a cross-sectional view of the steerable member comprising a geometrically enhanced structure according to one exemplary embodiment of the present invention.

FIGS. 21A to 21C are cross-sectional views of a steerable member according to one exemplary embodiment of the present invention. FIGS. 21A to C depict different embodiments for improving the concentration of bending at the distal end of the steerable member, which involves a geometrically enhanced structure in which the steerable member bends more easily at the distal end than at the proximal end.

Specifically, as shown in FIG. 21A, the bending segments 110 have lumens formed at a distance from the center of a cross-section of the steerable member, and the closer to the proximal end of the steerable member, the more distant the lumens in the bending segments get from the center of the cross-section of the steerable member. In this case, the moment applied to the steerable member 100 is smaller at the distal end and increases towards the proximal end. Thus, the steerable member 100 bends more easily toward the proximal end.

FIG. 21B, the connecting parts 120 may be configured to gradually change in shape along the length of the steerable member 100 such that the steerable member bends more easily at the proximal end than at the distal end. In an example, as illustrated in FIG. 21B, the bending properties along the length can be adjusted by configuring the connecting parts to have a larger sectional width at the distal end than at the proximal end. Alternatively, apart from adjusting the width of the connecting parts, the connecting parts may be configured in other various ways of shape variation, including adjusting the range of movement of connecting parts having a joint structure.

Also, as shown in FIG. 21C, the distance between the bending segments 110 may change along the length. Specifically, the connecting parts 120 may be positioned such that the distance between the bending segments gets shorter toward the distal end and longer toward the proximal end. In this case, the longer the distance between the bending segments, the easier the bending of the steerable member. This results in restriction of the bending near the distal end and improvement in the bending properties near the proximal end.

The steerable member of this configuration has a plurality of bending actuation wires located along the lumens, and the distal end of each bending actuation wire is fixed by a wire termination member 410 provided at the distal end of the steerable member.

Figure 22A:
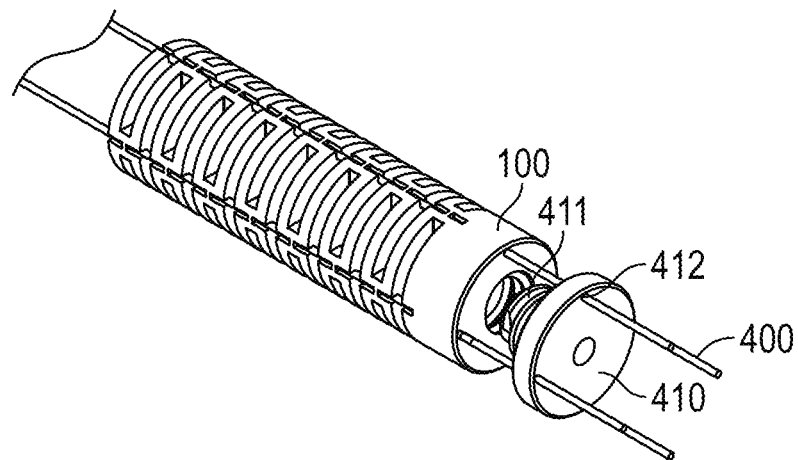
Figure 22B:
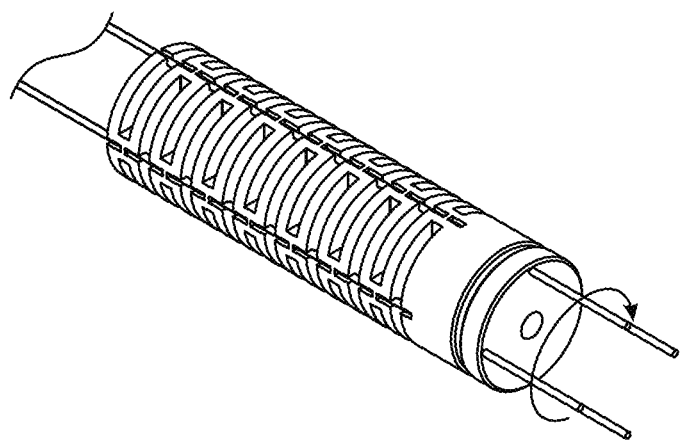
Figure 22C:
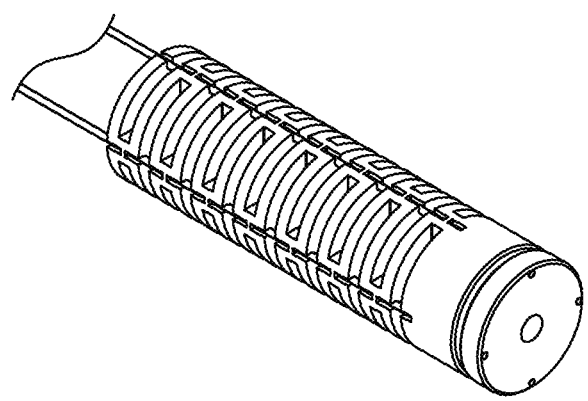

FIGS. 22A to 22C are views illustrating a method of fixing bending actuation wires by a wire termination member. As the steerable member and the bending actuation wires are very small in size, fixing individual bending actuation wires to the distal end of the steerable member is highly difficult. Accordingly, this exemplary embodiment uses a wire termination member capable of easily fixing a plurality of bending actuation wires.

As illustrated in FIG. 22A, the wire termination member 410 has a thread 411 on one side, and is screwed to the distal end of the steerable member 100. Also, the wire termination member includes a plurality of holes 412 through which a plurality of bending actuation wires pass, and the holes 412 are formed at locations corresponding to the lumens in the steerable member. Accordingly, the wire termination member can be screwed to the distal end of the steerable member while the bending actuation wires 400 are inserted in the holes of the wire termination member (FIG. 22B), thereby making it easy to fix the bending actuation wires (FIG. 22C).

Figure 23:
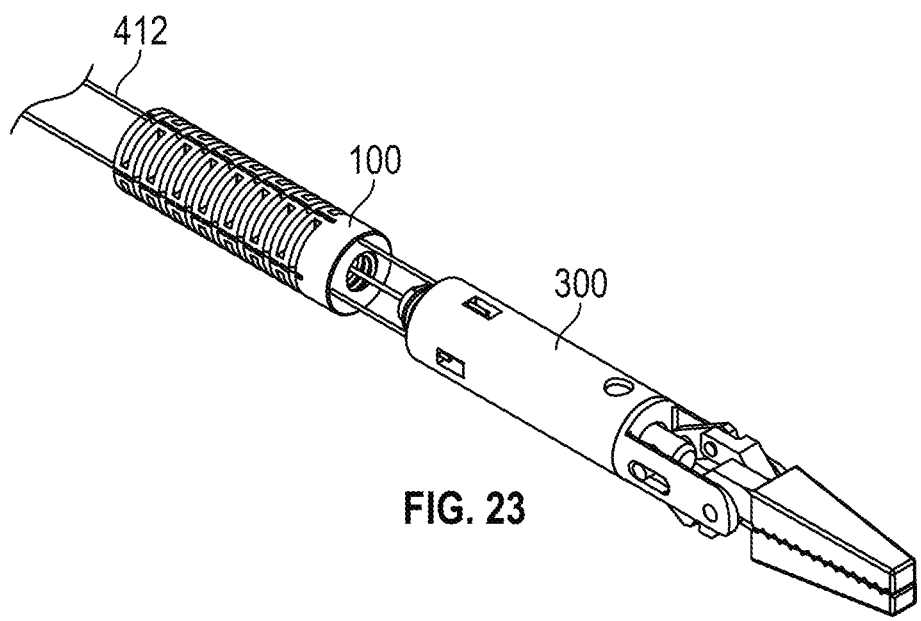
FIG. 23 is an isometric view of an end effector being used as a wire termination member according to another exemplary embodiment of the present invention.

The wire termination member may be a component that is provided between the steerable member and the end effector. In this case, the wire termination member may be screwed to the distal end of the steerable member, and the end effector may be connected to the wire termination member. Alternatively, as illustrated in FIG. 23, the end effector 300 may be used as the wire termination member by fixing the bending actuation wires 400 to the inside of the end effector 300 and screwing the end effector 300 directly to the distal end of the steerable member 100.

Although FIGS. 22A to 22C have been described with respect to a steerable member having the structure shown in FIG. 10, it is needless to say that the bending actuation wires can be likewise fixed even if the steerable member has other structures.

In the above discussion, various exemplary embodiments of the steerable member have been described with reference to FIGS. 5 to 22. The steerable member is described as a component of the surgical apparatus that has an end effector, but the present invention is not limited thereto. For example, the present invention is applicable to bendable steerable members for various kinds of surgical instruments, such as an imaging unit or a lumen unit with a working channel.

Referring back to FIG. 2, the end effector 300 is provided at the distal end of the steerable member. As described above, the end effector 300 may be coupled directly to the distal end of the steerable member 100 or coupled to it through a component such as the wire termination member. The end effector 300 comprises various types of surgical elements 311 for use in surgery. FIG. 2 illustrates an end effector comprising a forceps by way of example.

The proximal end of the end effector 300 is connected to the effector actuation wire 500. The effector actuation wire 500 is located in the channels 111 of the steerable member 100, and mechanically connected to the manipulating part 10 through the steerable member 100 and the flexible member 200. Accordingly, the effector actuation wire 500 actuates the end effector 300 as it moves lengthwise by the manipulating part 10.

Figure 24A:
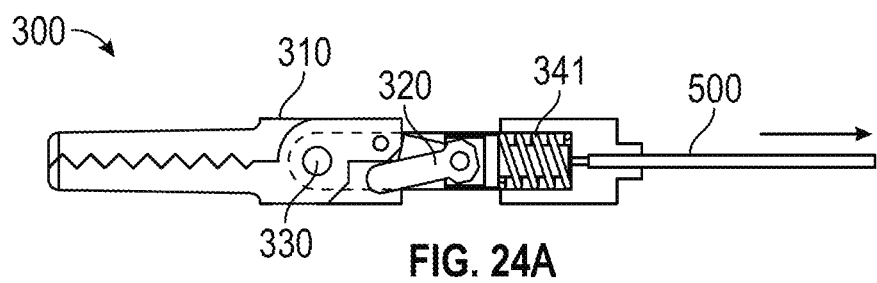
FIG. 24A is a cross-sectional view of the end effector of FIG. 23 in a first mode.
Figure 24B:
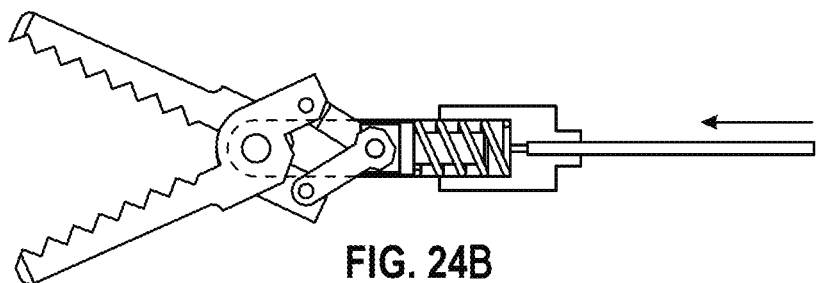
FIG. 24B is a cross-sectional view of the end effector of FIG. 23 in a second mode.

FIGS. 24A to 24B are cross-sectional views schematically illustrating the operating principle of the end effector. The end effector 300 operates in a first mode when the effector actuation wire 500 is pulled in the direction of the manipulating part 10 (FIG. 24A), and operates in a second mode when the effector actuation wire 500 is pulled in the direction of the end effector 300 (FIG. 24B). The first mode involves closing the forceps of the end effector, and the second mode involves opening the forceps. The action of pulling the effector actuation wire 500 in the direction of the manipulating part may be done easily by the driving part of the manipulating part, thereby transmitting the force to the end effector. On the other hand, the action of bringing the effector actuation wire 500 back in the direction of the end effector 300 may not be done properly by the driving part 400 because the effector actuation wire has a wire structure. Accordingly, in this exemplary embodiment, the end effector 400 may include an elastic body 341 to perform a second mode operation by pulling the effector actuation wire 500 using the elasticity of the elastic body 341.

Specifically, as illustrated in FIG. 24, an effector module of the end effector comprises an instrument portion 310 for performing a surgical operation and an actuation portion 320 for actuating the instrument portion 310. The instrument portion 310 is linked to the actuation portion 320, and configured such that the surgical elements 311 are opened or closed on both sides by the movement of the actuation portion 320 while a joint 330 of the instrument portion 310 is fixed. The elastic body 341 may be located at the proximal end of the actuation portion. When the effector actuation wire 500 is pulled by the manipulating part 10, the actuation portion 320 moves backward while pushing the elastic body 341 and the surgical elements 311 are therefore closed (FIG. 24A). Also, when the force acting on the effector actuation wire 500 is released by the manipulating part 10, the restoration force of the elastic body 341 causes the actuation portion 320 to move in the direction of the instrument portion 310, thereby opening the surgical elements 311 (FIG. 24B). In this way, the operative mechanism of the end effector can be simplified with the use of the elastic body.

Figure 25:
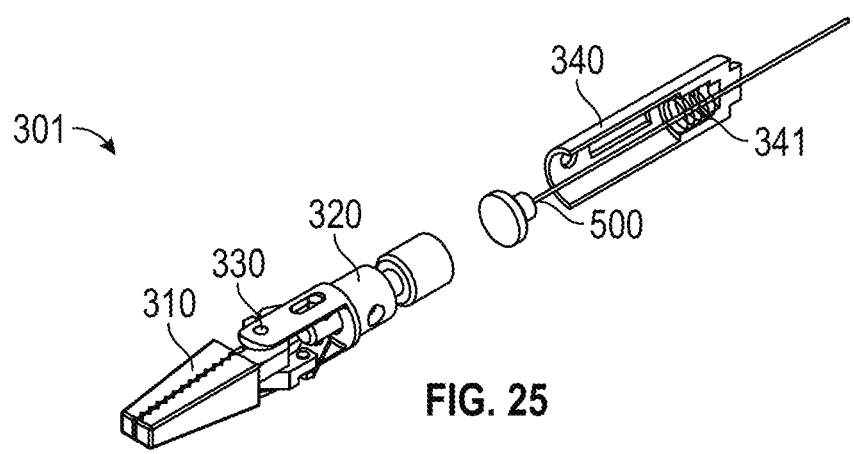
FIG. 25 is an exploded view of an end effector using an elastic body according to one embodiment of the present invention.

The structure of the end effector using the elastic body may be designed in various ways. FIG. 25 is a view illustrating an example of such an end effector. As illustrated in FIG. 25, the end effector 300 may comprise an effector module 301 and a body portion 340 where the effector module 301 is mounted. The instrument portion 310 of the effector module 301 is configured to be exposed to the distal end of the body portion 340, and the actuation portion 320 thereof is accommodated inside the body portion 340. A joint 330 connecting the instrument portion 310 and the actuation portion 320 may be fixed at the body portion 340, and the actuation portion 320 may reciprocate inside the body portion 340. The elastic body 341 provided inside the body portion 340 is located behind the actuation portion 320, and the proximal end of the actuation portion 320 is connected to the effector actuation wire 500. Accordingly, the instrument portion 310 may be manipulated by moving the actuation portion 320 with the effector actuation wire 500 and the elastic body 341.

Also, all or part of the end effector 300 may be detachably connected to the distal end of the steerable member 100. Accordingly, a variety of instruments needed for surgery may be selectively fastened and used. In an example, the end effector 300 of FIG. 25 is configured such that the effector module 301 is attachable to or detachable from the distal end of the effector actuation wire 500. The effector module 301 and the distal end of the effector actuation wire 500 may be detachably fastened in various ways; for example, they may be magnetically fastened together according to the exemplary embodiment illustrated in FIG. 25. Accordingly, at least either the proximal end of the actuation portion 320 or the distal end of the effector actuation wire 500 consists of a magnetic body, which enables the fastening.

As described above, a surgical instrument according to this exemplary embodiment comprises a bendable steerable member 100 and an operable end effector 300. Also, the steerable member 100 and the end effector 300 are moved by a plurality of wire members such as the bending actuation wires 400 and the effector actuation wire 500. These wire members are arranged to pass through the steerable member 100 and the flexible member 200. Accordingly, if the wire members are linearly arranged so that each of them has the shortest path, the movement of the wires may be restricted or affected by the bending of the steerable member or flexing of the flexible member. Therefore, in this exemplary embodiment, at least one sleeve forming a path of travel of a wire member may be provided inside the steerable member or the flexible member. This sleeve is longer than the maximum length of the portion where the sleeve is provided (for example, the length of that portion when bent or flexed), so the wire members have a long enough path even when the steerable member is bent or the flexible member is flexed.

FIG. 26A is a cross-sectional view illustrating a path of travel of the effector actuation wire. As illustrated in FIG. 26A, one end of the effector actuation wire 500 is mounted at the proximal end of the end effector 300, and the other end is mechanically connected to the manipulating part 10 (FIG. 1). One end of a sleeve 600 forming a path of the effector actuation wire 500 is fixed in place at the distal end of the steerable member 100 or the proximal end of the end effector 300. Also, the other end is fixed in place at the proximal end of the flexible member 200. In this instance, the sleeve 600 is longer than the length of the portion where two ends of the sleeve are fixed (the sum of the length of the steerable member and the length of the flexible member). This extra length added to the sleeve (FIG. 26B) gives more room for the path of the effector actuation wire 500 even when the steerable member 100 is bent (FIG. 26C). Accordingly, the movement of the end effector 300 may be decoupled from the bending movement of the steerable member 100 to prevent its movement from being affected by the bending movement of the steerable member 100.

FIG. 27A is a view illustrating a path of travel of the bending actuation wire. As illustrated in FIG. 27A, a sleeve 600 for securing the path of the bending actuation wire 400 may be provided. In this case, one end of the sleeve 600 is fixed at the proximal end of the steerable member 100 or the distal end of the flexible member 200, and the other end is fixed at the proximal end of the flexible member 200 (see FIGS. 27B and 27C). The sleeve 600 is configured to have an extra length added to the linear length of the portion where the sleeve is placed. Accordingly, the bending of the steerable member 100 will not be affected by the flexing of the flexible member 200.

Figure 28:
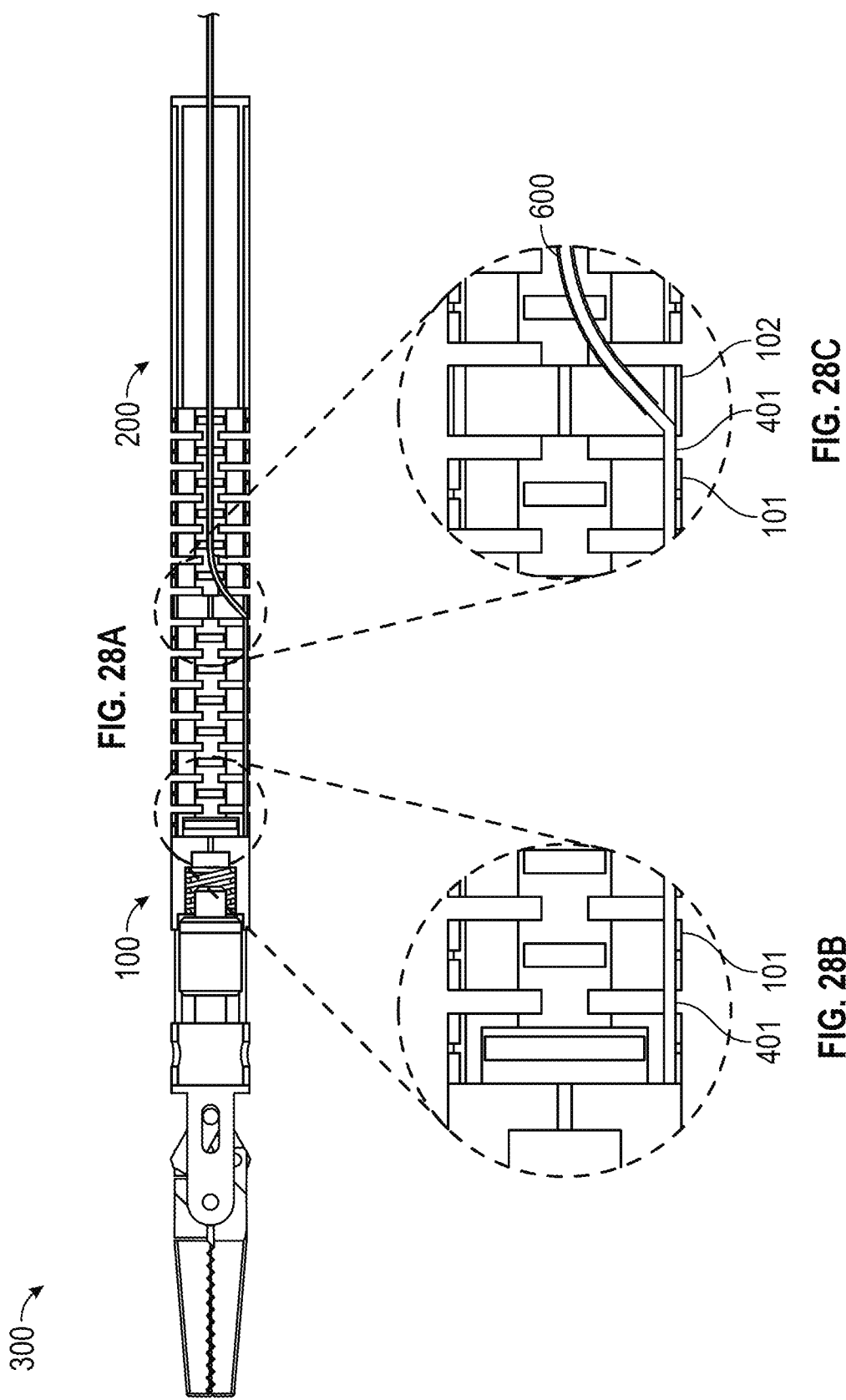
FIG. 28A is a cross-sectional view of an end effector having a bending actuation wire with two bendable portions according to one embodiment of the present invention.
FIG. 28B is an enlarged cross sectional view of the distal end of the steerable portion of FIG. 28A.
FIG. 28C is an enlarged sectional view of the proximal end of the flexible member of FIG. 28A.
Figure 29:
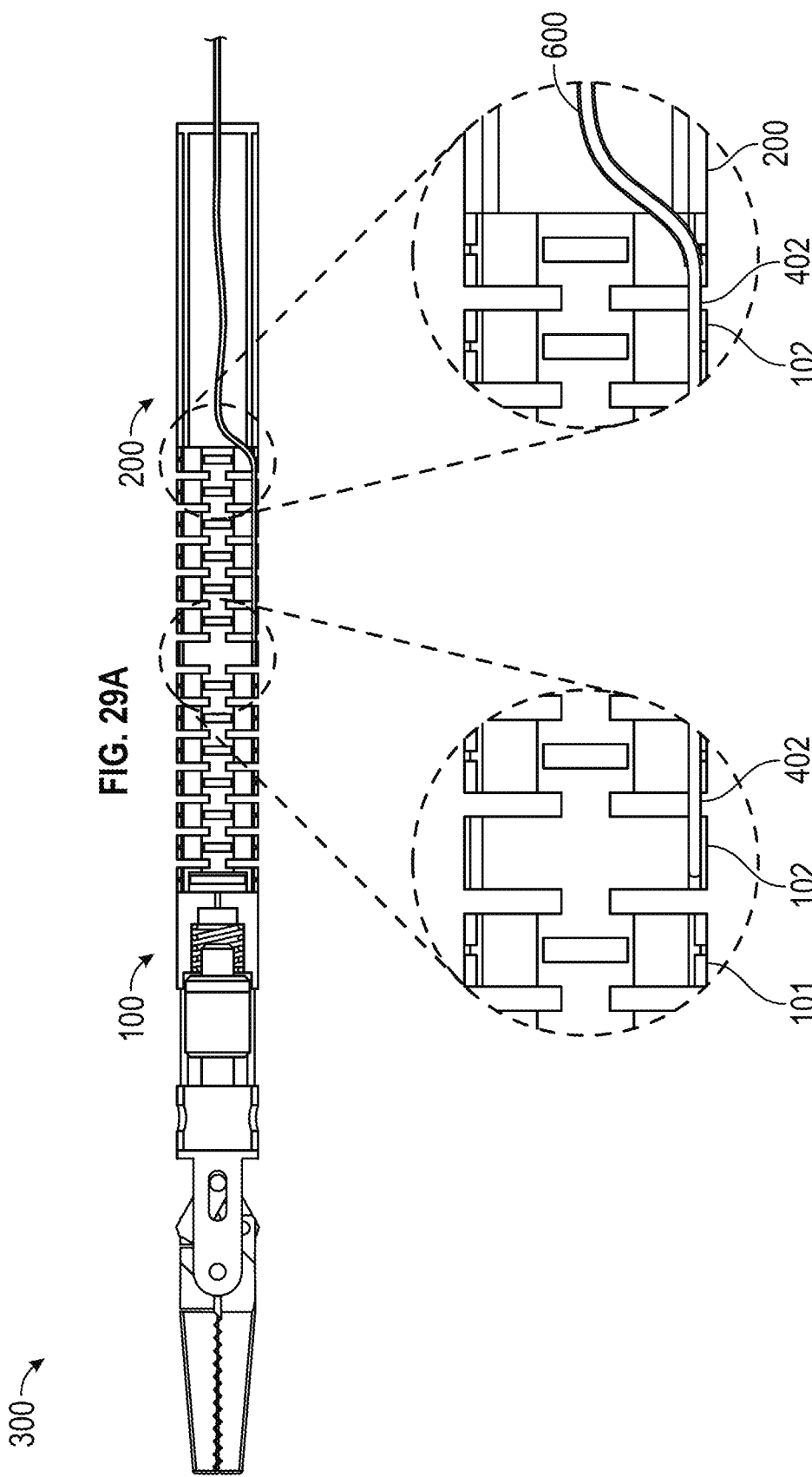
FIG. 29A is a cross-sectional view of an end effector having a bending actuation wire with two bendable portions according to another embodiment of the present invention.
FIG. 29B is an enlarged sectional view of the proximal end steerable portion of FIG. 29A.
FIG. 29C is an enlarged sectional view of the proximal end of the end effector of FIG. 29A.

FIGS. 28 and 29 are views illustrating a path of travel of a bending actuation wire 400 with two bendable portions. While the previous drawings illustrate a structure in which the steerable member 100 has one bending portion, the steerable member 100 may be divided into a distal end steerable portion 101 and a proximal end of steerable portion 102, which can bend separately. In this case, the distal end steerable portion 101 is bent with a distal end bending actuation wire 401, and the proximal end steerable portion 102 is bent with a proximal end bending actuation wire 402. One end of the distal end bending actuation wire 401 is fixed at the distal end of the distal end steerable portion 101, passes through the lumens in the distal end steerable portion 101, and then extends to the manipulating part 10 through hollow channels of the steerable member 100 and flexible member 200. Also, one end of the proximal end bending actuation wire 402 is fixed at the distal end of the proximal end steerable portion 102, passes through the lumens in the proximal end steerable portion 102, and then extends to the manipulating part 10 through hollow channels of the flexible member 200. In this instance, two distal end bending actuation wires 401 and two proximal end bending actuation wires 402 may be provided and have 1 degree of freedom in each bending portion, or four distal end bending actuation wires 401 and four proximal end bending actuation wires 402 may be provided and have 2 degrees of freedom in each bending portion.

As illustrated in FIG. 28A, a sleeve 600 for securing a path of the distal end bending actuation wire 401 may be provided. One end of this sleeve 600 may be fixed at the proximal end of the distal end steerable portion 101, and the other end may be fixed at the proximal end of the flexible member 200 (see FIGS. 28B and 28C). Also, as illustrated in FIG. 29A, a sleeve 600 for securing a path of the proximal end bending actuation wire 402 may be provided. One end of this sleeve 600 may be fixed at the proximal end of the proximal end steerable portion 102, and the other end may be fixed at the proximal end of the flexible member 200 (see FIGS. 29B and 29C). As is the case with the above-mentioned sleeves, each sleeve 600 has an extra length, so the bending movement of each bending portion can be decoupled.

Figure 26:
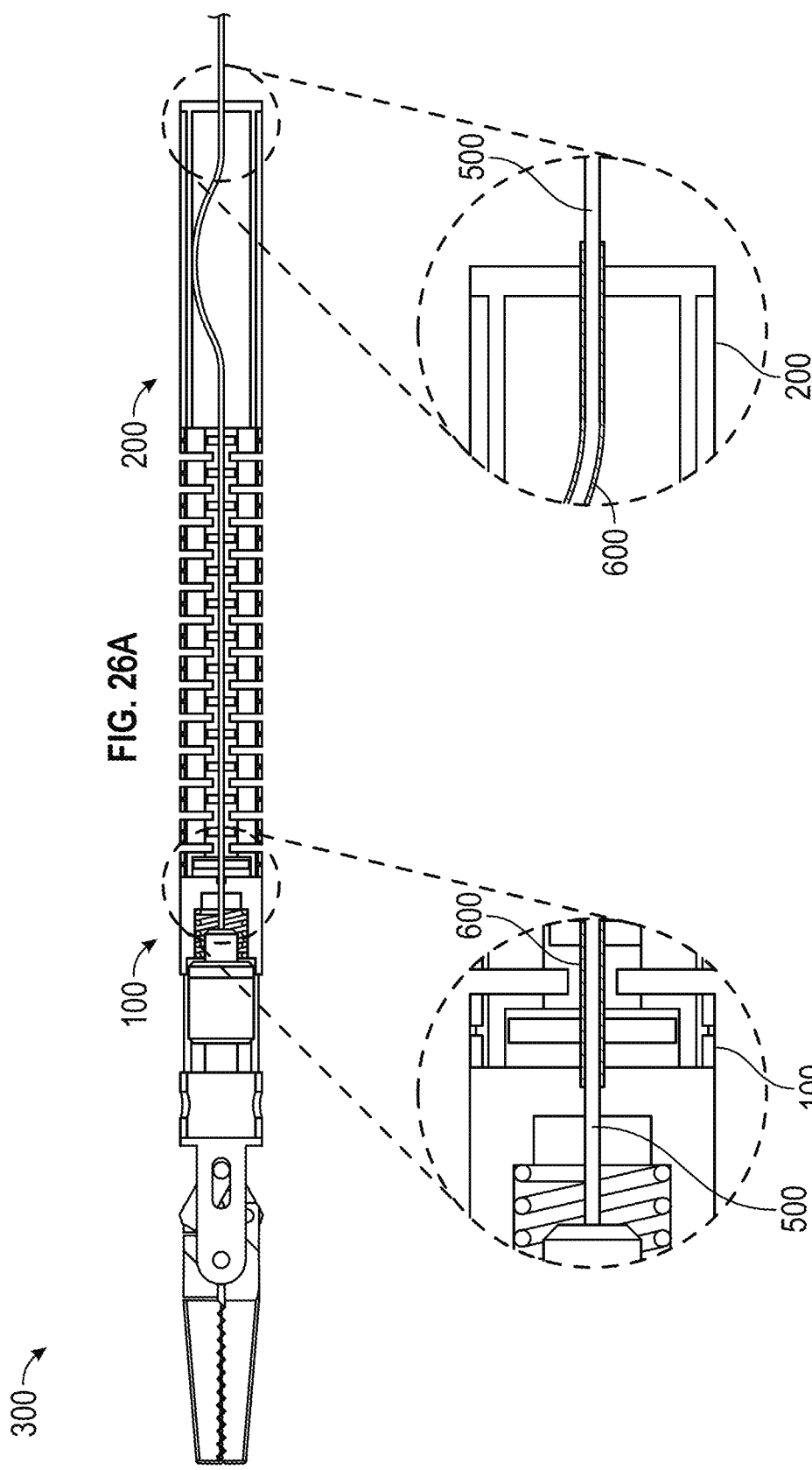
FIG. 26A is a cross-sectional view of an end effector having an effector actuation wire according to one embodiment of the present invention.
FIG. 26B is an enlarged sectional view of the distal end of the steerable member of the end effector of FIG. 26A.
FIG. 26C is an enlarged sectional view of the proximal end of the end effector of FIG. 26A.
Figure 27:
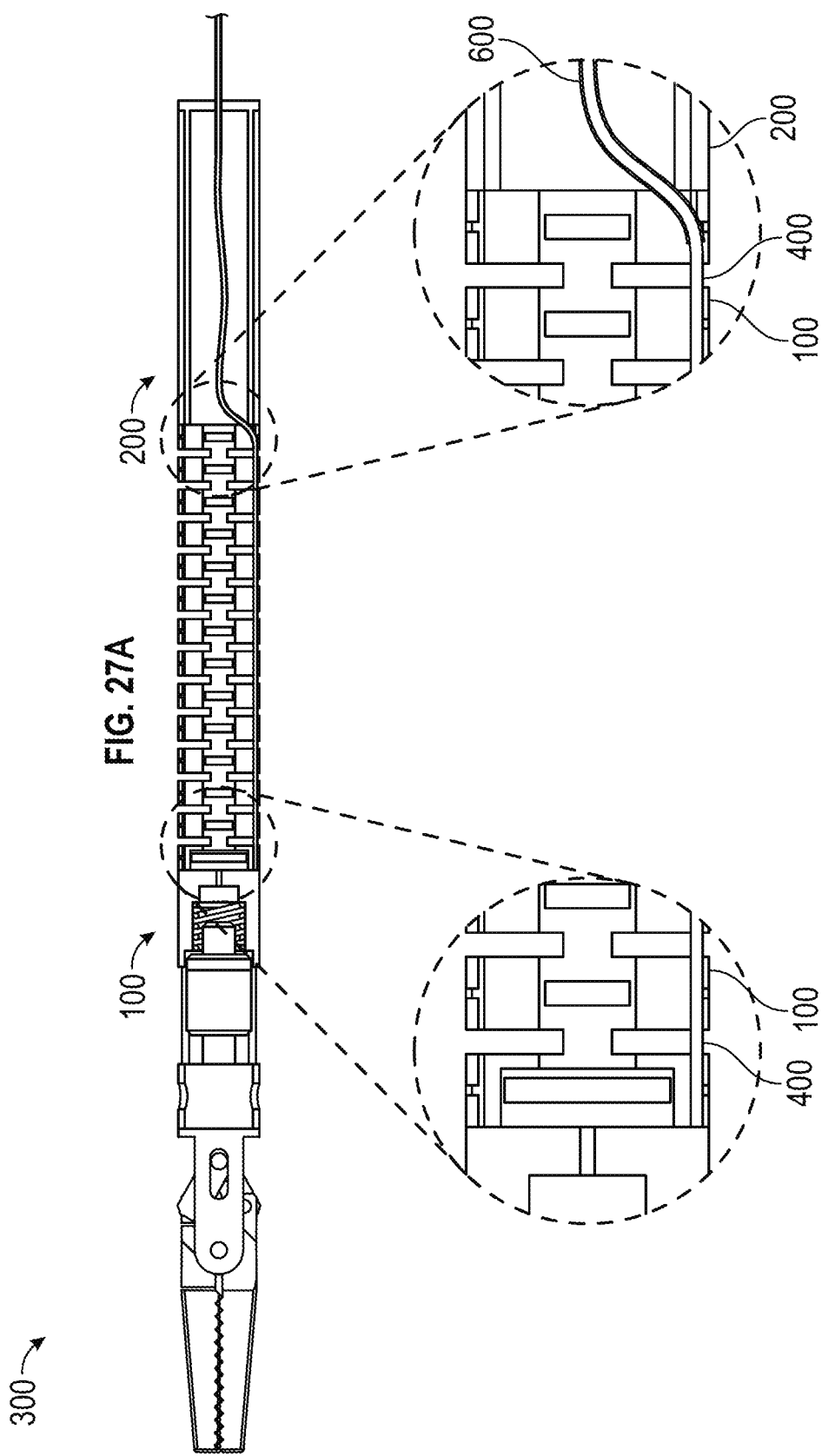
FIG. 27A is a cross-sectional view of an end effector having a bending actuation wire according to one embodiment of the present invention.
FIG. 27B is an enlarged cross sectional view of the distal end of the steerable member of the end effector of FIG. 27A.
FIG. 27C is an enlarged cross sectional view of the proximal end of the end effector of FIG. 27A.s

As described above, the sleeves 600 explained with reference to FIGS. 26 to 28 have an extra length added to the length of the portion where they are placed, and they may comprise an elastic material, allowing their shape to change along with the movement of the components. Such a sleeve structure allows decoupling of the movement of each component from the movement of the others, and prevents wire members in narrow channels from being twisted or damaged by friction.

Figure 30:
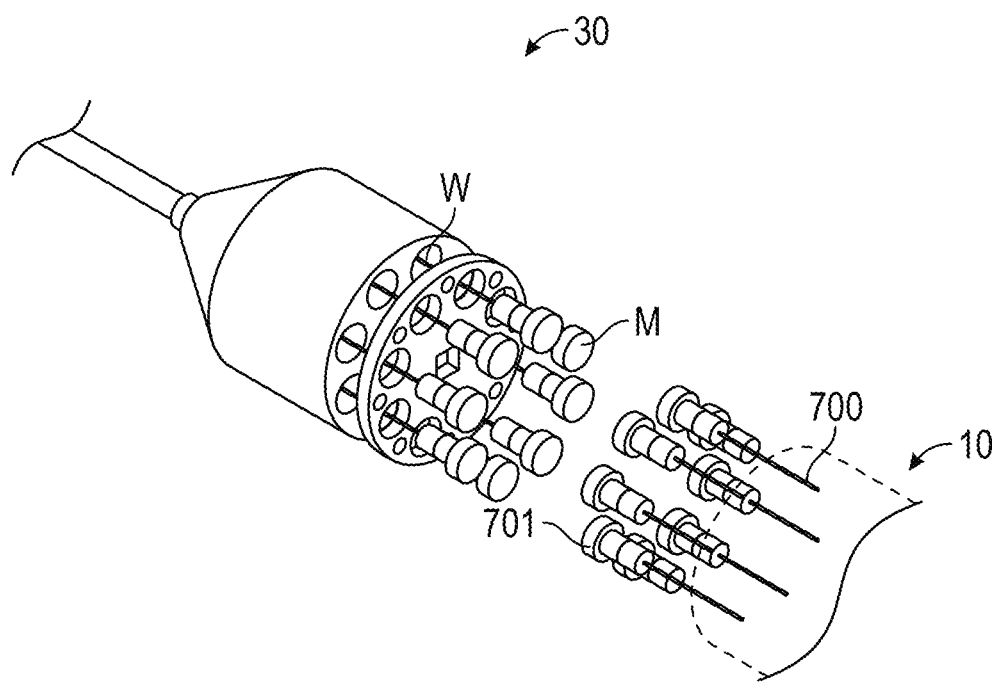
FIG. 30 is a schematic isometric view illustrating a connecting structure of the end of a surgical instrument and a manipulating part.

FIG. 30 is a view illustrating a connecting structure of the end of a surgical instrument and the manipulating part. As explained above, the surgical instruments 30 are respectively located in passages in the insertion part 20, and the end of a surgical instrument is mechanically connected to the manipulating part 10. The manipulating part 10 comprises transmission members 700 corresponding to a plurality of wire members W of the surgical instrument and couplers 701 to be fastened to wires. The wire members W of the surgical instrument each include a proximal end module M at the proximal end, and each proximal end module M is fastened to the corresponding coupler 701. Thus, each wire member can be moved by each driving part in the manipulating part.

In this case, the insertion part 20 and the manipulating part 10 are attachable to or detachable from each other, and the surgical instrument 30 provided in the insertion part 20, too, is attachable to or detachable from the manipulating part 20. This means that the insertion part or the surgical instrument can be cleaned or replaced with new ones. The surgical instrument 30 and the manipulating part 10 may be detachably fastened in various ways; for example, they may be magnetically fastened together, as shown in FIG. 30. Accordingly, the proximal end of the surgical instrument (specifically, the proximal end modules of the bending actuation wires and effector actuation wire) or the distal end of the manipulating part (specifically, the couplers of the transmission members) may be consist of a magnetic body and be attached to or detached from each other by magnetic force.

Figure 31A:
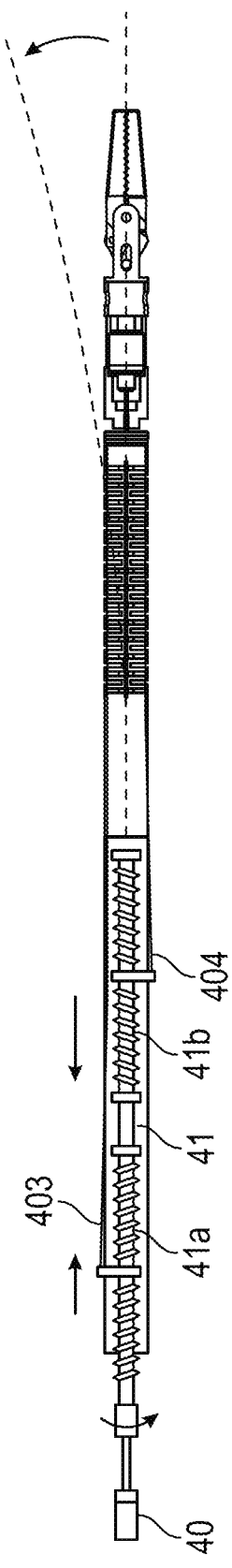
FIG. 31A is a schematic plan view of a manipulating part comprising a single screw member according to one embodiment of the present invention, wherein a first bending actuation wire and a second bending actuation wire move respectively in opposite directions on a straight line.
Figure 31B:
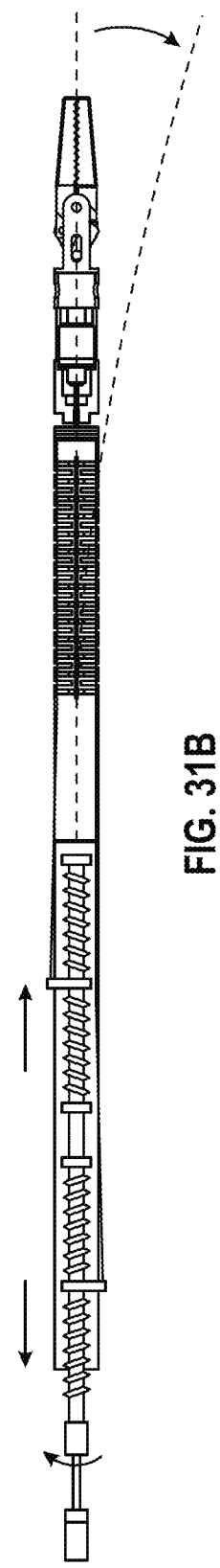
FIG. 31B is a schematic plan view of the manipulating part of FIG. 31A, wherein a first bending actuation wire and a second bending actuation wire move respectively in reverse directions of FIG. 31A.
Figure 32:
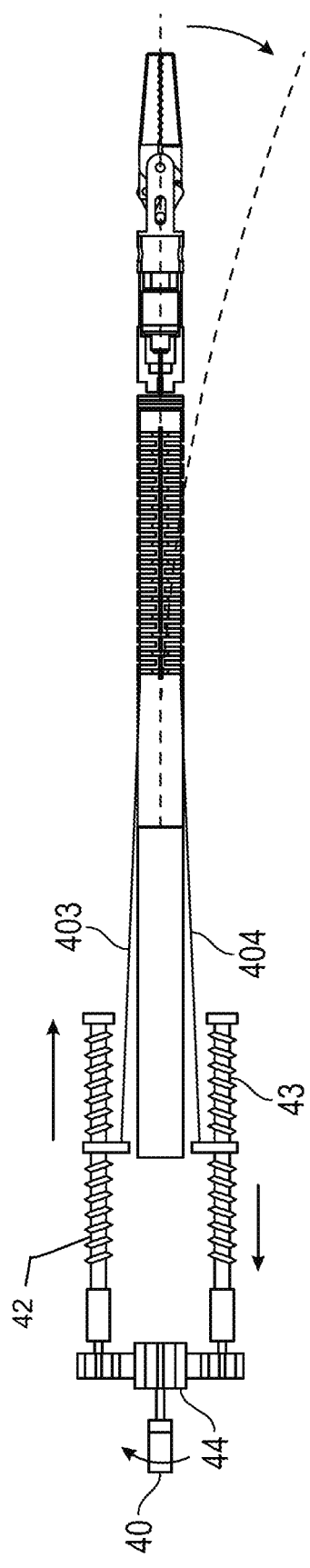
FIG. 32 is a schematic plan view of a manipulating part comprising a pair of screw members and a driving part according to one embodiment of the present invention.

FIGS. 31 and 32 schematically illustrate the configuration of the manipulating part 10 for moving the bending actuation wires 400. The wire members W of the above-described surgical instrument are mechanically connected to the driving part 40 of the manipulating part 10 and move linearly along with the movement of the driving part 40. The driving part may be constructed using various devices such as an actuator, a linear motor, a motor, etc. Also, each wire member may be connected to different driving parts so that they can move separately.

In this instance, a pair of bending actuation wires 400 located facing each other within the steerable member 100 move in opposite directions when bending occurs. Specifically, when bending occurs, the bending actuation wire near the center of curvature has a shorter path and the bending actuation wire on the other side of the center of curvature has a longer path. Accordingly, the pair of wires facing each other may move simultaneously in opposite directions with the use of a single driving part 40. In this case, the manipulating part can be designed to be compact by reducing the number of driving parts.

In FIGS. 31A and 31B, the manipulating part comprises a screw member 41 and a driving part 40 for rotating the screw member 41. The screw member 41 may be a bi-directional lead screw, which means that two thread portions having different orientations are formed on a single screw member. Accordingly, the coupler of a transmission member to be connected to a first bending actuation wire 403 is coupled to a first thread 41a, and the coupler of a transmission member to be connected to a second bending actuation wire 404 is coupled to a second thread 41b. Accordingly, as the driving part rotates, the first bending actuation wire 403 and the second bending actuation wire 404 move respectively a corresponding distance, in opposite directions on a straight line, thereby causing the steerable member to bend. Also, the directions of movement of the first bending actuation wire 403 and the second bending actuation wire 404 may be reversed by changing the direction of rotation of the driving part, thus enabling them to bend in the reverse direction.

In FIG. 32, the manipulating part comprises a pair of screw members and a driving part 40 for rotating the screw members. The pair of screw members consists of a first lead screw 42 with a first thread and a second lead screw 43 with a second thread oriented in the opposite direction to the first thread. The first lead screw 42 and the second lead screw 43 are connected to the driving part 40 by a gear 44 and rotate in the same direction along with the rotation of the driving part. The first bending actuation wire 403 is mechanically connected to the first lead screw 42, and the second bending actuation wire 404 is mechanically connected to the second lead screw 43. Accordingly, as is the case in FIG. 31, when the motor rotates, the first and second bending actuation wires may move in opposite directions, causing the steerable member to bend.

Although FIGS. 31 and 32 depict the use of a screw member as an example to drive the bending actuation wires in a pair, it is needless to say that modifications can be made using various link structures.

FIGS. 33A and 33B are views schematically illustrating the length of a bending actuation wire before and after bending in an ideal continuous flexible arm. FIG. 33A shows the length of the bending actuation wire before bending in an ideal continuous flexible arm, while FIG. 33B shows the length of the bending actuation wire after bending in an ideal continuous flexible arm being pulled with a wire-driven mechanism A (e.g. a pulley).

In an ideal continuous flexible arm, let a bending actuation wire be located on two opposite sides of the wire-driven mechanism A having a width of $2r$, wherein "r" indicates a radius of the wire-driven mechanism A; "$L_1$" and "$L_2$" respectively indicate the length of the bending actuation wire from both opposite sides of the wire-driven mechanism A to the bending segment (not shown) before bending; "$L_1'$" and "$L_2'$" respectively indicate the length of the bending actuation wire from both opposite sides of the wire-driven mechanism A to the bending segment (not shown) after bending; "L" indicates the length from the center of the wire-driven mechanism A to the bending segment; "R" indicates a radius of curvature when the wire-driven mechanism A is pulled as an arrow pointed to, and the angle of bend by the wire-driven mechanism A is denoted by "θ".

In the ideal continuous flexible arm shown in FIGS. 33A and 33B, the total length of the bending actuation wire before and after bending can be represented as the following equation:

before bending: $L_1+L_2=2R\theta$;

after bending: $L_1'+L_2'=(R+r)\theta+(R-r)\theta=2R\theta$;

$L_1+L_2=L_1'+L_2'$.

However, as shown in FIGS. 34A and 34B which are view schematically illustrating the length of a bending actuation wire before (shown in FIG. 34A) and after bending (shown in FIG. 34B) in the actual condition. As FIG. 34B illustrated, the bending actuation wire is elongated by being pulled (indicated as ΔL elongation), resulting in slack B on the released wire, which causes backlash. In this condition, the total length of the length of the bending actuation wires before and after bending can be represented as the following equation:

before bending: $L_1+L_2=2R\theta$;

after bending: $L_1'+L_2'+\Delta L$ elongation=$(R+r)\theta+(R-r)\theta+\Delta L$ elongation=$2R\theta+\Delta L$ elongation;

$L_1+L_2 \neq L_1'+L_2'+\Delta L$ elongation.

Figure 35:
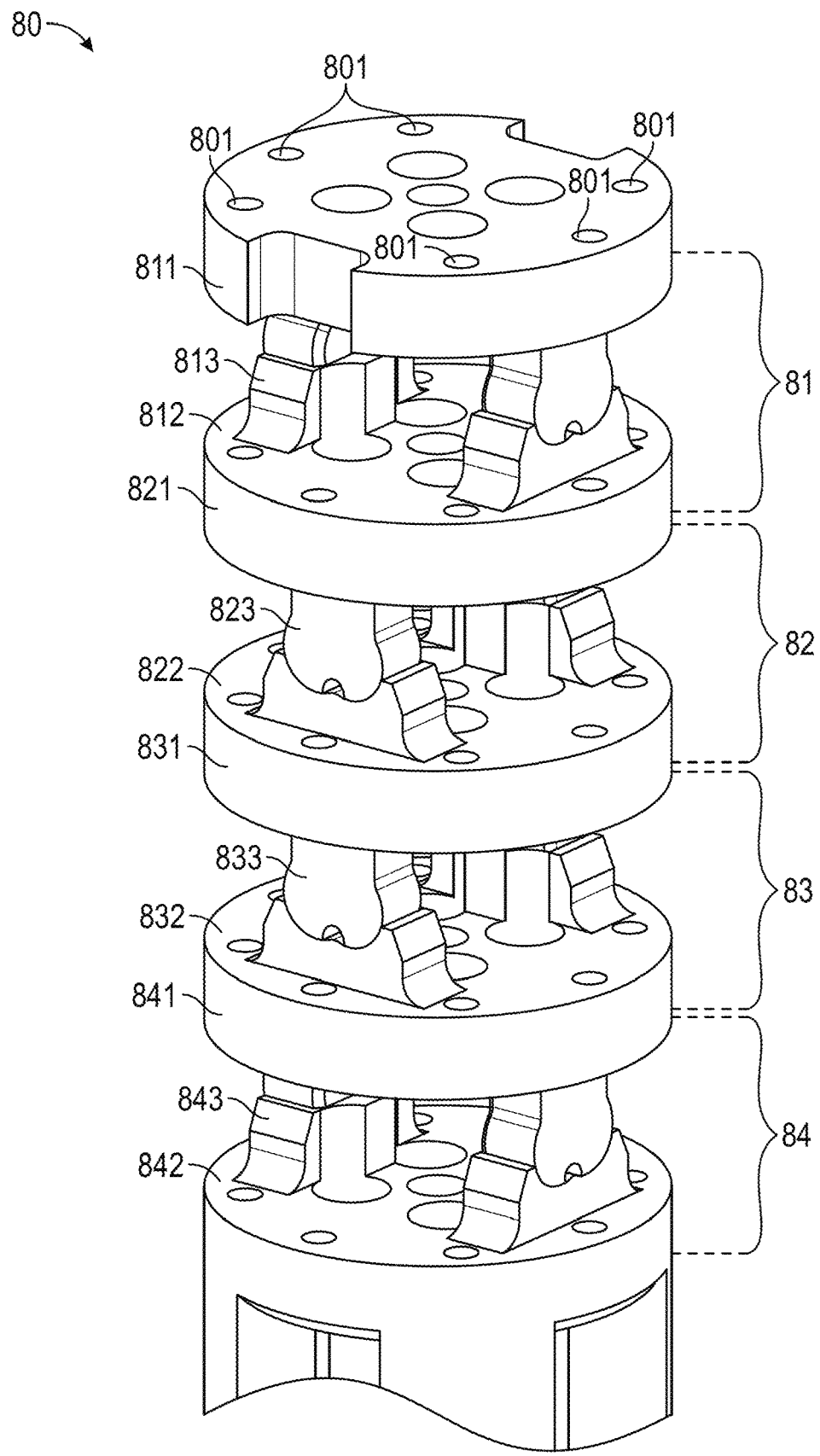
FIG. 35 is an isometric view illustrating an exemplary bending segment according to an exemplary embodiment of the present invention.

In contrast, in this exemplary embodiment, the bending segment may be configured to comprise a series of intermediate joints having tension-regulating members to minimize the slack caused by elongation. FIG. 35 is a view illustrating an exemplary bending segment according to an exemplary embodiment of the present invention. In FIG. 35, the bending segment 80 is illustrated to include four intermediate joints 81, 82, 83, 84 arranged along a longitudinal axis direction of the bending segment. Each intermediate joint 81, 82, 83, 84 has a first link portion 811, 821, 831 and 841 and a second link portion 812, 822, 832 and 842, respectively. Each intermediate joint 81, 82, 83, 84 may be interstacked orthogonally, in parallel or in any angle with the adjacent intermediate joint.

The bending segment 80 further comprises a plurality of lumens 801 passing through each intermediate joint 81, 82, 83, 84. The same number of bending actuation wires (being omitted for clarity) may be thus correspondingly provided to be arranged to pass through each lumen 801 respectively and cause the bending segment 80 to bend.

Each intermediate joint 81, 82, 83, 84 further comprises two tension-regulating member 813, 823, 833 and 843 coupled to the first link portion 811, 821, 831 and 841 and the second link portion 812, 822, 832 and 842. Each tension-regulating member 813, 823, 833 and 843 is configured to compensate for the elongation of the bending actuation wires when bending segments bend, whereby the length of bending actuation wires is altered and kept in a predetermined length.

Figure 36:
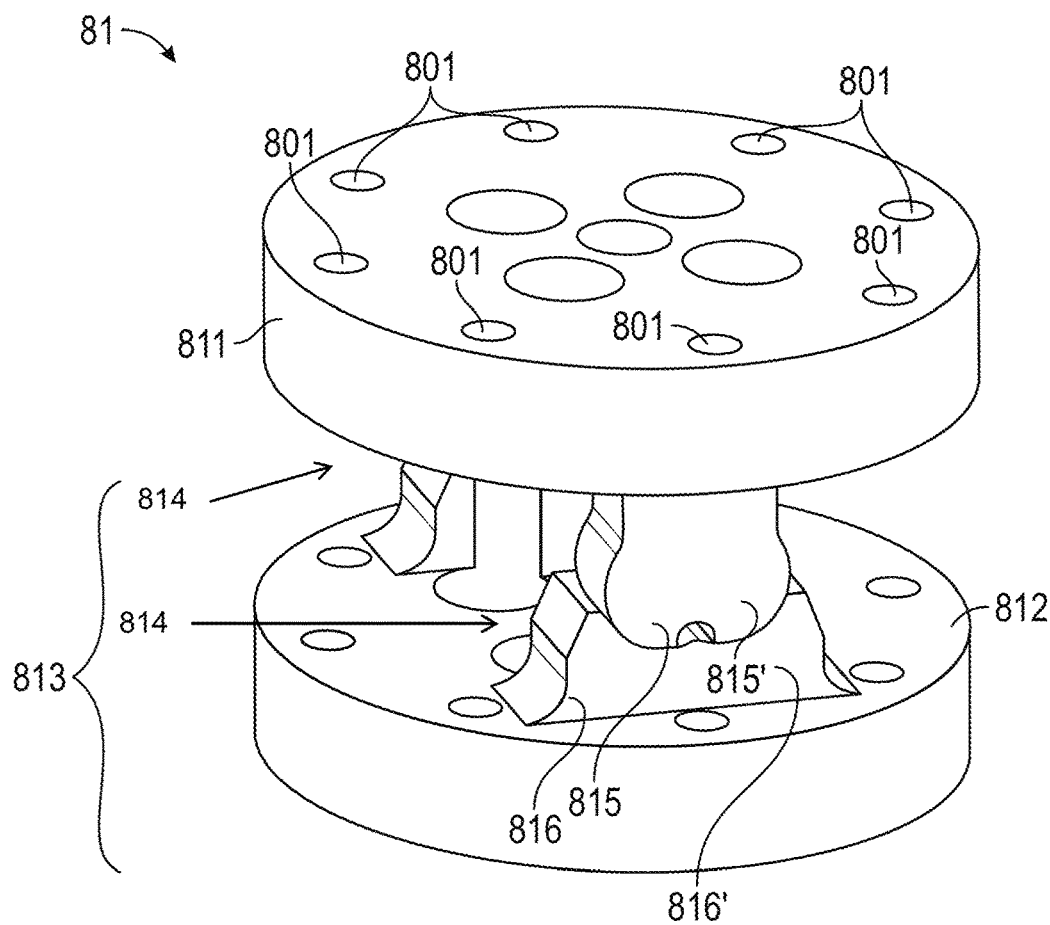
FIG. 36 is an isometric view illustrating an exemplary tension-regulating member in FIG. 35 according to an exemplary embodiment of the present invention.

In FIG. 36, the tension-regulating member 813 is a double-hinged joint comprising two off-axis hinge joints 814. Each off-axis hinge joint 814 comprises a first interfacing half 815, 815' coupled to the first link portion 811 and a second interfacing half 816, 816' coupled to the second link portion 812 and correspondingly pivoted to the first interfacing half 815, 815'. In this exemplary embodiment, each first interfacing half 815, 815' may have a protrusion end, respectively, while the second interfacing half 816, 816' correspondingly may have a recess end. In another exemplary embodiment, each first interfacing half may respectively have a recess end instead, while the second interfacing half correspondingly has a protrusion end.

Figure 37A:
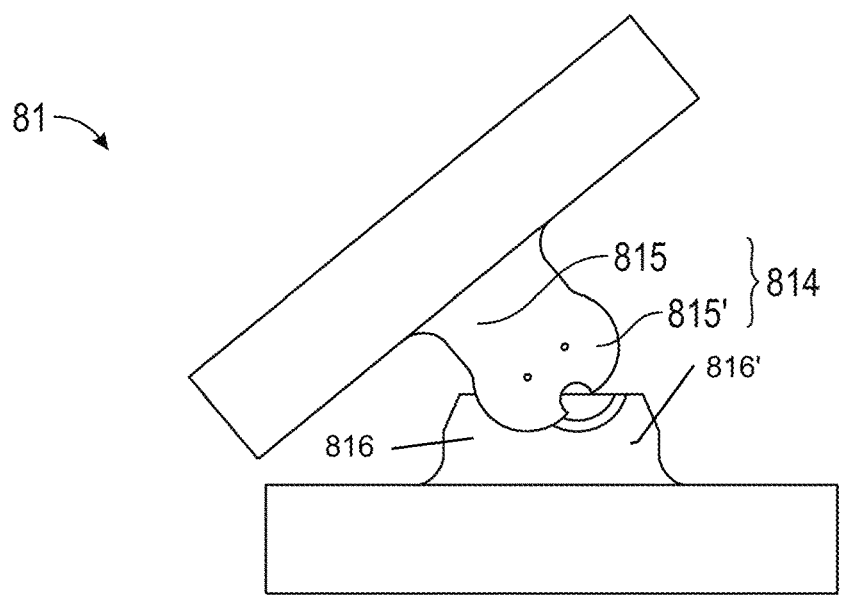
Figure 37B:
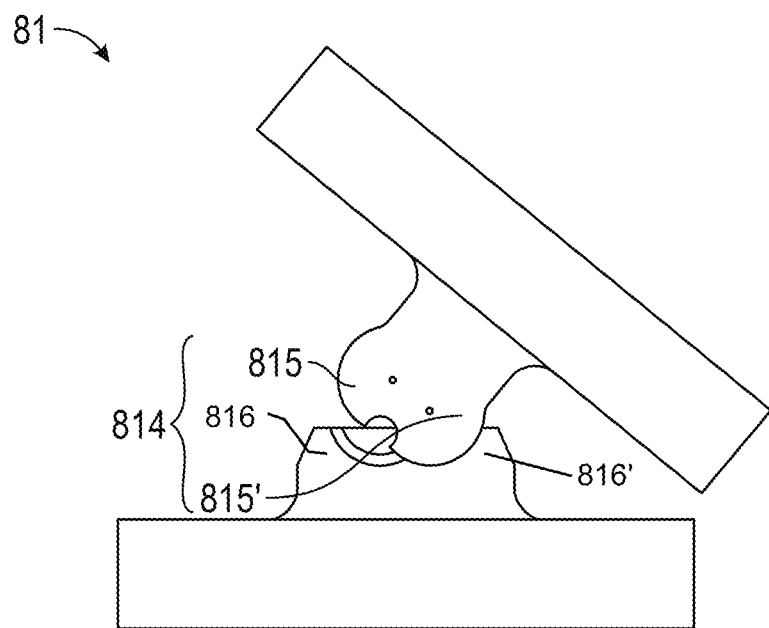
FIG. 37B is a front view of the tension-regulating member bending to the right side.

Pivotal motion will occur on one of the two off-axis hinges 814 depending on bending orientation. FIGS. 37A and 37B illustrates pivotal motion of one of the tension-regulating member of FIG. 36, wherein FIG. 37A is a front view of the tension-regulating member bending on the left side, and FIG. 37B is a front view of the tension-regulating member bending on the right side. As shown in FIG. 37A, the intermediate joint bends in a bending orientation on the left side on the left hinge 814 which is offset from the longitudinal axis direction, whereby only first interfacing half 815 pivotally moves on the left side. Similarly, only first interfacing half 815' pivotally moves on the right side when intermediate joint 81 bends on the right side as shown in the FIG. 37B.

Figure 38A:
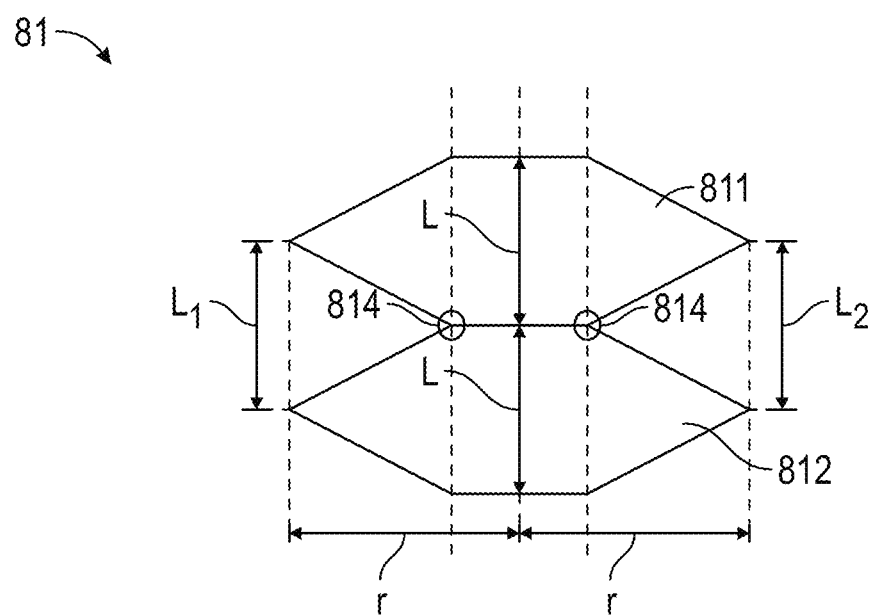
Figure 38B:
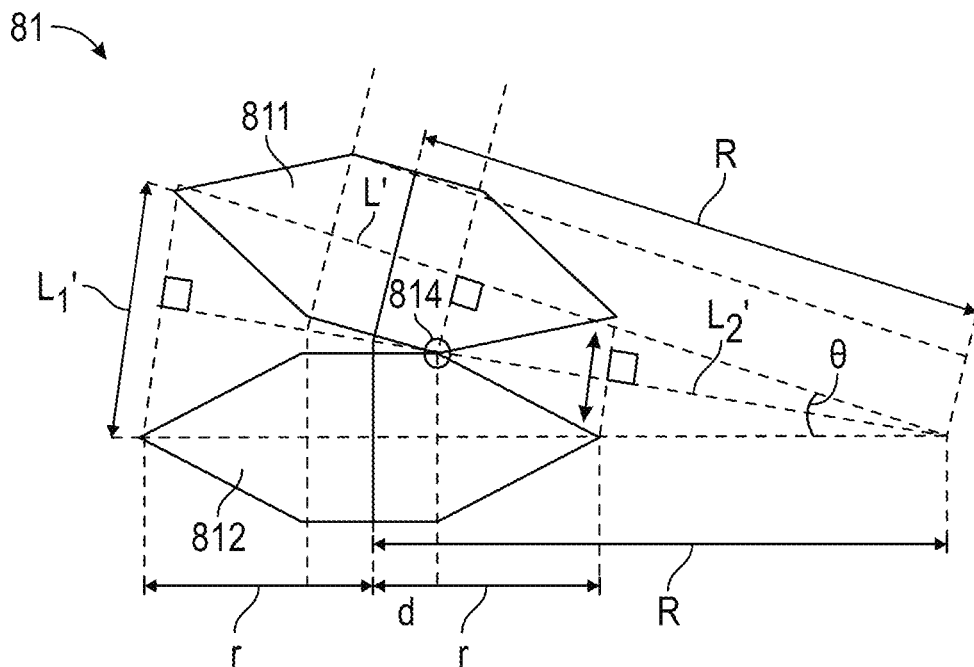
FIG. 38B shows the length of the bending actuation wire after bending.

FIG. 38 is a view schematically illustrating a slack in a wire caused by wire elongation being minimized using the tension-regulating member structure in FIG. 36. FIG. 38A shows the length of the bending actuation wire before the tension-regulating member structure bends, while FIG. 38B shows the length of the bending actuation wire after the tension-regulating member structure bends.

In FIGS. 38A and B, "L" indicates respectively the height of the first link portion 811 or the second link portion 812 along a direction of the central axis of the intermediate joint 81. "$L_1$" indicates the length of a bending actuation wire which passes through the lumen between the left side of the first link portion 811 and the second link portion 812 before bending, while "$L_1'$" indicates the length of the bending actuation wire in the left side after bending. "$L_2$" indicates the length of a bending actuation wire which passes through the lumen between the right side of the first link portion 811 and the second link portion 812 before bending, while "$L_2'$" indicates the length of the bending actuation wire in the right side after bending. "r" indicates a radius from the central axis of each link portion to the lumen that the bending actuation wire passes through. "R" indicates a radius of curvature when the intermediate joint 81 bends and the angle of bend is denoted by "θ". "d" herein indicates a distance from the central axis of each link portion to each off-axis hinge joints 814.

As shown in FIGS. 38A and B, if wire elongation is ignored in this exemplary embodiment, the total length of the length of the bending actuation wire before and after bending can be represented as the following equation:

$$L_1 = L_2 = L;$$

$$L'_1 = 2(R+r)\sin(\theta/2); L'_2 = 2(R-r)\sin(\theta/2);$$

$$L_1 = L_2 = L = L' = 2(R-d)\tan(\theta/2);$$

$$L_1 + L_2 = 4(R-d)\tan(\theta/2);$$

$$L'_1 + L'_2 = 2(R+r)\sin(\theta/2) + 2(R-r)\sin(\theta/2) = 4R\sin(\theta/2);$$

$$\text{Herein}, R = L/(2\tan(\theta/2)) + d;$$

$$\Delta L = (L1 + L2) - (L1' + L2') =$$
$$2L - 4R\sin(\theta/2) = 2L - 4(L/(2\tan(\theta/2)) + d)(\sin(\theta/2).$$

Figure 39:
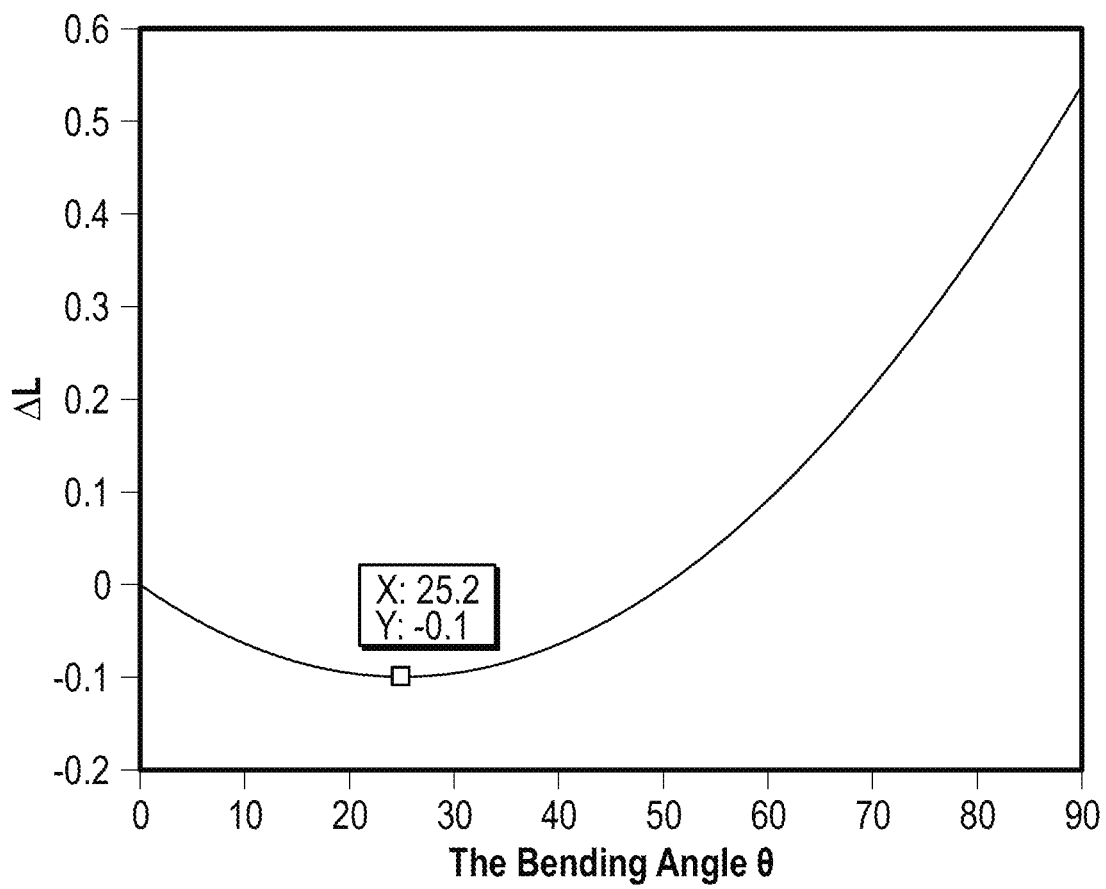
FIG. 39 is a diagram of the simulation result illustrating that the total length change (ΔL) of the bending actuation wire change as a function of the bending angle θ.

FIG. 39 is a diagram of the simulation result illustrating the total length change (ΔL) of the bending actuation wires as a function of the bending angle θ calculated using Matlab. For example, when, L=2, d=0.45, ΔL remains <0 when θ is within the range of motion of the designed joint (0 to 45 degrees); so the slack caused by wire elongation can be compensated by ΔL, made possible by off-axis hinge joints.

Thus, pivot motion of the intermediate joint 81 occurs on the hinge 814 located offset from the longitudinal axis direction of the intermediate joint 81. The length of bending actuation wires is altered and kept in a predetermined length in that the elongation of the bending actuation wires is compensated by the off-axis pivot motion.

Figure 40:
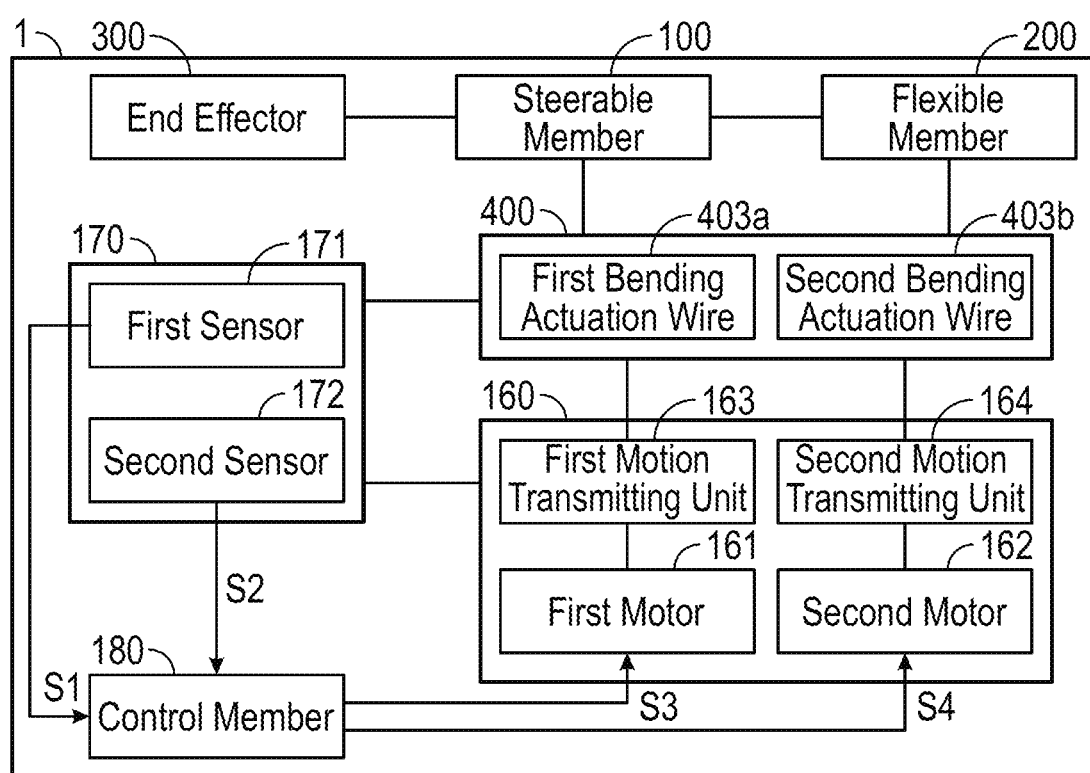
FIG. 40 is a block diagram illustrating a surgical instrument according to an exemplary embodiment of the present invention.

FIG. 40 is a block diagram illustrating a surgical instrument according to an exemplary embodiment of the present invention. FIG. 41 is a schematic view illustrating a surgical instrument according to an exemplary embodiment of the present invention. As illustrated in FIG. 40 and FIG. 41, a steerable member 100 that is bendable is provided at the distal end of the surgical instrument 30. The steerable member 100 has a plurality of bending segments 110 with hollow channels (not shown in FIGS. 40 and 41) that are connected together. Each bending segment 110 comprises a plurality of lumens 112 that are formed lengthwise. A flexible member 200 comprising a flexible material is provided at the proximal end of the steerable member 100. The flexible member 200 may comprise a hollow tube where various types of wire members connected from the distal end of the surgical apparatus 1 are located. Optionally, an end effector 300 is provided at the distal end of the steerable member 100, and the end effector 300 may be selectively actuated by an effector actuation wire 500 (e.g. see FIGS. 2, 24-26).

Each bending segment 110 of the steerable member 100 is connected to adjacent bending segments in a way that allows hinge movement, and bent by a bending actuation wire 400 (see, e.g. FIG. 2). In this exemplary embodiment, a first bending actuation wire 403a and a second bending actuation wire 403b that are located in separate lumens 112 to pass through the steerable member 100 and the flexible member 200, and the distal ends of the first bending actuation wire 403a and second bending actuation wire 403b are connected to the steerable member 100 and their proximal ends are mechanically connected to a drive member 160. Accordingly, when the first bending actuation wire 403a and second bending actuation wire 403b are moved by the drive member 160, the plurality of bending segments 110 move hingedly, thus causing 1-DOF bending motion of the steerable member 100.

The drive member 160 comprises a first motor 161, a second motor 162, a first motion transmitting unit 163 and a second motion transmitting unit 164. The first motor 161 is coupled to the first bending actuation wire 403a via a first motion transmitting unit 163, so that the power from the first motor 161 may be transmitted to the first bending actuation wire 403a to make it actuate. Similarly, the second motor 162 is coupled to the second bending actuation wire 403b via a second motion transmitting unit 164, transmitting the power from the second motor 162 to actuate the second bending actuation wire 403b. In this exemplary embodiment, the first motion transmitting unit 163 and the second motion transmitting unit 164 may be a lead screw or ball screw, but not limited to this.

A tension monitoring member 170 is further provided, comprising: a first sensor 171 and a second sensor 172. The first sensor 171 is coupled to the first motion transmitting unit 163 and coupled to the first bending actuation wire 403a. The first sensor 171 may provide a first feedback signal S1 responsive to sensing change in tension force of the first bending actuation wire 403a between the pre-bending and the desired bending motion. Similarly, a second sensor 172 is coupled to the second motion transmitting unit 164 and the second bending actuation wire 403b. The second sensor 172 may provide a second feedback signal S2 responsive to sensing change in tension force of the second bending actuation wire 403b between the pre-bending and the desired bending motion. In this embodiment, the first sensor 171 and the second sensor 172 are load cells, but not limited to this. The change in tension force of the first bending actuation wire 403a or the second bending actuation wire 403b provides an electrical value change (e.g. voltage, current or other parameters) that is calibrated to the load placed on the load cell.

The drive member 160 and the tension monitoring member 170 as described above are further electrically connected to a control member 180. The control member 180 may provide a first output signal S3 responsive to the first feedback signal S1 and transmit to the first motor. Upon receiving the first output signal S3, the first motor 161 will be driven to adjust (i.e. pull or release) the first bending actuation wire 403a. Similarly, the control member 180 may provide a second output signal S4 responsive to the second feedback signal S2, and transmit to the second motor 162 to adjust the second bending actuation wire 403b.

FIG. 42 is a view illustrating a surgical instrument in a bending status according to an exemplary embodiment of the present invention. When the first bending actuation wire 403a is actuated (i.e. pulled toward the direction of the first motor 161 as shown in FIG. 42) in order to bend the steerable member 100, tension of the first bending actuation wire 403a and/or the second bending actuation wire 403b changes because of various reasons. For example, change in the length between before and after bending along the bending direction of the second bending actuation wire 403b is smaller that of the first bending actuation wire 403a. Accordingly, tension of the second bending actuation wire 403b will be changed and backlash will be created due to bending, thus making fine adjustment difficult.

In this exemplary embodiment, the change in tension force caused by the first bending actuation wire 403a can be measured and monitored respectively by the first sensor 171 and the second sensor 172 via the voltage change induced by tension force. Then, the first feedback signal S1 and the second feedback signal S2 are provided to the control member 180 in response to the voltage change. After receiving and processing the first feedback signal S1 and the second feedback signal S2, the control member 180 will provide the first output signal S3 and the second output signal S4 to the first motor 161 and the second motor 162, separately. Then, the first motor 161 will be motionless in response to the first output signal S3, while the second motor 162 will release the second bending actuation wire 403b toward the direction of the steerable member 100 until the predetermined length in response to the second output signal S4, so that the first bending actuation wire 403a and the second bending actuation wire 403b will be maintained under a predetermined tension again.

Figure 43:
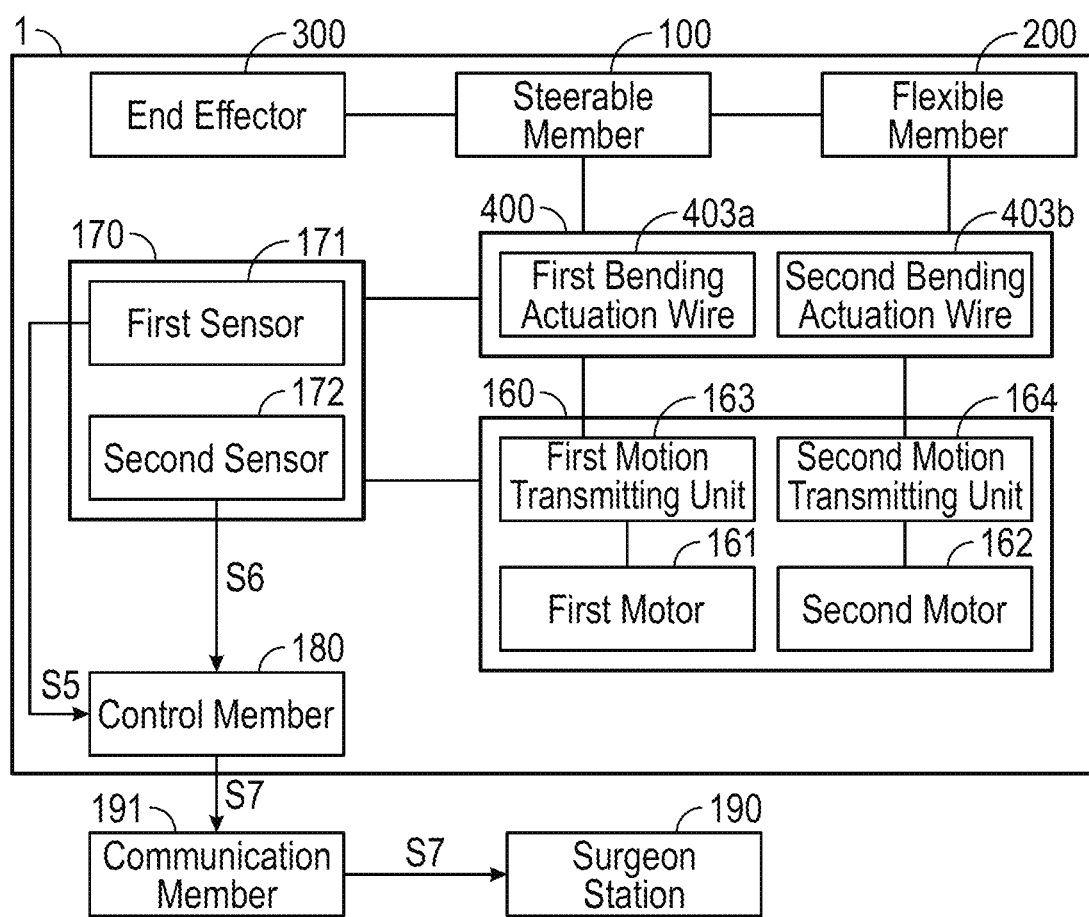
FIG. 43 is a block diagram illustrating a surgical instrument according to another exemplary embodiment of the present invention.
Figure 44:
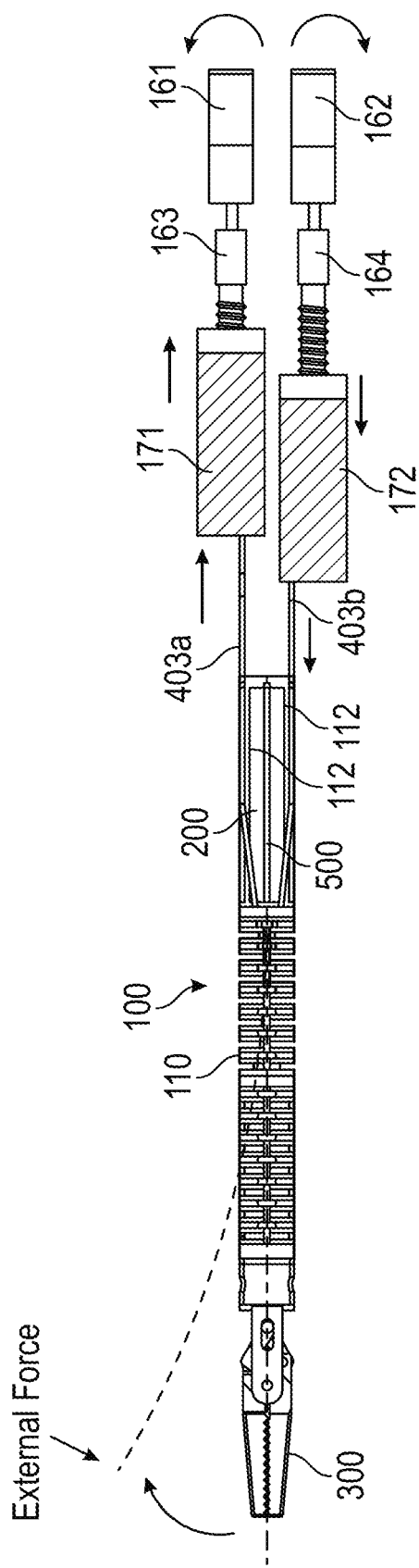
FIG. 44 is a schematic view illustrating a surgical instrument according to another exemplary embodiment of the present invention.

FIG. 43 is a block diagram illustrating a surgical instrument according to another exemplary embodiment of the present invention. FIG. 44 is a schematic view illustrating a surgical instrument according to another exemplary embodiment of the present invention. The end effector 300 may be subjected to various external forces as it is brought into frequent contact with a body wall or creates friction against a body material while being pushed forward along a pathway in the body or creates reaction force when operates the end effector 300. In the traditional surgery, a surgeon feels such external force by their own finger(s). However, in the robotic surgery, surgeons cannot feel the external force directly and all they can do is guess only by their observation or experience.

Thus, in this embodiment, the surgical instrument 30 provided herein may function together with a surgeon station 190 via a communication member 191.

The first sensor 171 and the second sensor 172 as described above may be configured to determine whether an external force is applied or not, depending on whether the potential difference between the sensed value and the value that tension in normal operation applied to the steerable member 100 exceeds a preset threshold value $\Delta V_{th}$. When the external force is determined to be applied, the first sensor 171 and the second sensor 172 will provide a first external-force signal S5 and a second external-force signal S6 respectively to the control member 180. The control member 180 will further provide an instruction signal S7 transmitted via communication member 191 in response to the first external-force signal S5 and the second external-force signal S6.

The communication member 191 may be a build-in one within the control member 180 or an external one. Also, the communication member 191 may use any telecommunication technology in the art. For example, in some embodiments, the communication member 191 may comprise a wireless transmitter and a wireless receiver (not shown in FIGs). In other embodiments, where the signal is digital, or digitized, and modulated by the control member 180, wireless transmitter may be configured according to a standard protocol, e.g., Bluetooth®. Alternatively, any other suitable configuration of hardwired or wireless transmitter, standard or proprietary, may be used. Further, wireless transmitter may include an antenna (not shown) extending therefrom to facilitate transmission of the signal to wireless receiver.

The surgeon station 190 is adapted to be manually manipulated by surgeons to, in turn, control motion of the surgical instrument 30 in response to the surgeons' manipulation. In this embodiment, the surgeon station 190 is configured to display information related to resistance force or vibration in response to the instruction signal S7 to surgeon station 190. In one embodiment, the control member 180 as described above may comprise a haptic feedback controller (not shown in the FIGS) to process and transmit the instruction signal S7 in form of haptic feedback. The haptic feedback may be provided through various forms, for example, mechanosensation, including, but not limited to, vibrosensation (e.g. vibrations), force-sensation (e.g. resistance) and pressure-sensation, thermoperception (heat), and/or cryoperception (cold). The surgeon station 190 may comprise a haptic joystick (not shown in the FIGS) to transfer haptic feedback to the surgeons to inform them of the external force.

In other embodiments, the information related to resistance force or vibration may be shown as graphical information or acoustic information. The surgeon station 190 herein may be various types known in the art that comprises a user's interface to display such graphical information or acoustic information. With the surgical instrument 30 provided herein, the external force may be detected and monitored by the tension monitoring member 170 and be displayed in a visualized form or be sensed by haptic feedback. Thus, surgeons can apply additional force using master device in the surgeon station timely against the external force, even in a tele-operation condition. Also, the accuracy to perform surgeries using the surgical instrument 30 will be increased.

In a further aspect, the present invention further provides a personalized master controller for use with robots and the like, and particularly to robotic surgical devices, systems, and methods. In robotically assisted surgery, the surgeon typically operates a master controller to remotely control the motion of robotic surgical devices at the surgical site. The master controller may be separated from the patient by a significant distance (e.g., across the operating room, in a different room, or in a completely different building than the patient). Alternatively, a master controller may be positioned quite near the patient in the operating room. Regardless, the master controller will typically include one or more manual input handles so as to move a surgical apparatus 1 as shown in FIG. 1 based on the surgeon's manipulation of the manual input handle. Typically, the manual input handle may be designed so as to allow smooth motion in the six degrees of freedom which may correspond to translations in three axes, as well as rotation in three axes.

Further, in order to drive the surgical instrument 30 to perform various surgical operations, the manual input handle itself may provide a degree of freedom for gripping motion. For example, a built-in gripping device may be further provided at the proximal end of the manual input handle, so that the gripping device may be levered to allow an operator to emulate the motion of scissors, forceps, or a hemostat and control actuation of surgical instrument 30, such as, to actuate the end-effector 300 (see FIG. 1) to move tissue and/or other material at the surgical site by gripping the same. However, such a gripping device may not be replaceable, and thus operators have no choice but are forced to use the manual input handle with the gripping device that they may not very familiar with. Precise control using a master controller for surgical operations may thus become more difficult.

Figure 45:
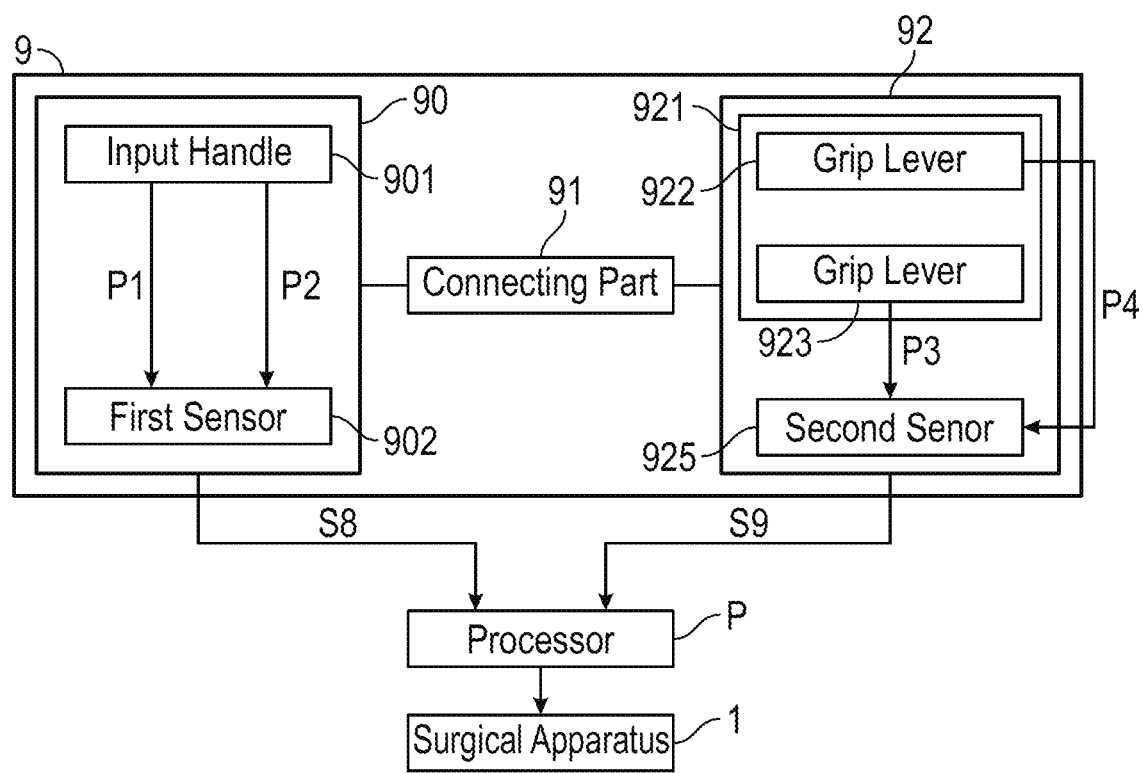
FIG. 45 is a block diagram illustrating a personalized master controller according to an exemplary embodiment of the present invention.

For the reasons outlined above, it would be advantageous to provide improved devices, systems, and methods for robotic surgery, telesurgery, and other telerobotic applications. In an exemplary embodiment, a personalized master controller is provided herein. FIG. 45 is a block diagram illustrating a personalized master controller according to an exemplary embodiment of the present invention. The personalized master controller 9 may be coupled to a processor P (e.g. a computer) that is electrically connected to the surgical apparatus 1. As provided herein, the personalized master controller 9 may comprise a control platform 90, a connecting part 91, and an interchangeable grip 92. As shown in FIG. 45, the control platform 90 may be configured to define and input one or more movement signals to control movement of the surgical apparatus 1 (see, e.g. FIG. 1) via the processor P.

Figure 46:
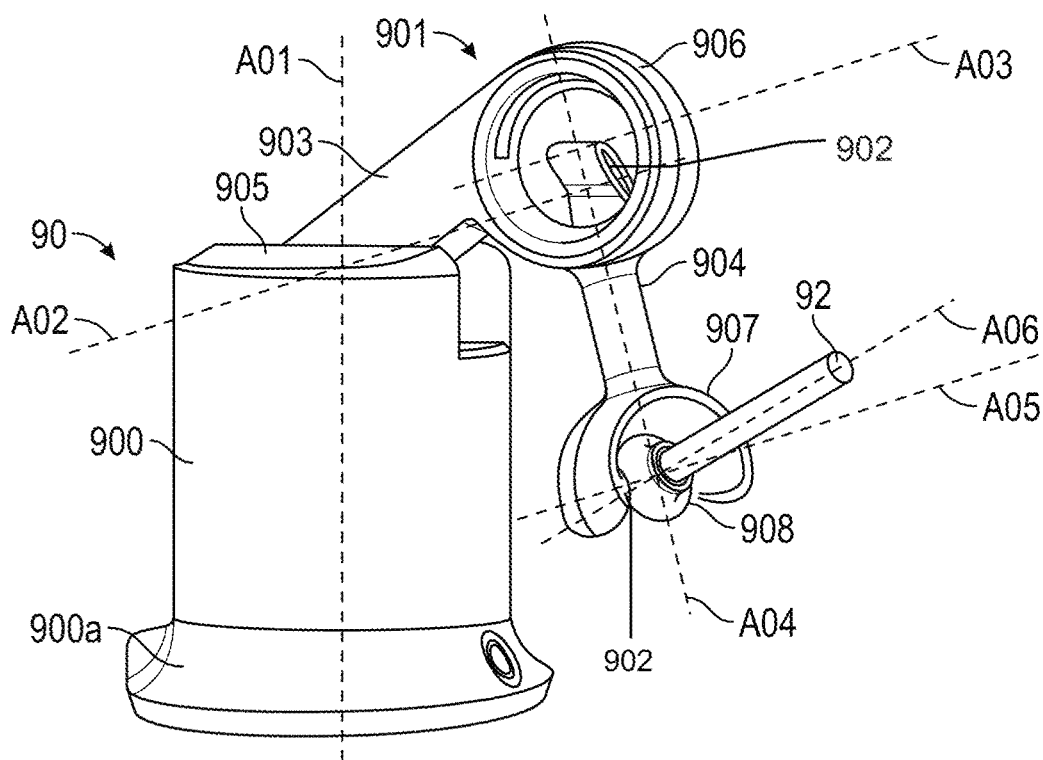
FIG. 46 is a schematic isometric view illustrating a personalized master controller according to an exemplary embodiment of the present invention.

In some alternative embodiments, the control platform 90 may be a serial manipulator, comprising: a number of rigid links connected with joints as described in U.S. Pat. Nos. 7,714,836, 7,411,576, and 6,417,638, which are incorporated herein by reference in their entirety. For example, as shown in FIG. 46, this type of the control platform 90 may comprise: a body 900 comprising a base 900a, an input handle 901 and a first plurality of sensors 902. The base 900a may rotate with respect to a first axis A01 having a substantially vertical orientation. The input handle 901 may comprise a first link 903, a second link 904 and a gimbal structure comprising an outer gimbal 907 and an inner gimbal 908. The first link 903 is pivoted to the body 900 via a first joint 905 which allows the first link 903 to move with respect to a second axis A02 having a substantially perpendicular orientation relative to the first axis A01. The second link 904 is pivoted to the first link 903 via a second joint 906 which allows the second link 904 to move with respect to a third axis A03 which is substantially parallel to the second axis A02.

A gimbal structure is mounted to the free end of the second link 904 comprising an outer gimbal 907 and an inner gimbal 908. The outer gimbal 907 is pivotally supported by the second link 904 and allowed to rotate with respect to a fourth axis A04 which is substantially perpendicular to the third axis A03. The inner gimbal 908 is pivotally supported by the outer gimbal 907 and allowed to rotate with respect to a fifth axis A05 which is substantially perpendicular to the fourth axis A04. A connecting part 91 (FIG. 48A) is mounted on the inner gimbal structure 908 and allows the interchangeable grip 92 that is electrically connected thereto to rotate with respect to a sixth axis A06.

Figure 47:
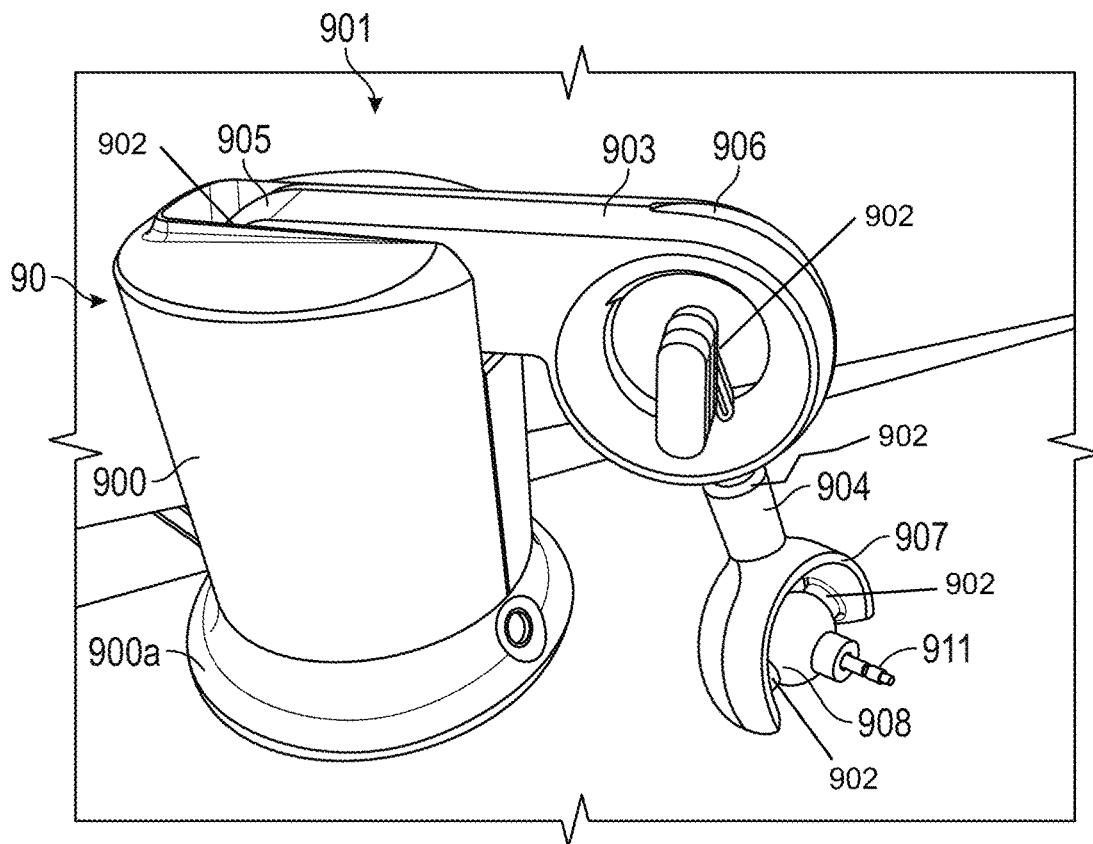
FIG. 47 is a schematic isometric view illustrating a control platform and a connecting part according to an exemplary embodiment of the present invention.

The connecting part 91 mounted on the inner gimbal structure 908 electrically connects the input handle 901 and the interchangeable grip 92. FIG. 47 is a perspective view illustrating a connecting part connected to the control platform according to an exemplary embodiment of the present invention. In one embodiment, the connecting part 91 may be a plug-and-socket type connector, but not limited to this. As shown in FIG. 47, in one embodiment, a one-prong plug 911 of the connecting part 91 may be coupled to the inner gimbal 908 while a corresponding socket structure 912 may be mounted at the distal end of the interchangeable grip 92 (see FIGS. 48B, 48D and 48F), such that the interchangeable grip 92 can be connected to on the inner gimbal structure 908 and be allowed to rotate with respect to a sixth axis A06 which is substantially perpendicular to the fifth axis A05. Alternatively, in some embodiments, the one-prong plug 911 of the connecting part 91 may be coupled to the distal end 924 of the interchangeable grip 92 while the socket structure 912 may be mounted the inner gimbal 908 (see FIG. 48).

Thus, the control platform 90 can provide six degrees of freedom movement including three translational degrees of freedom (in X, Y, and Z directions) and three rotational degrees of freedom (in pitch, yaw, and roll motion). The input handle 901 thereby can provide a plurality of position parameters P1 when it is translatable itself or with the mounted interchangeable grip 92 in X, Y, and Z direction with respect to the control platform 90 and/or provide a plurality of orientation parameters P2 when it is rotatable itself or with the mounted interchangeable grip 92 in pitch, yaw, and roll motion with respect to the control platform 90.

In one embodiment, one or more first sensors 902 may be mounted to the input handle 901 and configured to and generate one or more first movement signals S8 in response to the above-mentioned position parameters P1 and/or the orientation parameters P2. The first sensors 902, may, for example, be mounted to the first joint 905, the second joint 906 and/or the gimbal structure 907. In some embodiments, the first sensors 902 may be any type of sensors capable of measuring the position parameters P1 and/or the orientation parameters P2 based on the status or changes such as position, orientation, force, torque, speed, acceleration, strain, deformation, magnetic field, angle and/or light (but not limited to this) caused by the motion of the input handle 901 and/or mounted interchangeable grip 92. For example, the first sensors 902 may be pressure or force sensor, including but not limited to a piezoelectric sensor, a simple piezoelectric crystal, a Hall-Effect or a resistive strain gauge sensor, etc., all of which can be either stand-alone or integrated with signal-conditioning electronics (Wheatstone bridge, low-noise amplifier, A/D converter, etc.) into a single chip or single package sealed module. In other embodiments, may be an angle sensor, or a rotational sensor, but not limited to this. In a specific embodiment, the first sensor 902 may be a Hall-Effect sensor. As known in the art, the Hall-Effect sensor may be used in the presence of a corresponding magnet element (not shown in the FIGs.) to sense the magnetic field responding to the position parameter P1 and/or the orientation parameter P2. Then, the first sensors 902 may produce a first movement signal S8 to control movement of the surgical apparatus 1 (e.g., roll, translation, or pitch/yaw movement) accordingly.

FIGS. 48A to 48F are perspective views illustrating an interchangeable grip according to various exemplary embodiments of the present invention. In one embodiment, the interchangeable grip 92 provided herein may comprise a detachable handle 921 to mimic actual handles from manual surgical instruments. i.e., it may be the same size and shape, and can be squeezable or fixed, in order to provide realism to the surgeon. For example, two grip levers 922, 923 shown in FIG. 48 A may be pivoted at the proximal end of the detachable handle 921 so as to provide a degree of freedom of pinching or grasping motion. Both grip levers 922, 923 may be allowed to move toward each other relative to the detachable handle as indicated by arrows H to provide a degree of freedom of pinching or grasping motion. To mimic actual standard surgical handles depending on a field, surgeon, or operation, the detachable handle 921 and grip levers 922, 923 may be designed to be interchangeable as various types of surgical tools such as tweezers or laparoscopic hand Instruments as shown in FIG. 48C to 48F, respectively.

Also, in some embodiments, the detachable handle 921 may be mounted to or detach from the socket structure 912 at its distal end 924. The socket structure 912 provided herein may be capable of electrically connecting to or disconnecting from the one-prong plug 911 of the connecting part 91 see FIGS. 48B, 48D and 48F), so that the detachable handle 921 may be instrumented accordingly to receive relevant gripping motion input from the surgeon and the corresponding control signals are subsequently produced and transmitted to the surgical apparatus 1 via the control platform 90.

To sense gripping motion of the interchangeable grip 92, in one embodiment, the detachable handle 921 may define an inner hollow tubular space where a second sensor 925 may be housed to sense at least one parameter P3 based on the status or changes such as position, orientation, force, torque, speed, acceleration, strain, deformation, magnetic field, angle and/or light (but not limited to this) caused by the motion of the grip levers 922, 923.

In some embodiments, the second sensor 925 may be any type of sensors known in the art. For example, the second sensors 905 may be pressure or force sensor, including but not limited to a piezoelectric sensor, a simple piezoelectric crystal, a Hall-Effect or a resistive strain gauge sensor, etc., all of which can be either stand-alone or integrated with signal-conditioning electronics (Wheatstone bridge, low-noise amplifier, A/D converter, etc.) into a single chip or single package sealed module. In other embodiments, the second sensors 925 may be an angle sensor, or a rotational sensor, but not limited to this. In a specific embodiment, the second sensor 902 may be a Hall-Effect sensor. The Hall-Effect sensor may be used in the presence of a corresponding magnet element (not shown) to sense the magnetic field as known in the art, such that the Hall-Effect sensor may measure the gripping parameters P3 and/or P4 based on the status or changes of the magnetic field caused by the motion of the grip levers 922, 923. Then, the Hall-Effect sensor may produce a second movement signal S9 that can control the movement of the end-effector 300 shown in FIG. 1 accordingly. (e.g. opening and closing (gripping) movement of the end-effector 300 that may be a gripping device (e.g., jaws or blades).)

Figure 49:
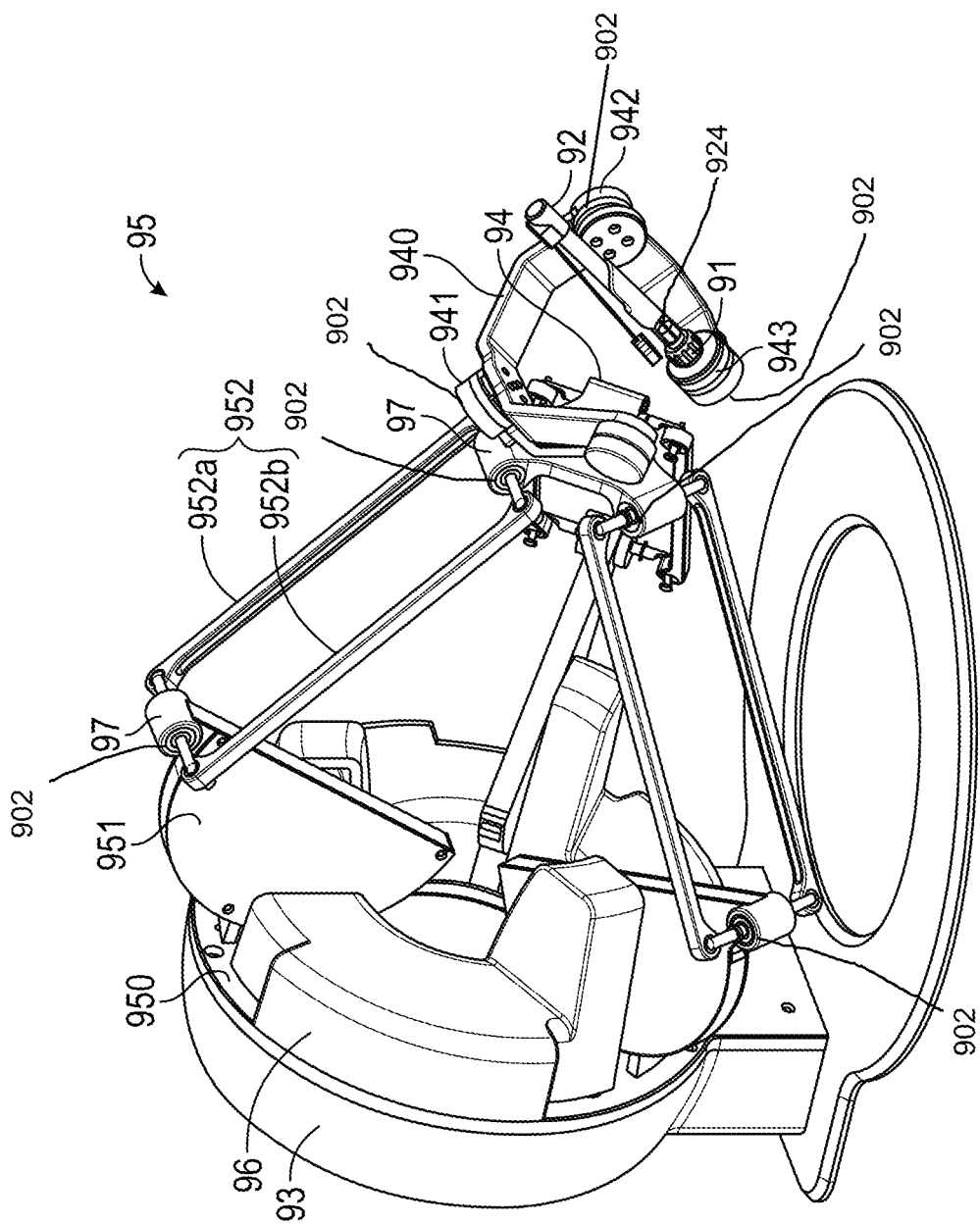
FIG. 49 is an isometric view schematically illustrating a personalized master controller according to another embodiment of the present invention.
Figure 50:
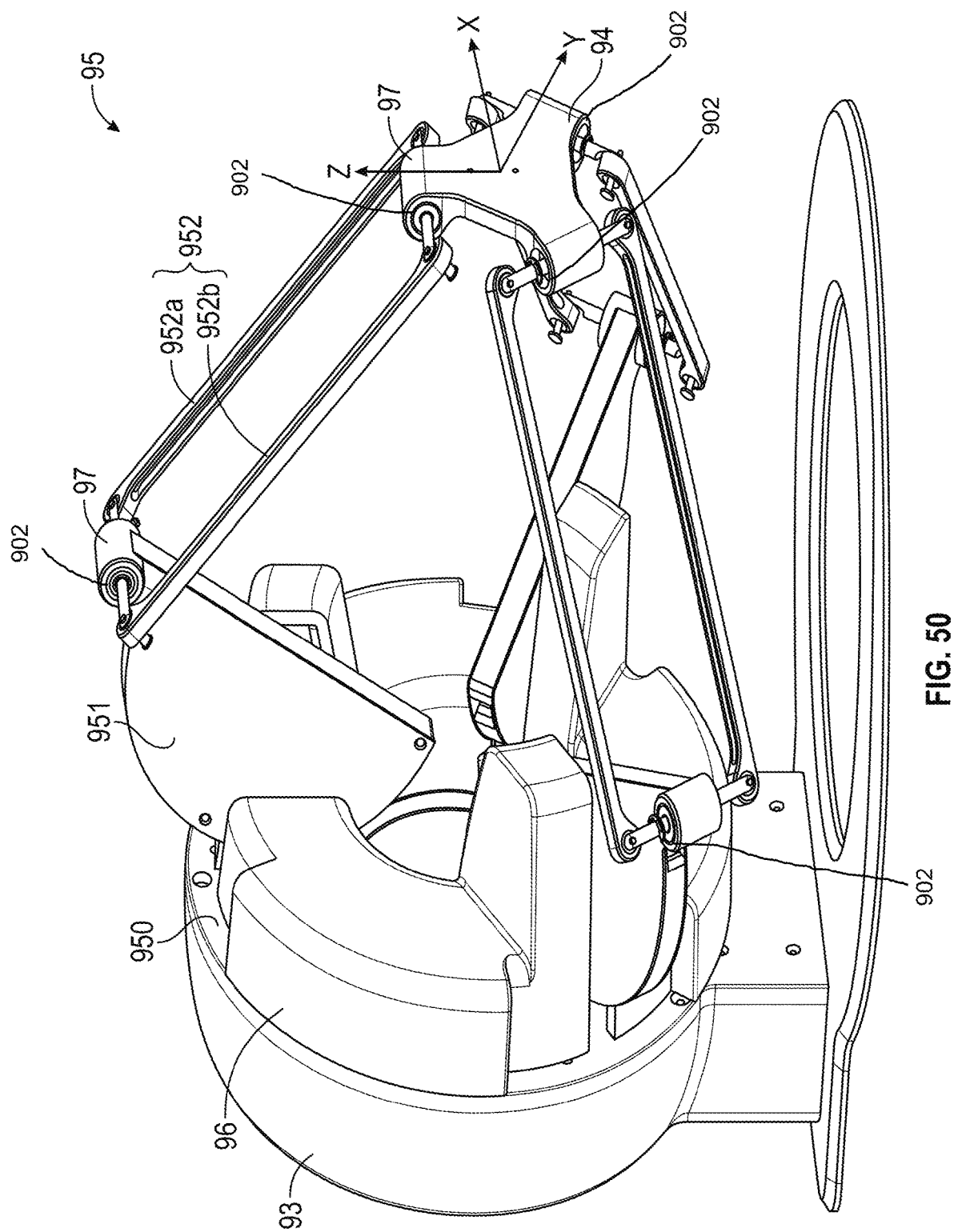
FIG. 50 is an isometric view schematically illustrating parts (i.e. the base member, the moveable member, and three parallel kinematics chain) of the control platform of the personalized master controller in FIG. 49.

FIG. 49 is a view schematically illustrating a personalized master controller according to another exemplary embodiment of the present invention. FIG. 50 is view schematically illustrating parts of the control platform of the personalized master controller in FIG. 49. In this embodiment, the control platform 90 may be a device comprising parallel kinematics structures, in particular, a Delta parallel kinematics structure device (for example, as described in US 2008/0223165 A1 which is incorporated herein by reference in its entirety). As shown in FIG. 49, the control platform 90 is adapted to provide up to six degrees of freedom (i.e. up to three translational degrees of freedom in X, Y, and Z directions and up to three rotational degrees of freedom in pitch, yaw, and roll orientations to provide a position parameter and an orientation parameter, respectively.

In this embodiment, the control platform 90 may comprise: a base member 93, a moveable member 94, and three parallel kinematics chains 95 coupling the base member 93 and the moveable member 94, respectively. Each parallel kinematics chain 95 having a first arm 951 moveable in a respective movement plane 950 which is at a distance to a symmetry axis (i.e. the central line perpendicular to the base member 93). Each first arm 951 is coupled with its associated mounting member 96 such that each first arm 951 may be rotated or pivoted with respect to the associated mounting member 96 and, thus, with respect to the base member 93.

The parallel kinematics chains 95 comprising a second arm 952 may be coupled to the moveable member 94. Each second arm 952 may be considered as parallelogram including two linking bars 952a, 952b. At proximal end of the second arm 952, each linking bar 952a and 952b may be coupled with the moveable member 94 by a joint or hinge 97. At the distal end of the second arm 952, each linking bar 952a, 952b are coupled with an end of its associated first arm 951 by a joint or hinge 97. Each second arm 952, particularly each linking bar 952a, 952b, may have two rotational degrees of freedom at both ends.

Thus, each kinematics chain 95 connected between the base member 93 and the moveable member 94 may be moved in a movement space defined by the base member 93, the moveable member 94, and three parallel kinematics chains 95 to provide up to three translational degrees of freedom (along the X, Y, and Z directions, respectively as shown in FIG. 50), generating one or more position parameters P1. More details for the Delta parallel kinematics structure device may be referred to, for example, US 2008/0223165 A1 which has been incorporated herein by reference in its entirety.

In addition, up to three rotational degrees of freedom may be provided by a wrist structure 940 coupled to the moveable member 94, comprising a three pivotable connections 941, 942 and 943, for example in form of pivot joints. Each of the pivotable connections 941, 942 and 943 provides a rotational degree of freedom with respect to the moveable member 94 (in yaw, pitch, and roll orientations respectively in FIG. 51), and generates one or more orientation parameters P2 thereby.

There are a plurality of first sensors 902 provided to detect one or more position parameters P1 and/or the orientation parameters P2 caused by the movement of three parallel kinematics chains 95 and the moveable member 94, followed by generating first movement signals S8 in response to the parameter(s) P1 and or P2. For example, some first sensors 902 may be installed to each mounting member 96 respectively to detect at least one parameter caused by the motion of the associated first arm 951. Other first sensors 902 may be installed to all or parts of joint or hinge 97 respectively to detect at least one parameter caused by the motion of the associated second arm 952. Alternatively, three first sensors 902 may be provided at three pivotable connections 941, 942 and 943 respectively.

Figure 51:
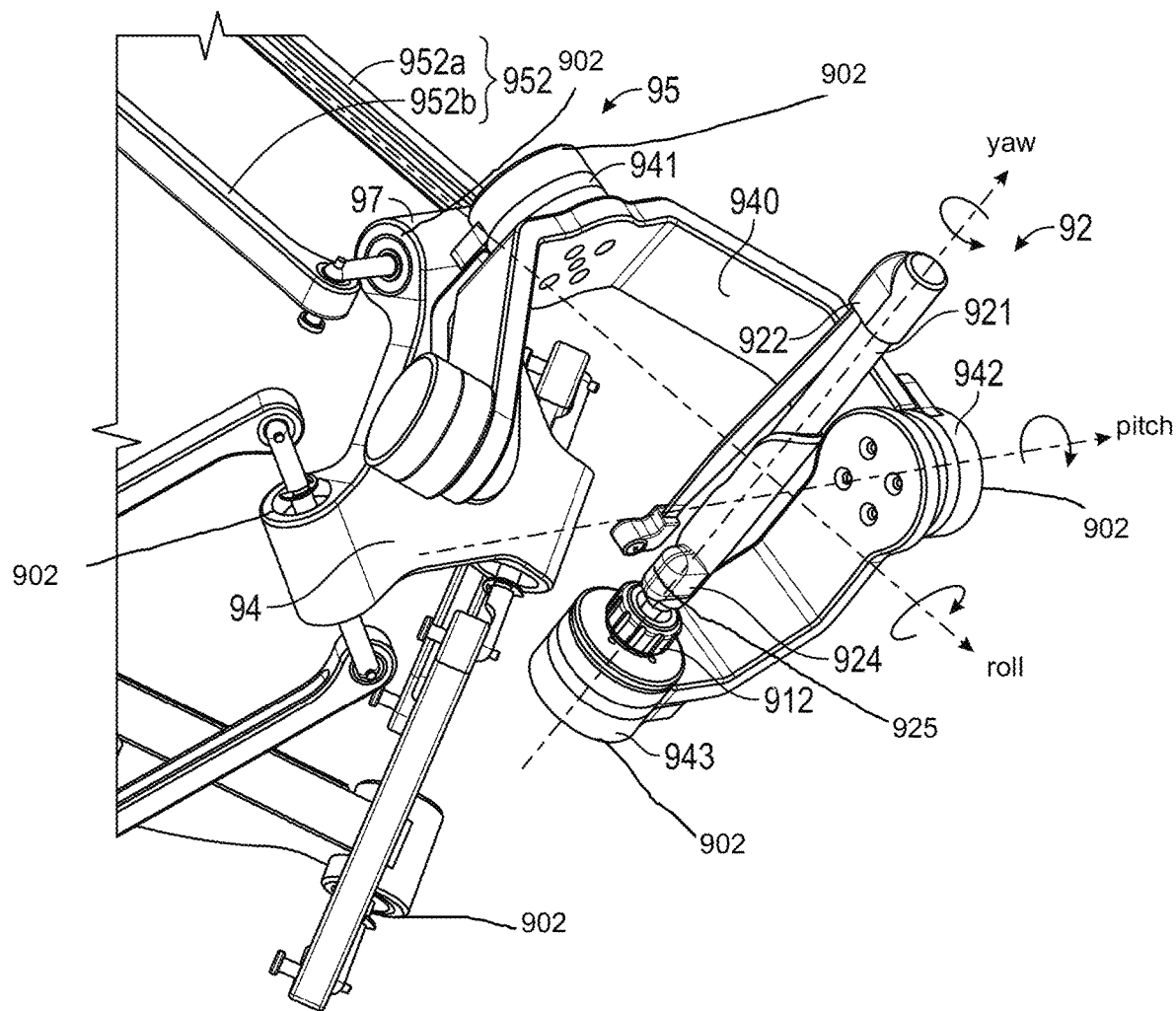
FIG. 51 is an enlarged view of a portion of FIG. 49 showing the interchangeable grip being attached to the moveable member of the control platform according to an exemplary embodiment of the present invention.
Figure 52:
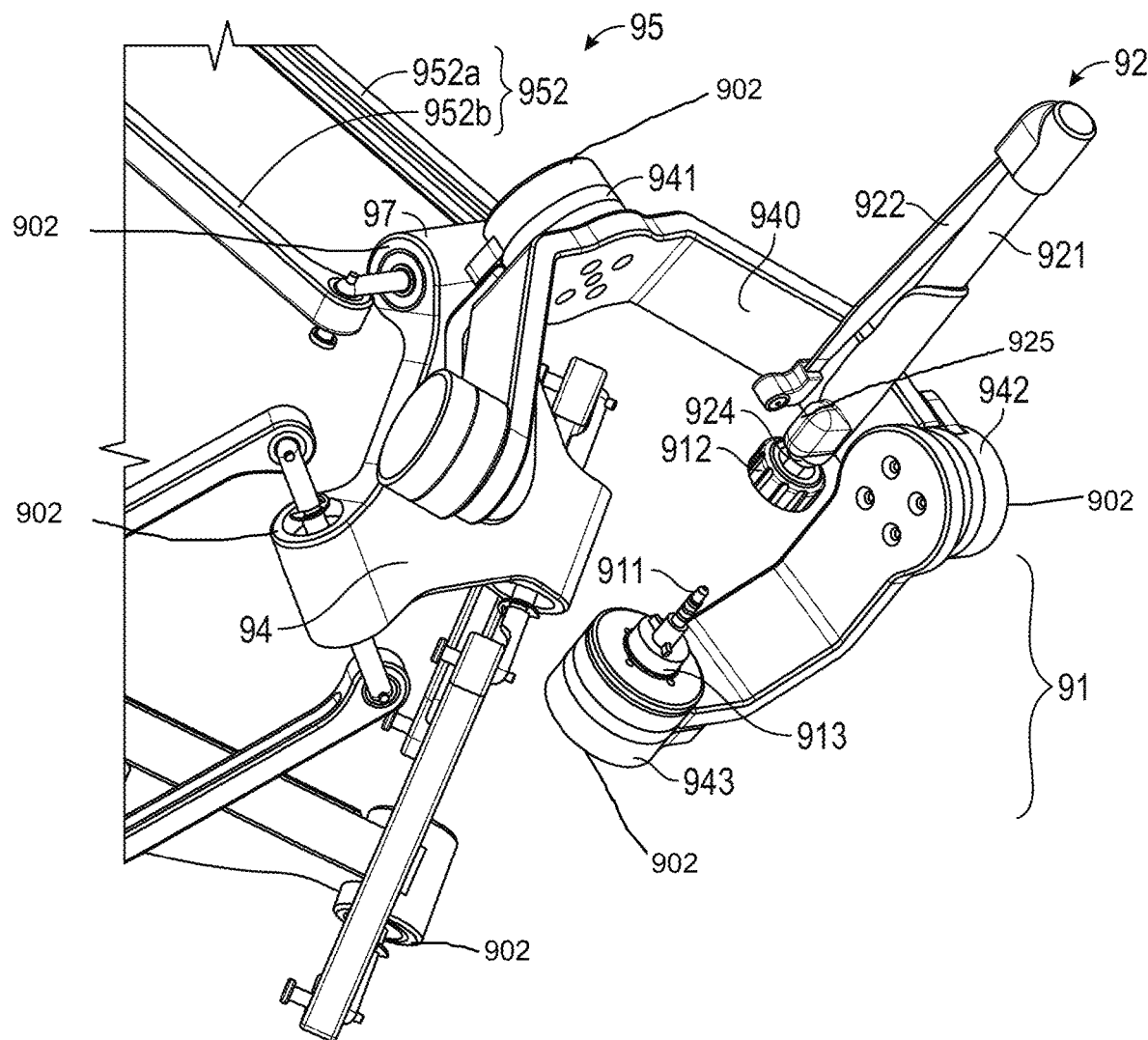
FIG. 52 is an enlarged view of a portion of FIG. 49 showing the interchangeable grip being detached from the moveable member of the control platform according to an exemplary embodiment of the present invention.

FIG. 51 is an enlarged view of a portion of FIG. 49 showing the interchangeable grip being attached to the moveable member of the control platform according to an exemplary embodiment. FIG. 52 is also an enlarged view of a portion of FIG. 49 showing the interchangeable grip being detached from the moveable member of the control platform according to an exemplary embodiment. As shown in FIG. 52, a connecting part 91 is further mounted on the pivotable connection 943, such that it can electrically connect the input handle 901 and the interchangeable grip 92. As shown in FIG. 52, in one embodiment, the connecting part 91 may comprise be a plug-and-socket type connector, but not limited to this. For example, a one-prong plug 911 of the connecting part 91 may be coupled to the detachable handle 921 of the interchangeable grip 92 via a thread 913, while a corresponding socket structure 912 may be mounted at the pivotable connection 943, so that that the interchangeable grip may be attached to (see FIG. 51) or detached from (see FIG. 52) the pivotable connection 943 and allowed to rotate with respect to the rotational axis A10 of the pivotable connection 943.

As seen above, several exemplary embodiments of a surgical apparatus have been described. However, these exemplary embodiments are for illustrative purposes only. For example, the above-described surgical instruments may be configured as individual surgical apparatuses, or they may be applied to a variety of medical devices, such as a lumen unit or imaging unit with a working channel, as well as to a surgical apparatus with an end effector. Furthermore, various embodiments of a steerable member may be integrated or otherwise adapted for a variety of surgical apparatuses, including, but not limited to, catheters, endoscopes, and surgical robots that are bendable at the distal end thereof.

As used herein, the terms "comprises," "comprising," "includes," "including," "has," "having," or any other variation thereof, are intended to cover a non-exclusive inclusion. For example, a process, product, article, or apparatus that comprises a list of elements is not necessarily limited only those elements but may include other elements not expressly listed or inherent to such process, product, article, or apparatus.

Furthermore, the term "or" as used herein is generally intended to mean "and/or" unless otherwise indicated. For example, a condition A or B is satisfied by any one of the following: A is true (or present) and B is false (or not present), A is false (or not present) and B is true (or present), and both A and B are true (or present). As used herein, a term preceded by "a" or "an" (and "the" when antecedent basis is "a" or "an") includes both singular and plural of such term, unless clearly indicated otherwise (i.e., that the reference "a" or "an" clearly indicates only the singular or only the plural). Also, as used in the description herein, the meaning of "in" includes "in" and "on" unless the context clearly dictates otherwise.

It will also be appreciated that one or more of the elements depicted in the drawings/figures can also be implemented in a more separated or integrated manner, or even removed or rendered as inoperable in certain cases, as is useful in accordance with a particular application. Additionally, any signal arrows in the drawings/figures should be considered only as exemplary, and not limiting, unless otherwise specifically noted. The scope of the disclosure should be determined by the following claims and their legal equivalents.

In some embodiments is a surgical apparatus comprising: a surgical apparatus comprising: a steerable member that is bendable and comprises a plurality of bending segments with channels therein; and a plurality of bending actuation wires that are arranged to pass through the steerable member and cause the steerable member to bend, the steerable member comprising at least one lumen through which the bending actuation wires pass, and the lumen being partially open outward. In some embodiments, the bending segments are hinged to adjacent bending segments. In other embodiments, the connecting parts of each bending segment are pinned to an adjacent bending segment. In other embodiments, the connecting parts of each bending segment are accommodated in recess parts of the adjacent bending segment and hinged thereto. In other embodiments, each connecting part comprises a protrusion with a round surface, and each recess part is shaped to accommodate each connecting part such that each connecting part may rotate. In other embodiments, each connecting part comprises a protrusion with a linear edge, and each recess part is shaped like a v-shaped notch such that each connecting part may rotate while in linear contact with each recess part. In alternative embodiments, a pair of connecting parts are provided facing each other on one side of the length of each bending segment, a pair of recess parts are provided facing each other on the other side of the length of each bending segment, and the pair of connecting parts and the pair of recess parts are arranged in a direction perpendicular to each other so as to permit bending in at 2 degrees of freedom. In other embodiments, four lumens are formed along the length of each bending segment, and each lumen passes through at least a portion of a connecting part or a recess part. In some aspects, each lumen comprises a closed lumen portion and an open lumen portion, and a portion of each lumen passing through the connecting part or the recess part forms a closed lumen portion and the other side of the connecting part or the recess part forms an open lumen portion. In other embodiments, each bending segment has four lumens along the length, and each lumen is located between the locations of the connecting part and recess part along the circumference. In other embodiments, each lumen comprises a closed lumen portion and an open lumen portion, wherein the closed lumen portion is formed at the middle of the lumen length and the open lumen portion is formed on both sides of the closed lumen portion. In some embodiments, the steerable member comprises a plurality of plate-like bending segments and connecting parts of flexible material located between the bending segments. In other embodiments, the connecting parts are formed integrally between the bending segments and extend from two edge of the channels provided at the center of the bending segments to an outward direction, and the connecting parts are formed in a direction perpendicular to adjacent connecting parts. In other embodiments, the bending actuation wires are arranged to pass through the bending segments and the connecting parts, and each lumen with a bending actuation wire provided therein has a structure in which a portion located at a connecting part forms a closed lumen and a portion formed at a bending segment is open outward. In other embodiments, the connecting parts are configured to connect the centers of adjacent bending segments.

In some embodiments of the surgical apparatus further comprises an end effector provided at the distal end of the steerable member. In some embodiments, the end effector is connected to an effector actuation wire located in the channels of the steerable member such that it may be actuated by moving the effector actuation wire, and at least part of the end effector is detachably provided at the distal end of the effector actuation wire. In some embodiments, at least part of the end effector is magnetically connected to the distal end of the effector actuation wire. In other embodiments, the end effector comprises an effector module comprising: an instrument portion for performing a surgical operation; and an actuation portion connected to the effector actuation wire to actuate the instrument portion, wherein at least either the proximal end of the effector module or the distal end of the effector actuation wire comprises a magnetic body. In some embodiments, the surgical apparatus further comprises an effector actuation wire that is located in the channels of the steerable member and connected to the end effector to actuate the end effector, and the end effector further comprises an elastic body that is configured to produce an elastic force in the opposite direction to a force applied by the effector actuation wire. In other embodiments, the effector actuation wire is configured such that the end effector operates in a first mode when pulled by the effector actuation wire and operates in a second mode while not pulled by the effector actuation wire. In other embodiments, a forceps of the end effector is closed in the first mode and open in the second mode. In some embodiments, the end effector comprises: an instrument portion for performing a surgical operation; an actuation portion connected to the effector actuation wire to actuate the instrument portion; and a body portion forming a path along which the actuation portion reciprocates, wherein the elastic body is located at the proximal end of the actuation portion and applies an elastic force in a direction that pushes the actuation portion. In other embodiments, the actuation portion and the distal end of the effector actuation wire are configured to be attachable to or detachable from each other. In other embodiments, at least either the actuation portion or the distal end of the effector actuation wire comprises a magnetic body.

In some embodiments of the surgical apparatus, a wire termination member for fixing the distal ends of the bending actuation wires is provided at the distal end of the steerable member. In some embodiments, the wire termination member has a thread such that the bending actuation wires are fixed by screwing the wire termination member to the distal end of the steerable member. In other embodiments, the bending actuation wires are arranged to be fixed by being pushed while wound between the distal end of the steerable member and the wire termination member. In some embodiments, the wire termination member comprises at least one hole through which the distal ends of the bending actuation wires pass, and the wire termination member is provided at the distal end of the steerable member. In other embodiments, the holes in the wire termination member are formed at locations corresponding to the lumens in the steerable member. In other embodiments, the surgical apparatus further comprises an end effector provided at the distal end of the steerable member, the wire termination member being the end effector.

In some embodiments is a surgical apparatus comprising: a steerable member that is bendable and comprises a plurality of bending segments with channels therein; a plurality of bending actuation wires that are arranged to pass through the steerable member and cause the steerable member to bend, and the steerable member comprising at least one lumen through which the bending actuation wires pass; wherein the surgical apparatus further comprises: a flexible member comprising a flexible material that is provided at the proximal end of the steerable member; and at least one sleeve forming a path of travel of a wire passing through the steerable member or the flexible member, both ends of which are fixed to the inside thereof. In some embodiments, the wire comprises the bending actuation wires. In some embodiments, the body of the sleeve is longer than the longest possible path that is formed between two points at which both opposite ends of the sleeve are fixed when the steerable member or the flexible member is bent, in order to minimize the effect of the bending of the steerable member or flexible member on the movement of the wire in the sleeve. In some embodiments, the steerable member and the flexible member have a hollow space for the sleeve to be placed therein. In some embodiments, a second sleeve out of the at least one sleeve forms a path for the distal end bending actuation wire, one end of the second sleeve being fixed at the proximal end of the distal end steerable portion or the distal end of the proximal end steerable portion and the other end being fixed at the proximal end of the flexible member. In other embodiments, the second sleeve comprises an elastic material so that the distal end bending actuation wire is located along a curved path when the distal end steerable portion is bent. In some embodiments a third sleeve out of the at least one sleeve forms a path along for the proximal end bending actuation wire, one end of the third sleeve being fixed at the proximal end of the proximal end steerable portion or the distal end of the flexible member and the other end being fixed at the proximal end of the flexible member. In other embodiments, the third sleeve comprises an elastic material so that the proximal end bending actuation wire is located along a curved path when the proximal end steerable portion is bent.

In some embodiments is a surgical apparatus comprising: (Amended) A surgical apparatus comprising: a steerable member that is bendable and comprises a plurality of bending segments with channels therein; a plurality of bending actuation wires that are arranged to pass through the steerable member and cause the steerable member to bend, and the steerable member comprising at least one lumen through which the bending actuation wires pass; a flexible member comprising a flexible material that is provided at the proximal end of the steerable member and forms a path along which the bending actuation wires pass; and a manipulating part that is provided at the proximal end of the flexible member for actuating the bending actuation wires, wherein the proximal ends of the bending actuation wires are attachable to or detachable from the manipulating part. In other embodiments, the proximal ends of the bending actuation wires and effector actuation wire are magnetically and detachably connected to the manipulating part.

In some embodiments is a surgical apparatus, wherein the bending actuation wires comprise a first bending actuation wire, and a second bending actuation wire that causes the steerable member to bend in the opposite direction to the first bending actuation wire, wherein screw members rotating in the same direction are provided at the proximal end of the first bending actuation wire and the proximal end of the second bending actuation wire and are configured to move in synch with each other in opposite directions. In some embodiments, the proximal end of the first bending actuation wire is configured to move along a first thread, and the proximal end of the second bending actuation wire is configured to move along a second thread oriented in the opposite direction to the first thread. In other embodiments, the first tread and the second thread are configured to rotate in the same direction by a single driving part. In other embodiments, the screw members are bi-directional lead screws, each having first and second thread portions formed on a single body. In other embodiments, the screw members comprise: a first lead screw with a first thread; and a second lead screw with a second thread, wherein the first lead screw and the second lead screw are configured to move in sync with each other by a gear and rotate simultaneously by a single driving part.

In some embodiments of the surgical apparatus, the steerable member has a geometric shape configured to bend more easily at the distal end than at the proximal end. In some embodiments, the bending segments have a geometric shape configured such that the steerable member bends more easily closer to its proximal end. In some embodiments, the bending segments have lumens formed at a distance from the center of a cross-section of the steerable member, and the closer to the proximal end of the steerable member, the more distant the lumens in the bending segments get from the center of the cross-section of the steerable member. In some embodiments, the steerable member further comprises a plurality of connecting parts located between the bending segments, wherein the connecting parts have a geometric shape configured such that the steerable member bends more easily closer to its proximal end. In other embodiments, the connecting parts are configured to have a smaller sectional width toward the proximal end of the steerable member so that the corresponding parts of the steerable member bend more easily. In other embodiments, the connecting parts are configured to increase in diameter along the length toward the proximal end of the steerable member so that the corresponding parts of the steerable member bend more easily.

In some embodiments is a surgical apparatus, comprising: a steerable member that is bendable; an end effector provided at the distal end of the steerable member; and an effector actuation wire that is arranged to pass through the steerable member and connect to the end effector to actuate the end effector, the end effector comprising an elastic body that produces an elastic force in the opposite direction to the force applied by the effector actuation wire. In some embodiments, the end effector is configured to operate in a first mode when pulled by the effector actuation wire and is configured to operate in a second mode by the elastic force of the elastic body while not pulled by the effector actuation wire. In other embodiments, the end effector is actuated in such a way that surgical elements at the distal end are closed in the first mode and open in the second mode. In other embodiments, the end effector further comprises an effector module comprising: an instrument portion for performing a surgical operation; an actuation portion connected to the effector actuation wire to actuate the instrument portion; and a body portion forming a path along which the actuation portion reciprocates. In other embodiments, the elastic body is located at the proximal end of the actuation portion for applying an elastic force to push the actuation portion in the direction of the distal end. In some embodiments, the effector module and the distal end of the effector actuation wire are configured to be attachable to or detachable from each other. In other embodiments, the effector module and the effector actuation wire are magnetically connected together.

In some embodiments is a surgical apparatus, comprising: a steerable member that is bendable; a plurality of bending actuation wires that are arranged to pass through the steerable member and cause the steerable member to bend; and a wire termination member provided at the distal end of the steerable member to fix the bending actuation wires, wherein the wire termination member has a thread for engaging with the distal end of the steerable member, such that the bending actuation wires are fixed by screwing the wire termination member and the steerable member together. In some embodiments, the bending actuation wires are configured to be fixed by winding between the distal end of the steerable member and the wire termination member. In other embodiments, the wire termination member comprises at least one hole through which the distal ends of the bending actuation wires pass, and the wire termination member is provided at the distal end of the steerable member. In other embodiments, the holes in the wire termination member are formed at locations corresponding to the lumens in the steerable member. In some embodiments, the end effector is provided on the wire termination member. In some embodiments, the surgical apparatus further comprises an end effector provided at the distal end of the steerable member, the wire termination member being the end effector.

In some embodiments is a surgical apparatus, comprising: a steerable member that is bendable; a first bending actuation wire that is arranged to pass through the steerable member to cause the steerable member to bend in a first direction; a second bending actuation wire that is arranged to pass through the steerable member to cause the steerable member to bend in a second direction which is opposite to the first direction; and at least one screw member to which the proximal end of the first bending actuation wire and the proximal end of the second bending actuation wire are coupled, such that the steerable member bends in the first or second direction by rotating the at least one screw member. In some embodiments, the at least one screw member is arranged to rotate about the longitudinal axes of the first and second bending actuation wires. In some embodiments, the proximal end of the first bending actuation wire and the proximal end of the second bending actuation wire are configured to move in sync with each other in opposite directions by rotation of the at least one screw member. In other embodiments, when the at least one screw member is configured to rotate in a first direction of rotation to move the proximal end of the first bending actuation wire backward and the proximal end of the second bending actuation wire forward, thereby causing the steerable member to bend in the first direction, and a second direction of rotation to move the proximal end of the first bending actuation wire forward and the proximal end of the second bending actuation wire backward, thereby causing the steerable member to bend in the second direction. In some embodiments, the proximal end of the first bending actuation wire is engaged with and moves along a first thread, and the proximal end of the second bending actuation wire is engaged with and moves along a second thread oriented in the opposite direction to the first thread. In other embodiments, the first thread and the second thread are configured to rotate in the same direction, such that the proximal end of the first bending actuation wire and the proximal end of the second bending actuation wire are configured to move in sync with each other in opposite directions. In some embodiments, the at least one screw member is a bi-directional lead screw having first and second thread portions formed on a single body.

In some embodiments is a surgical apparatus, comprising: a steerable member that is bendable; and a plurality of bending actuation wires that are arranged to pass through lumens in the steerable member and cause the steerable member to bend, wherein the steerable member has a geometric shape configured such that the steerable member bends more easily closer to its distal end. In some embodiments, the geometric shape is configured to provide a smaller radius of curvature closer to the proximate end of the steerable member.

In some embodiments is a surgical apparatus, comprising: a steerable member that is bendable and comprises a plurality of bending segments with channels therein; a plurality of bending actuation wires that are arranged to pass through the steerable member and cause the steerable member to bend; and a lateral supporting member that comprises an elastic material and exerts a restoration force for returning the steerable member to the initial position after bending. In some embodiments, the surgical apparatus further includes a plurality of lateral supporting members wherein the number of lateral supporting members is equal to the number of bending actuation wires. In some embodiments, the lateral supporting member is configured to bend in sync with the steerable member by the movement of the bending actuation wires, and the lateral supporting member has an elasticity configured such that it returns to its original shape when the force exerted on the bending actuation wires is released, thus bringing the steerable member back to the initial position. In some embodiments, the shape of the lateral supporting member before bending is linear. In some embodiments, the shape of the lateral supporting member before bending is bent to one side. In other embodiments, the lateral supporting members is configured in a tube shape, and a bending actuation wire is located inside the lateral supporting member.

In some embodiments is a surgical apparatus, comprising: a steerable member that is bendable and comprises a plurality of bending segments with channels therein and a plurality of connecting segments located between the bending segments; and a plurality of bending actuation wires that are arranged to pass through the steerable member and cause the steerable member to bend, wherein two ends of each connecting segment are hinged to different bending segments. In some embodiments, each connecting segment comprises: a pair of bodies that form portions hinged to the bending segment; and a guide member that joins together the pair of bodies and has a hollow space inside it where the bending actuation wires are located. In some embodiments, a bending segment connected to one end of each connecting segment is rotatable about a first hinge shaft, and a bending segment connected to the other end is rotatable about a second hinge shaft, and the first hinge shaft and the second hinge shaft are parallel to each other. In some embodiments, each connecting segment is arranged in a different direction from adjacent connecting segments to cause the connected bending segments to bend about different axes of rotation, in order to enable the steerable member to bend at least 2 degrees of freedom. In some embodiments, each bending segment comprises a plurality of lumens where the bending actuation wires are located, the lumens being arranged to not pass through the portions hinged to the connecting segment. In some embodiments, the bending segments are rotatably connected to the connecting segments, and the hinge shafts about which the bending segments rotate are in the same plane as the ends of the lumens where the bending actuation wires are located.

In some embodiments is a surgical apparatus, comprising: a steerable member that is bendable and comprises a plurality of bending segments, wherein each bending segment includes at least an intermediate joint having a first link portion and a second link portion and wherein the intermediate joint is arranged along a longitudinal axis direction of each bending segment; a plurality of bending actuation wires that are arranged to pass through the steerable member for causing the steerable member to bend; wherein the steerable member further comprises at least one lumen through which the bending actuation wires pass; and the intermediate joint further comprises a tension-regulating member which is coupled to the first link portion and the second link portion and is configured to regulate the tension of bending actuation wires by compensating the elongation of the bending actuation wires when bending segments bend, whereby the length of bending actuation wires is altered and kept in a predetermined tension. In other embodiments, the first interfacing half has a protrusion end, and the second interfacing half correspondingly has a recess end. In other embodiments, the first interfacing half has a recess end, and the second interfacing half correspondingly has a protrusion end. In some embodiments, the elongation of the bending actuation wires is compensated by being offset of two off-axis hinges. In some embodiments, the bending segment includes a series of interstacked intermediate joints.

In some embodiments is a surgical apparatus, comprising: a steerable member that is bendable and comprises a plurality of bending segments and a plurality of lumens; a bending actuation member, comprising a first bending actuation wire and a second bending actuation wire that are arranged to pass through each lumen separately and cause the steerable member to bend; a tension monitoring member, comprising: a first sensor that is coupled to the first bending actuation wire and configured to provide a first feedback signal responsive to sensing change in tension force of the first bending actuation wire between the pre-bending and the desired bending motion of the steerable member; a second sensor that is coupled to the second bending actuation wire and configured to provide a second feedback signal responsive to sensing change in tension force of the second bending actuation wire between the pre-bending and the desired bending motion of the steerable member; a drive member, comprising: a first motor, coupled to the first bending actuation wire and adapted to actuate the first bending actuation wire; a second motor coupled to the second bending actuation wire and adapted to actuate the second bending actuation wire; a control member that is electrically connected to the tension monitoring member and the drive member, wherein the control member is configured to provide: a first output signal responsive to the first feedback signal, so that the first motor is driven to adjust the length of the first bending actuation wire to maintain a predetermined tension; and a second output signal responsive to the second feedback signal, so that the second motor is driven to adjust the length of the second bending actuation wire to maintain a predetermined tension. In some embodiments, the second bending actuation wire is moveable in an opposite direction of the first bending actuation wire. In some embodiments, when the first bending actuation wire is configured to be actuated to bend the steerable member, and the second bending actuation wire is configured to be driven by the second motor, so that the second bending actuation wire is released and maintained under the predetermined tension in response to the second output signal. In some embodiments, the first sensor or the second sensor is load cell. In some embodiments, the first sensor is further configured to provide a first external-force signal responsive to sensing an external force applied to the steerable member. In some embodiments, the second sensor is further configured to provide a second external-force signal responsive to sensing an external force applied to the steerable member. In other embodiments, the control member is further configured to provide an instruction signal in response to the first external-force signal or the second external-force signal. In other embodiments, the control member further comprises a haptic feedback controller that is configured to process and transfer the information in the form of haptic feedback. In other embodiments, the first motion transmitting unit or the second motion transmitting unit is a lead screw or a ball screw.

In some embodiments is a personalized master controller for a surgical apparatus, comprising: a control platform that is configured to define and input one or more movement signals to the surgical robot, wherein the control platform comprises: an input handle that is translatable in a first plurality of degrees of freedom to provide a plurality of position parameters and/or rotatable in a second plurality of degrees of freedom to provide a plurality of orientation parameters; a plurality of first sensors that are coupled to the input handle and configured to generate first movement signals in response to the position parameters and/or the orientation parameters of the input handle; a connecting part mounted to the input handle and electrically connected to the input handle; and an interchangeable grip, comprising: a detachable handle that is electrically connected the connecting part; one or more grip levers pivoted with respect to the detachable handle, wherein each grip lever is moveable in a third degree of freedom relative to the detachable handle so as to provide a gripping motion parameter; and a second sensor that is coupled to the detachable handle and configured to generate a second movement signal to the control platform in response to the gripping motion parameter. In some embodiments, the first plurality of sensors or the second plurality of sensors includes a rotary encoder, a Hall effector sensor, an angle sensor, a rotational sensor or any combination thereof. In some embodiments, the connecting part further comprises a thread that is coupled to the detachable handle and has a first electrical connecting terminal. In other embodiments, the detachable handle further comprises a second electrical connecting terminal that is electrically connected to the first electrical connecting terminal. In some embodiments, the interchangeable grip comprises two grip levers that are correspondingly pivoted to the detachable handle and allow to move toward each other relative to the detachable handle.

What is claimed is:

1. A surgical apparatus comprising:
a steerable member that is bendable and comprises a plurality of bending segments with channels therein, the steerable member comprising at least one lumen;
a plurality of bending actuation wires that are arranged to pass through the at least one lumen of the steerable member and cause the steerable member to bend;
a flexible member comprising a flexible material that is provided at a proximal end of the steerable member;
an end effector provided at a distal end of the steerable member;
an effector actuation wire that is arranged to pass through the steerable member and the flexible member and connected to the end effector to actuate the end effector; and
at least one sleeve forming a path of travel of the effector actuation wire passing through the steerable member or the flexible member, both ends of the sleeve being fixed to an inside of the steerable member or the flexible member;
wherein a body of the sleeve is longer than a distance of the steerable member or the flexible member between two points at which both opposite ends of the sleeve are fixed; and
wherein the sleeve comprises an elastic material.

2. A surgical apparatus comprising:
a steerable member that is bendable and comprises a plurality of bending segments with channels therein, the steerable member comprising at least one lumen;
a plurality of bending actuation wires that are arranged to pass through the at least one lumen of the steerable member and cause the steerable member to bend;
a flexible member comprising a flexible material that is provided at a proximal end of the steerable member;
an end effector provided at a distal end of the steerable member;
an effector actuation wire that is arranged to pass through the steerable member and the flexible member and connected to the end effector to actuate the end effector; and
at least one sleeve forming a path of travel of the effector actuation wire passing through the steerable member or the flexible member, both ends of the sleeve being fixed to an inside of the steerable member or the flexible member;
wherein a body of the sleeve is longer than the longest possible path of the effector actuation wire that is formed between two points at which both opposite ends of the sleeve are fixed when the steerable member or the flexible member is bent; and
wherein the sleeve comprises an elastic material.

3. The surgical apparatus of claim 1 or 2, wherein the steerable member and the flexible member have a hollow space for the sleeve to be placed therein.

4. The surgical apparatus of any one of claims 1-3, wherein both opposite ends of the at least one sleeve are fixed at the distal end of the steerable member and the proximal end of the flexible member.

5. A surgical apparatus comprising:
a steerable member that is bendable and comprises a plurality of bending segments with channels therein, the steerable member comprising at least one lumen;
a plurality of bending actuation wires that are arranged to pass through the at least one lumen of the steerable member and cause the steerable member to bend; and
a flexible member comprising a flexible material that is provided at a proximal end of the steerable member;
wherein the steerable member comprises a distal end steerable portion and a proximal end steerable portion, which bend separately, wherein the distal end steerable portion is configured to bend with a distal end bending actuation wire provided along the at least one lumen in the distal end steerable portion, and the proximal end steerable portion is configured to bend with a proximal end bending actuation wire provided along the at least one lumen in the proximal end steerable portion; and
wherein the surgical apparatus further comprises:
at least one sleeve forming a path for the distal end bending actuation wire and/or a path for the proximal end bending actuation wire, passing through the steerable member or the flexible member, both ends of the sleeve being fixed to an inside of the steerable member or the flexible member;
wherein a body of the sleeve is longer than a distance of the steerable member or the flexible member between two points at which both opposite ends of the sleeve are fixed; and
wherein the sleeve comprises an elastic material.

6. A surgical apparatus comprising:
a steerable member that is bendable and comprises a plurality of bending segments with channels therein, the steerable member comprising at least one lumen;
a plurality of bending actuation wires that are arranged to pass through the at least one lumen of the steerable member and cause the steerable member to bend; and
a flexible member comprising a flexible material that is provided at a proximal end of the steerable member;
wherein the steerable member comprises a distal end steerable portion and a proximal end steerable portion, which bend separately, wherein the distal end steerable portion is configured to bend with a distal end bending actuation wire provided along the at least one lumen in the distal end steerable portion, and the proximal end steerable portion is configured to bend with a proximal end bending actuation wire provided along the at least one lumen in the proximal end steerable portion; and
wherein the surgical apparatus further comprises:
at least one sleeve forming a path for the distal end bending actuation wire and/or a path for the proximal end bending actuation wire, passing through the steerable member or the flexible member, both ends of the sleeve being fixed to an inside of the steerable member or the flexible member;
wherein a body of the sleeve is longer than the longest possible path of the distal end bending actuation wire and/or the proximal end bending actuation wire that is formed between two points at which both opposite ends of the sleeve are fixed when the steerable member or the flexible member is bent; and
wherein the sleeve comprises an elastic material.

7. The surgical apparatus of claim 5 or 6, wherein the at least one sleeve includes at least a sleeve forming a path for the distal end bending actuation wire, one end of the sleeve forming a path for the distal end bending actuation wire being fixed at a proximal end of the distal end steerable portion or a distal end of the proximal end steerable portion and the other end being fixed at a proximal end of the flexible member.

8. The surgical apparatus of claim 7, wherein the distal end bending actuation wire is located along a curved path when the distal end steerable portion is bent.

9. The surgical apparatus of claim 5 or 6, wherein the at least one sleeve includes at least a sleeve forming a path for the proximal end bending actuation wire, one end of the sleeve forming a path for the proximal end bending actuation wire being fixed at a proximal end of the proximal end steerable portion or a distal end of the flexible member and the other end being fixed at a proximal end of the flexible member.

10. The surgical apparatus of claim 9 wherein the proximal end bending actuation wire is located along a curved path when the proximal end steerable portion is bent.

* * * * *